United States Patent [19]

Roessler et al.

[11] Patent Number: 5,559,220
[45] Date of Patent: Sep. 24, 1996

[54] GENE ENCODING ACETYL-COENZYME A CARBOXYLASE

[75] Inventors: Paul G. Roessler, Golden, Colo.; John B. Ohlrogge, Okemos, Mich.

[73] Assignee: Midwest Research Institute, Kansas City, Mo.

[21] Appl. No.: 418,893

[22] Filed: Apr. 7, 1995

Related U.S. Application Data

[63] Continuation of Ser. No. 120,938, Sep. 14, 1993, abandoned.

[51] Int. Cl.⁶ .............................. C12N 15/29; C12N 5/04; C12N 15/55; C12N 9/18; C12N 1/13
[52] U.S. Cl. .............. 536/23.6; 536/23.2; 435/69.1; 435/134; 435/172.3; 435/240.4; 435/252.3; 435/257.2; 435/320.1; 435/197
[58] Field of Search ................... 536/23.2, 23.6; 435/69.1, 134, 172.3, 240.4, 252.3, 257.2, 320.1, 197

[56] References Cited

U.S. PATENT DOCUMENTS

| | | | |
|---|---|---|---|
| 4,769,061 | 9/1988 | Comai | 435/172.3 |
| 5,110,728 | 5/1992 | Kridl et al. | 435/69.1 |

FOREIGN PATENT DOCUMENTS

| | | | |
|---|---|---|---|
| 469810 | 2/1992 | European Pat. Off. | C07K 13/00 |

OTHER PUBLICATIONS

Lopez-Casillas et al., Proc. Natl. Acad. Sci. U.S.A. 85: 5784–5788 (1988).
Takai et al., J. Biol. Chem. 263: 2651–2657 (1988).
Al-Feel et al., Proc. Natl. Acad. Sci. U.S.A. 89: 4534–4538 (1992).
Li et al., J. Biol. Chem. 267: 855–863 (1992).
Li et al., J. Biol. Chem. 267: 16841–16847 (1992).
Kondo et al., Proc. Natl. Acad. Sci. U.S.A. 88: 9730–9733 (1991).
Alix, DNA 8: 779–789 (1989).
Roessler, Plant Physiology 92: 73–78 (1990).
Egli et al., Plant Physiol. 101: 499–506 (1993).
Livne et al., Plant Cell Physiol. 31: 851–858 (1990).
Charles et al., Phytochemistry 25: 1067–1071 (1986).
Slabas et al., Plant Science 39: 177–182 (1985).
Nikolau et al., Arch. Biochem. Biophys. 228: 86–96 (1984).
Egin-Buhler et al., Eur. J. Biochem. 133: 335–339 (1983).
Finlayson et al., Arch. Biochem. Biophys. 225: 576–585 (1983).
Weissman et al., *Biotech. Bioeng.* 31: 336–344 (1988).
Roessler, Arch. Biochem. Biophys. 267: 521–528 (1988).
Roessler et al. 1992. Plant Physiol. 99 (suppl. 1): 19.
Pikaard et al. 1986. Nucleic Acids Research 14(13): 5564–6.
Barker et al. 1983. Plant Molec. Biol. 2: 335–350.
Gordan-Kamm et al. 1990. Plant Cell 2: 603–618.
Boyton et al. 1988. Science 240: 1534–1538.

*Primary Examiner*—David T. Fox
*Attorney, Agent, or Firm*—Edna M. O'Connor; Ruth Eure

[57] ABSTRACT

A DNA encoding an acetyl-coenzyme A carboxylase (ACCase) from a photosynthetic organism and functional derivatives thereof which are resistant to inhibition from certain herbicides. This gene can be placed in organisms to increase their fatty acid content or to render them resistant to certain herbicides.

9 Claims, 2 Drawing Sheets

Fig. 2A

| | | | | | | | | | | | | | | | | | | | | | |
|---|---|---|---|---|---|---|---|---|---|---|---|---|---|---|---|---|---|---|---|---|---|
| Cyclotella ACC (1476-1526) | G | R | Q | V | V | V | I | V | N | D | V | T | V | Q | S | G | F | G | V | E | E | D | E | V | F | F | K | A | S | K | Y | A | R | E | N | K | L | P | R | V | Y | H | A | C | N | S | G | A | R | I |
| Yeast ACC (1579-1629) | G | R | Q | V | V | V | A | N | D | H | T | F | K | I | G | S | F | G | P | Q | E | D | E | F | F | N | K | V | T | E | Y | A | R | K | R | G | I | P | R | I | Y | L | A | A | N | S | G | A | R | I |
| Rat ACC (1672-1722) | G | R | D | V | I | G | N | D | H | Y | R | H | G | S | F | G | P | Q | E | D | E | F | F | N | K | V | T | E | Y | A | R | K | R | G | I | P | R | I | Y | V | A | A | N | S | G | A | R | I |
| E.coli β-CT (117-167) | G | M | P | V | V | A | A | A | F | E | F | A | P | M | G | G | S | M | G | S | V | V | G | A | R | F | V | R | A | V | E | Q | A | L | E | D | N | C | P | L | I | C | F | S | A | S | G | G | A | R | M |

Fig. 2B

| | | | | | | | | | | | | | | | | | | | | |
|---|---|---|---|---|---|---|---|---|---|---|---|---|---|---|---|---|---|---|---|---|
| Cyclotella ACC (1758-1777) | G | K | S | V | V | I | G | R | G | R | L | G | G | I | P | M | G | A | I | A |
| Yeast ACC (1878-1897) | A | K | G | V | V | V | G | R | A | R | L | G | G | I | P | L | G | V | I | G |
| Rat ACC (1967-1986) | A | Q | T | V | V | V | G | R | A | R | L | G | G | I | P | V | G | V | V | A |
| E.coli α-CT (98-117) | D | K | A | I | V | G | G | I | A | R | L | D | G | R | P | V | M | I | I | G |

Fig. 2C

| | | | | | | | | | | | | | | | | | | | | |
|---|---|---|---|---|---|---|---|---|---|---|---|---|---|---|---|---|---|---|---|---|
| Cyclotella ACC (287-307) | E | N | G | I | M | I | K | A | S | E | G | G | G | G | K | G | I | R | F | V | D |
| Yeast ACC (246-266) | G | F | P | V | M | I | K | A | S | E | G | G | G | G | K | G | I | R | Q | V | E |
| Rat ACC (304-324) | G | Y | P | V | M | I | K | A | S | E | G | G | G | G | K | G | I | R | K | V | N |
| E. coli BC (153-173) | G | Y | P | V | I | I | K | A | S | G | G | G | G | R | G | M | R | V | V | R |

GENE ENCODING ACETYL-COENZYME A CARBOXYLASE

The United States Government has rights on this invention pursuant to Contract No. DE-AC02-83CH10093 between the United States Department of Energy and the Midwest Research Institute.

This is a continuation of application Ser. No. 08/120,938 filed Sep. 14, 1993, now abandoned.

FIELD OF THE INVENTION

Background Of The Invention

The invention relates to a cloned gene which encodes an enzyme, its uses and products resulting from its use.

RELATED WORK TO THE INVENTION

Lipids, particularly triglycerides, have a great deal of commercial value in food and industrial products. Sunflower, safflower, rape, olive, soybean, peanut, flax, castor, oil palm, coconut and cotton are examples of major crops which are grown primarily or secondarily for their lipids. All agricultural animals provide animal sources for commercial fats and oils.

Recently, agriculturally produced triglycerides have even been proposed for use as a diesel fuel. These products are biodegradable and are less polluting than their fossil fuel counterparts. Their primary drawback is cost. Consequently, there has been considerable research to improve the yields of lipids from agricultural sources.

In an attempt to enhance production of oils in plants, the acyl carrier protein gene has been cloned so that the gene may be overproduced in hopes of increasing production. See U.S. Pat. No. 5,110,728. While acyl carrier protein is involved in the biosynthesis of lipids, it is not believed to be the rate limiting component. Thus it is not clear whether organisms containing such a cloned gene would increase production of lipids as the result of having multiple gene copies.

In the biosynthesis of fatty acids in bacteria, animals, yeast, and plants, the first step is catalyzed by the enzyme Acetyl-Coenzyme A carboxylase, hereafter ACCase. This enzyme catalyzes the carboxylation of acetyl-CoA to form malonyl-CoA. The reaction involves two partial reactions: 1) carboxylation of an enzyme bound biotin molecule to form a carboxybiotin-enzyme complex and 2) transfer of the carboxyl group to acetyl-CoA. ACCase catalyzes the primary regulatory or rate-limiting step in the biosynthesis of fatty acids.

In bacteria such as *Escherichia coli*, the ACCase has four distinct, separable protein subunit components; a biotin carboxyl carrier protein, a biotin carboxylase and two subunits of carboxyltransferase. In eukaryotes, ACCase is composed of multimers of a single multifunctional polypeptide having a molecular mass typically greater than 200 kDa (Samols et al, J. Biol. Chem. 263: 6461–6464 (1988)). These multimers have molecular masses ranging from 400 kDa to 8 MDa.

Some confusion exists as to the size of ACCase from plants. Large (>200 KDa) subunits have been reported for several plants. See, e.g., Roessler, Plant Physiology 92: 73–78 (1990); Egli et al, Plant Physiol. 101: 499–506 (1993); Livne et al, Plant Cell Physiol. 31: 851–858 (1990); Charles et al, Phytochemistry 25: 1067–1071 (1986); Slabas et al, Plant Science 39: 177–182 (1985); Egin-Buhler et al, Eur. J. Biochem. 133: 335–339 (1983). Wurtele et al (Arch. Biochem. Biophys. 278: 179–186 (1990)) suggest that plants may also have an ACCase made up of much smaller subunits.

In animals, ACCase has been shown to catalyze the rate limiting step in fatty acid biosynthesis. See, e.g. Kim et al, FASEB J. 3: 2250–2256 (1989) and Lane et al, *Current Topics in Cellular Recognition,* Horecker et al, ed. (Academic Press, N.Y.) 8: 139–195 (1974). Regulation of the level of gene expression has been shown to be an important determinant of fatty acid biosynthetic rates in animals (Katsurada et al, Eur. J. Biochem. 190: 435–441 (1990); Pape et al, Arch. Biochem. Biophys. 267: 104–109 (1988)). This same enzyme has recently been proposed to determine the rates of fatty acid synthesis in plants as well (Post-Beittenmiller et al, J. Biol. Chem. 266: 1858–1865 (1991) and Post-Beittenmiller et al, Plant Physiol. 100: 923–930 (1992)). However, nothing is known about the regulation of plant ACCase gene expression.

In addition to the enzyme being well characterized in many species, the gene coding for ACCase and its subunits have been cloned from rat, chicken, yeast and *E. coli.* See Lopez-Casillas et al., Proc. Natl. Acad. Sci. U.S.A. 85: 5784–5788 (1988); Takai et al., J. Biol. Chem. 263: 2651–2657 (1988); Al-Feel et al, Proc. Natl. Acad. Sci. U.S.A. 89: 4534–4538 (1992); Li et al., J. Biol. Chem. 267: 855–863 (1992); Li et al., J. Biol. Chem. 267: 16841–16847 (1992); Kondo et al, Proc. Natl. Acad. Sci. U.S.A. 88: 9730–9733 (1991) and Alix, DNA 8: 779–789 (1989). However, as mentioned above, considerable variability in the structures of the encoded enzymes has been noticed.

ACCase has been purified from several species of plants and algae. See, e.g. Roessler, Plant Physiology 92: 73–78 (1990); Egli et al, Plant Physiol. 101: 499–506 (1993); Livne et al, Plant Cell Physiol. 31: 851–858 (1990); Charles et al, Phytochemistry 25: 1067–1071 (1986); Slabas et al, Plant Science 39: 177–182 (1985); Nikolau et al, Arch. Biochem. Biophys. 228: 86–96 (1984); Egin-Buhler et al, Eur. J. Biochem. 133: 335–339 (1983) and Finlayson et al, Arch. Biochem. Biophys. 225: 576–585 (1983). The genes encoding ACCase from these and other photosynthetic organisms have not been cloned. Nikolau et al, EP 469,810 has reported cloning a 50 kDa "subunit" from carrots. However, this is clearly not large enough to be a full length copy of the gene.

*Cyclotella cryptica* is a diatom which is photosynthetic and can potentially produce up to half of its mass as lipids (Weissman et al, *Biotech. Bioeng.* 31: 336–344 (1988)). *C. cryptica* is capable of culture outdoors in saline groundwater which is unsuitable for normal agricultural crops. Calculations have indicated that theoretically, *C. cryptica* could produce more lipids than are currently produced by agricultural oilseeds. As such, *C. cryptica* has been considered as a potential organism for producing lipids.

Previous research has suggested that increased levels of ACCase gene expression may be responsible for enhanced ACCase activity in nutrient-deficient, lipid-accumulating *C. cryptica* cells (Roessler, Arch. Biochem. Biophys. 267: 521–528 (1988)). However, before the present invention, this hypothesis could not be tested. Furthermore, other than changing the culturing medium, no other mechanism for regulating expression existed.

In order for this natural alga to accumulate large amounts of lipids, nutrient-limiting conditions have been used. See Roessler, Arch. Biochem. Biophys. 267: 521–528 (1988) and Werner, Arch. Mikrobiol. 55: 278–308 (1966). The limiting nutrient was silicon or nitrogen. The activity of the ACCase doubled after 4 hours of silicon deficiency increased four-fold after 15 hours. The exact mechanism by which nutrients control ACCase activity is unknown.

SUMMARY OF THE INVENTION

An object of this invention is to produce large quantities of lipids, particularly triglycerides, at lower cost.

Another object of the present invention is to develop plants and other organisms which overproduce lipids in order to produce lipids at lower cost.

Still another object of this invention is to generate plants which are herbicide resistant so that weeding of a field can be performed efficiently.

Yet another object of the present invention is to prepare a selectable marker for use in plant breeding.

To accomplish these goals, the gene for ACCase from *C. cryptica* has been cloned. The gene may be expressed in *C. cryptica* to increase the copy number of the ACCase gene or to place the gene under different regulatory control. Alternatively, the ACCase gene may be expressed in other organisms such as bacteria, yeast, plants and algae, so that the lipid compositions of the organisms are altered.

The ACCase produced by the cloned gene is resistant to the effects of certain herbicides. Thus, the gene can serve as a marker by imparting herbicide resistance on a recipient cell which is normally herbicide sensitive. This has certain advantages in plant breeding and in weeding a field of plants.

BRIEF DESCRIPTION OF THE DRAWINGS

FIGS. 2A–2C shows a comparison of the amino acid sequences of ACCase from four different species. The portion of ACCase that binds to carboxybiotin is believed to correspond to A. The acetyl-CoA binding region is believed to correspond to B. The ATP binding region is believed to correspond to C. The amino acid sequences are provided in computer readable form as SEQ ID NO:1 to SEQ ID NO:12.

DESCRIPTION OF THE PREFERRED EMBODIMENT

Figure 1A:
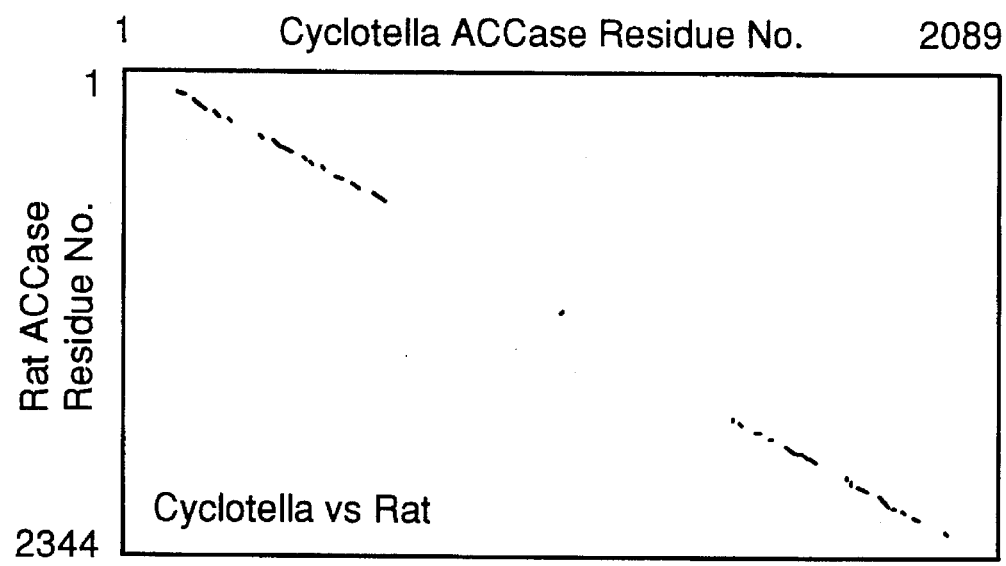
FIGS. 1A–1B are a homology plot comparing the deduced amino acid sequence of *C. cryptica* ACCase with the sequences of rat and yeast ACCases. The areas marked are where seven or more amino acids out of ten are identical in the two sequences being compared.

The gene for ACCase encodes a 2089 amino acid protein having a molecular mass of 230 kDa. The gene also contains a 447-base pair intron near the putative translation initiation codon and a 73-base pair intron slightly upstream from the region of the gene that encodes the biotin binding site of the enzyme. A signal sequence is present in the enzyme which resembles that capable of transporting proteins into a chloroplast or other plastid via the endoplasmic reticulum.

The ACCase gene was cloned using standard recombinant DNA techniques. Variations on these techniques are well known and may be used to reproduce the invention. Techniques for transforming host cells, expressing the gene and altering the host organism are also known and are used in accordance with the present invention.

Standard reference works setting forth the general principles of recombinant DNA technology and cell biology include Watson, J. D., et al., *Molecular Biology of the Gene*, Volumes I and II, Benjamin/Cummings Publishing Co., Inc., Menlo Park, Calif. (1987); Darnell, J. E. et al., *Molecular Cell Biology*, Scientific American Books, Inc., New York, N.Y. (1986); Lewin, B. M., *Genes II*, John Wiley & Sons, New York, N.Y. (1985); Old, R. W. et al., *Principles of Gene Manipulation: An Introduction to Genetic Engineering*, 2nd Ed., University of California Press, Berkeley, Calif. (1981); Maniatis, T., et al. (*Molecular Cloning: A Laboratory Manual*, Cold Spring Harbor Press, Cold Spring Harbor, N.Y. (1982)); Sambrook, J. et al. (*Molecular Cloning: A Laboratory Manual*, 2nd Edition, Cold Spring Harbor Press, Cold Spring Harbor, N.Y. (1989)) and Albers, B. et al., *Molecular Biology of the Cell*, 2nd Ed., Garland Publishing, Inc., New York, N.Y. (1989). These references and all other references mentioned in this application are herein incorporated by reference.

By "cloning" is meant the use of in vitro recombination techniques to insert a particular gene or other DNA sequence into a vector molecule. In order to successfully clone a desired gene, it is necessary to employ methods for generating DNA fragments, for joining the fragments to vector molecules, for introducing the composite DNA molecule into a host cell in which it can replicate, and for selecting the clone having the target gene from amongst the recipient host cells.

By "cDNA" is meant complementary or copy DNA produced from an RNA template by the action of RNA-dependent DNA polymerase (reverse transcriptase). Thus a "cDNA clone" means a duplex DNA sequence complementary to an RNA molecule of interest, which may be carried in a cloning vector.

By "vector" is meant a DNA molecule, derived from a plasmid, bacteriophage or hybrid, into which fragments of DNA may be inserted or cloned. A vector will contain one or more unique restriction sites, and may be capable of autonomous replication in a defined host or vehicle organism such that the cloned sequence is reproducible. Thus, by "expression vector" is meant any autonomous element capable of replicating in a host cell independently of the host's chromosome, after a "replicon" has been incorporated into the autonomous element's genome. Such DNA expression vectors include bacterial plasmids and phages and typically include promoter sequences to facilitate gene transcription.

A "replicon" is a sequence of DNA, gene or genes, that when ligated to other DNA causes the entire DNA to be replicated in a cell. The replicon may be on a plasmid, virus, cosmid or chromosome which can replicate in a host cell. The DNA can have any positive number of replicons. DNA containing one or more replicons may occur any positive number of times in a cell.

For the purposes of this application, the term "ACCase gene from *C. cryptica*" includes all nucleotide sequences possible which encode the same amino acid sequence. By "functional derivative" is meant the "fragments," "variants," "analogs," or "chemical derivatives" of a molecule. A "fragment" of a molecule, such as any of the DNA fragments of the present invention or a cDNA of the ACCase gene, is meant to refer to any nucleotide subset of the molecule. A "variant" of such molecule is meant to refer to a naturally occurring molecule substantially similar in structure and function to either the entire molecule or a fragment thereof. An "analog" of a molecule is meant to refer to a non-natural molecule substantially similar to either the entire molecule or a fragment thereof.

A "promoter" contains a promoter (which directs the initiation of RNA transcription) as well as the DNA sequences which, when transcribed into RNA, will signal the initiation of protein synthesis. "Regulatory regions" contain both the promoter and other elements which control the activity of the promoter. Such regions will normally include those 5'-non-coding sequences involved with initiation of transcription and translation, such as the TATA box, capping sequence, CAAT sequence, and the like. They may also include enhancer, inducer or repressor sequences and binding sites, etc.

A DNA is said to be "capable of expressing" a polypeptide if it contains nucleotide sequences which contain signals for transcriptional and translational initiation, and such sequences are "operably linked" to nucleotide sequences which encode the polypeptide. An operable linkage is a linkage in which the signals for transcriptional and translational initiation and the DNA sequence sought to be expressed are connected in such a way as to permit gene expression. The precise nature of the signals required for gene expression may vary from organism to organism.

The "polymerase chain reaction" or "PCR" is an in vitro enzymatic method capable of specifically increasing the concentration of a desired nucleic acid molecule (Mullis et al., *Cold Spring Harbor Symp. Quant. Biol.* 51: 263–273 (1986); Erlich et al., EP 50,424, EP 84,796, EP 258,017 and EP 237,362; Mullis, EP 201,184; Mullis et al., U.S. Pat. No. 4,683,202; Erlich U.S. Pat. No. 4,582,788; and Saiki et al., U.S. Pat. No. 4,683,194). PCR provides a method for selectively increasing the concentration of a particular sequence even when that sequence has not been previously purified and is present only in a single copy in a sample. The method can be used to amplify either single- or double-stranded DNA. The method involves use of two oligonucleotides to serve as primers for the template-dependent, polymerase-mediated replication of a nucleic acid molecule.

The precise nature of the two oligonucleotide primers is critical to the success of the PCR method. As is well known, a molecule of DNA or RNA possesses directionality, which is conferred through the 5'-3' linkage of the phosphate groups. The oligonucleotide primers of the PCR method are selected to contain sequences identical to, or complementary to, sequences which flank the ACCase nucleic acid sequence whose amplification is desired.

The DNA molecule of the present invention can be produced through any of a variety of means, preferably by application of recombinant DNA techniques. Techniques for synthesizing such molecules are disclosed by, for example, Wu, R., et al. *Prog. Nucl. Acid. Res. Molec. Biol.* 21: 101–141 (1978). Procedures for constructing recombinant molecules in accordance with the above-described method are disclosed by Sambrook et al., *Molecular Cloning: A Laboratory Manual*, Second Edition, Cold Spring Harbor Press, Cold Spring Harbor, N.Y. (1989), which reference is herein incorporated by reference.

PCR and many of its variations are well known in the art. By using PCR with the primers described below the ACCase gene can be obtained. By permitting cycles of polymerization and denaturation, a geometric increase in the concentration of the ACCase nucleic acid molecule can be achieved which makes the cloning process much easier or at least possible. Reviews of the PCR are provided below and thus further discussion is not necessary. See Mullis, K. B. (*Cold Spring Harbor Symp. Quant. Biol.* 51: 263–273 (1986)); Saiki, R. K., et al. (*Bio/Technology* 3: 1008–1012 (1985)); and Mullis, K. B., et al. (*Meth. Enzymol.* 155: 335–350 (1987)).

A DNA sequence encoding the ACCase gene of the present invention, or its functional derivatives, may be recombined with vector DNA in accordance with conventional techniques, including restriction enzyme digestion to provide appropriate blunt-ended or staggered-ended termini, filling in of cohesive ends as appropriate, alkaline phosphatase treatment to avoid undesirable joining, ligation with appropriate ligases, or the synthesis of fragments by the polymerase chain reaction (PCR). Techniques for such manipulations are disclosed by Sambrook et al., supra, and are well known in the art.

Once the ACCase gene has been cloned, one may express the gene in a host cell by ligating it to a vector appropriate for the eventual desired host, transferring the vector to the host cell and culturing the host cell in a manner which permits expression of the gene. Numerous vectors, host cells and techniques for their uses are known per se and are discussed in many of the references cited in this application.

Intact functional ACCase protein can be made in a number of organisms by providing a promoter and transcriptional and translational start sites. These genetic elements can be derived from the DNA of other organisms, and it also may be possible to use the genetic elements that naturally occur as part of the *C. cryptica* ACCase gene. Expression levels of ACCase may vary from less than 1% to more than 30% of total cell protein.

If desired, the non-coding region 3' to the gene sequence coding for the protein may be obtained by the above-described methods. This region may be retained for its transcriptional termination regulatory sequences, such as termination and polyadenylation signals. Thus, by retaining the 3'-region naturally contiguous to the DNA sequence coding for the protein, the transcriptional termination signals may be provided. Where the transcriptional termination signals are not satisfactorily functional in the expression host cell, then a 3' region functional in the host cell may be substituted.

Two DNA sequences (such as a promoter region sequence and the ACCase structural gene sequence) are said to be operably linked if the nature of the linkage between the two DNA sequences does not (1) result in the introduction of a frame-shift mutation, (2) interfere with the ability of the promoter region sequence to direct the transcription of the ACCase gene sequence, or (3) interfere with the ability of the ACCase gene sequence to be transcribed. A promoter region would be operably linked to a DNA sequence if the promoter were capable of effecting transcription of that DNA sequence. Thus, to express the protein, transcriptional and translational signals recognized by an appropriate host are necessary.

Depending on the host cell, one may wish to use either the natural ACCase promoter or a different promoter. The choice of promoters will depend on the host cell and the timing and degree of expression desired. For expression in algae, particularly *C. cryptica*, the natural promoter and regulatory sequences may be used. For expression in different organisms, a different promoter is usually preferred. However, in order to regulate gene expression differently in *C. cryptica*, one may use a different regulatory system which may be artificially modified or mutate the natural ACCase gene regulatory system.

If the host cell is a bacterium, generally a bacterial promoter and regulatory system will be used. For a typical bacterium such as *E. coli*, representative examples of well known promoters include trc, lac, tac, trp, bacteriophage lambda $P_L$, T7 RNA polymerase promoter, etc. When the expression system is yeast, examples of well known promoters include: GAL 1/GAL 10, alcohol dehydrogenase (ADH), his3, cycI, etc. For eukaryotic hosts, enhancers such as the yeast Ty enhancer may be used.

For multicellular organisms, one has additional concerns with expression of the ACCase gene in certain tissues as well as the timing of expression. The choice of promoter is dependant on the eventual use. In such a situation, it may be advantageous to use tissue- or developmental stage- regulated regulatory elements.

For example, if one wished to increase the lipid content of oilseeds, one would use the ACCase structural gene and a promoter which is active in seed development. Expression need not occur at any other location in the plant. Examples include the promoters to seed storage proteins such as phaseolin, napin, oleosin, glycinin, cruciferin, etc. An example of one such promoter, soybean betaconglycinin, is described by Beachy et al, EMBO J. 4: 3047–3053 (1985).

Alternatively, if one wished for the ACCase to be expressed at only a particular time, such as after the culture or host organism has reached maturity, an externally regulated promoter is particularly useful. Examples include those based upon the nutritional content of the medium (e.g. lac, trp, his), temperature regulation (e.g. temperature sensitive regulatory elements), heat shock promoters (e.g. HSPSOA, U.S. Pat. No. 5,187,267), stress response (e.g. plant EF1A promoter, U.S. Pat. No. 5,177,011) and chemically inducible promoters (e.g. tetracycline inducible promoter or salicylate inducible promoter U.S. Pat. No. 5,057,422).

In certain uses, such as making a host resistant to herbicides by expressing the ACCase gene, one may wish for the ACCase gene expression to be continuous and in multiple tissue types. Representative examples of constitutive promoters include the Cauliflower Mosaic Virus 35S promoter (Odell et al, Nature 313: 810–812 (1985); Bevan et al, EMBO J. 4: 1921–1926 (1985)) and its enhancer (Simpson et al, Nature 323: 551–554 (1986)), mannopine synthetase promoter (U.S. Pat. No. 5,106,739), nopaline synthetase promoter (Bruce et al, Mol. Cell. Biol. 7: 59 (1987)), the $T_L$ DNA of an Ri plasmid and the OCS promoter and enhancer (Ellis et al, EMBO J. 6: 11 (1987)).

Other promoters of somewhat narrower host range may also be used such as wheat promoters (U.S. Pat. No. 5,139,954) and the ribulose 1,5-biphosphate carboxylase promoter (U.S. Pat. No. 4,962,028).

The selection of promoters, enhancers and regulatory elements of all kinds is readily determinable. While not every combination will be successful and not every successful combination will be appropriate for all uses, the choice among known systems is easily determined by those skilled in the art. To further optimize ACCase gene expression, one may mutate the regulatory elements to eliminate or modify one of the activities.

Some promoters are applicable in multiple hosts such as the soybean heat shock promoter being expressed by sunflower (Schoffl et al, EMBO J. 4: 1119–1124 (1985)). Intracellular plant parasites such as viruses or bacteria typically have promoters recognized by a wider range of host organisms. For example, the Cauliflower Mosaic Virus 35S promoter and Aqrobacterium tumefaciens T-DNA promoters have a very wide host range. However, the host range of many regulatory elements is limited to only one or a few species.

Enhancers are usually critical to tissue specific expression of a particular gene. By using the corresponding promoter and enhancer, one may direct synthesis of ACCase to any plant tissue so desired. For example if higher oil seeds are desired, a seed specific enhancer may be helpful. Likewise for preparing herbicide resistance from a herbicide which inhibits normal plant ACCase but not *C. cryptica* ACCase, expression in all tissues, or at least tissues exposed to the herbicide such as leaves and stems, is desirable.

Vectors, including expression vectors, may be transferred into a cell by a variety of techniques depending on the host cell. For bacteria, the vector may be added to the host cell by transformation which is well known per se. Generally, recombinant DNA techniques are performed in bacteria for simplicity.

The same techniques can be used when the host cell is a yeast, fungus, alga or plant cell. Before attempting to transform yeast cells, a replicon for yeast needs to be added to the vector. The previous bacterial replicon need not be removed thereby permitting the plasmid to be shuttled between both organisms in what is called a "shuttle vector".

For transference of a vector to plants, a virus, T-DNA or physical techniques are generally used. As with bacteriophages, plant viruses may be designed to carry foreign DNA by techniques known per se. *Agrobacterium tumefaciens* is a bacterium which infects many plants and inserts a segment of DNA called T-DNA into the plant genome. By removing unnecessary genes from the T-DNA and adding the ACCase gene of the present invention, the *A. tumefaciens* carrying the ACCase gene can infect and transfer the gene to a plant host. The techniques for such DNA transfer are known per se. Furthermore, the DNA can be placed inside a plant cell by physical means such as microinjection and more recently by adsorbing the vector onto small particles and propelling or "shooting" them into plant cells or tissue. Use of these recent techniques to transform plants as diverse as maize, soybeans and pine trees are disclosed in U.S. Pat. Nos. 5,015,580 and 5,122,466.

Once plant cells have been transformed with foreign DNA, they may be reproduced and, if not already an entire plant, regenerated into a whole plant. One such example in soybeans is U.S. Pat. No. 5,024,944. Other examples include regeneration of monocotyledonous plants (U.S. Pat. No. 5,187,073) and particularly corn (U.S. Pat. No. 5,177,010). Whole plants may then reproduce and be bred by conventional plant breeding techniques, some of which have been used for thousands of years.

In some cases, the transformed cells of a host may be selected for based upon the newly acquired property of herbicide or antibiotic resistance. As such the ACCase gene of the present invention may be used as a selectable marker for detecting transformation. The ACCase gene may also be used as a reporter gene for which a number of promoters or regulatory regions may be added in order to assay for a promoter or to discover additional gene regulators. The choice of host cell for these functions is limited only to those that naturally contain an ACCase that is sensitive to compounds that have no pronounced effects on the activity of the *C. cryptica* ACCase.

ACCase from many monocotyledonous plants is strongly inhibited by several herbicides, particularly the aryloxyphenoxypropionate and cyclohexanedione herbicides (Burton et al, Biochem. Biophys. Res. Commun. 148: 1039–1044 (1987)). The mechanism of action of these classes of herbicides is by inhibiting the activity of ACCase. ACCase from *C. cryptica* is not strongly inhibited by these herbicides. Thus, the incorporation and expression of this gene into many monocotyledonous crop plants would be beneficial, as it would allow the use of these herbicides in fields where monocotyledonous weeds and other susceptible weeds occur. Examples of desirable monocotyledonous crops include both agricultural species such as corn, wheat, rice, barley, sugarcane, onion, garlic, asparagus, pineapple, etc. and ornamental plants such as grass, lily, orchids, narcissus etc. Similarly, this technique may be used for all other plants to make them resistant or more resistant to the effects of these classes of herbicides.

Techniques for producing herbicide resistance in plants by incorporating DNA encoding and expressing enzymes resistant to herbicides are known. For example, a different glutamine synthetase gene was added to make plants resistant to the herbicide phosphinothricen, U.S. Pat. No. 5,098,838 and U.S. Pat. No. 5,145,777. In a similar fashion, plants have been made resistant to different herbicides by adding foreign DNA encoding Glutathione S-Transferase which detoxifies certain herbicides, e.g. U.S. Pat. No. 5,073,677.

Perhaps the best known of the techniques for preparing a plant with an added foreign gene imparting herbicide resistance is that of glyphosate resistance (see Comai et al, Nature 313: 741–744 (1985)); U.S. Pat. Nos. 4,940,835 and 5,188,642. In this example a chloroplast transit sequence is added upstream from the herbicide resistance gene so that the protein product is transported into the chloroplasts.

In the same manner, and even using the same techniques and vectors, one or more copies of the ACCase gene from *C. cryptica* encoding herbicide resistance may be substituted for one of the other herbicide resistance genes of the references above. Since ACCase normally performs its function in the chloroplast, it is particularly relevant to use the above mentioned transit sequence or other plastid transit sequence to ensure expression in the chloroplast or other plastid. It may also be adequate or advantageous to express the ACCase gene in the cytoplasm (or endoplasmic reticulum) alone or supplementally. In such a situation, at least one of the gene construct(s) on the vector would not contain a plastid transit sequence.

Having generated a plant variety with a stable *C. cryptica* ACCase gene, one can cultivate the plant or plant cells in a conventional manner. If the plant cell is an alga, the gene may optionally be induced according to the regulatory regions and the lipids recovered by means conventional for recovering lipids from natural algae. If the plant has been designed to overproduce lipids, it may be grown, the ACCase gene induced and the lipids recovered by conventional methods. If the plant expresses the ACCase gene of the present invention for the purpose of making the plant resistant to a herbicide, it may be grown in soil (or a soil-less potting mix, hydroponic medium etc.) and the herbicide applied to inhibit weeds. For the purposes of this application "soil" is defined as any medium supporting plant growth, such as soil, water (for algae), sand, soil-less potting mixes, hydroponic medium etc.

Current attempts to alter the level of saturated fat content in animals and animal products have focused on conventional breeding rather than by preparing transgenic animals. Attempts to generate transgenic animals with altered lipid content have focused on adding a growth hormone gene to decrease overall fat content of the animal (Palmiter et al, Nature 300: 611–615 (1982)). In the present invention, one may add the ACCase gene simultaneously in the same plasmid or separately with the recombinant growth hormone gene in order to produce an animal which will have an altered ratio of fatty acids in its tissue. Alternatively, the ACCase gene may be added alone as the recombinant gene. In this fashion, the meat, milk or eggs from the transgenic animal may have a different ratio of saturated to unsaturated fats.

The ACCase molecule is said to be "substantially similar" to another molecule if the sequence of amino acids in both molecules is substantially the same. Substantially similar ACCase molecules will possess a similar biological activity. Thus, provided that two molecules possess a similar activity, they are considered "variants" as that term is used herein even if one of the molecules contains additional amino acid residues not found in the other, or if the sequence of amino acid residues is not identical. The ACCase from rat, yeast and *E. coli* are not considered substantially similar.

Similarly, a "functional derivative" of the ACCase gene of the present invention is meant to include shortened versions of the gene which encode a functionally equivalent ACCase, "variants," or "analogues" of the gene, which are "substantially similar" in amino acid sequence, and which encode a molecule possessing similar activity.

The nucleotide sequence may be altered to optimize the sequence for a given host. Different organisms have different codon preferences as has been reported previously. Furthermore, the nucleotide sequence may be altered to provide the preferred three dimensional configuration of the mRNA produced to enhance ribosome binding and expression. Introns may be removed from the gene either by restriction endonuclease cleavage or using the cloned gene as a hybridization probe for conventional cDNA cloning which may be applied to the ACCase gene. Note that the introns are provided in the sequence recited in the example. Alternatively, the same or different introns, may be added to the gene at acceptable locations. Enhancer element(s) may be located in the intron(s).

In the present invention, substantially similar ACCases can be made by changing the nucleotide sequence to produce a different amino acid sequence. Such changes may be advantageous to change the enzymatic properties of the ACCase. Alternatively, the change can be made to enhance production of active enzyme, such as changing internal amino acids to permit cleavage of ACCase from a fusion peptide or to add or subtract a site for various proteases. See, e.g., Oike, Y., et al., *J. Biol. Chem.* 257: 9751–9758 (1982); Liu, C., et al., *Int. J. Pept. Protein Res.* 21: 209–215 (1983). It should be noted that separation of ACCase from a leader sequence is not necessary provided that the ACCase activity is sufficiently acceptable.

Furthermore, if the ACCase gene uses a portion of another gene, such as an N-terminal region of said another gene, then it is advantageous to include a sequence encoding a cleavage site between said another gene and the ACCase gene. The cleavage site is preferably recognized by one of the host cell's internal proteases.

Changes to the sequence such as insertions, deletions and site specific mutations can be made by random chemical or radiation induced mutagenesis, restriction endonuclease cleavage, transposon or viral insertion, oligonucleotide-directed site specific mutagenesis, or by such standard techniques as Botstein et al, Science 229: 193–210 (1985). These techniques are known per se and have been made in a number of genes previously. Similar changes have been made in the structural genes encoding other plant enzymes affected by herbicides. One such example affecting glyphosate resistance is shown by U.S. Pat. No. 5,145,783.

Such changes may be made in the present invention to alter the enzymatic activity, render the enzyme more susceptible or resistant to temperature or chemicals (including herbicides), alter regulation of the ACCase gene, and to optimize the gene expression for any given host. These changes may be the result of either random changes or changes to a particular portion of the ACCase molecule believed to be involved with a particular function.

To further enhance expression, the final host organism may be mutated so that it will change gene regulation or its production of the ACCase gene product.

Unless specifically defined otherwise, all technical or scientific terms used herein have the same meaning as commonly understood by one of ordinary skill in the art to which this invention belongs. Although any methods and materials similar or equivalent to those described herein can be used in the practice or testing of the present invention, the preferred methods and materials are now described.

EXAMPLE

For the experiments below, the strain *Cyclotella cryptica* T13L was employed. This strain was obtained from the Bigelow Laboratory Culture Collection of Marine Phytoplankton, West Boothbay Harbor, Maine. *C. cryptica* was cultured as described in Roessler, J. Phycol. 24: 394–400 (1988).

ACCase from *C. cryptica* was purified to near homogeneity by means of ammonium sulfate precipitation, gel filtration chromatography, and monomeric avidin affinity chromatography as described previously (Roessler, Plant Physiol. 92: 73–78 (1990)), and then cleaved by the addition of CNBr. The peptides were separated by SDS-polyacrylamide gel electrophoresis, transferred onto a ProBlott membrane (Applied Biosystems; Foster City, Calif.), and stained with Coomassie Blue. Individual bands were excised for automated sequencing via the Edman degradation procedure, using an Applied Biosystems 477A protein sequenator with an on-line 120A PTH analyzer.

Partial amino acid sequences were determined for several peptides generated via CNBr-mediated cleavage of ACCase from *C. cryptica*. The sequences of two of these peptides were quite similar to sequences found in the biotin carboxylase domain of ACCase from rat mammary glands (Lopez-Casillas et al., Proc. Natl. Acad. Sci. U.S.A. 85: 5784–5788 (1988)) and chicken liver (Takai et al., J. Biol. Chem. 263: 2651–2657 (1988)) and were therefore used to design degenerate oligonucleotides for use as PCR primers. A 128-fold degenerate forward polymerase chain reaction (PCR) primer (PR1) and a 256-fold degenerate reverse PCR primer (PR2) were designed based on reverse translations of these two amino acid sequences. The sequences for the primers are given as follows:

| | |
|---|---|
| PR1 = TTYGTNTGGAAYGARGCNGA | SEQ ID NO:13 |
| PR2 = ACNGCRTTNCCRTGYTGRTC | SEQ ID NO:14 |

25 μl of PCR reaction mixture contained 50 ng DNA from *C. cryptica*, 0.1 μM of each primer species, 10 mM Tris-Cl (pH 8.3), 50 mM KCl, 1 mM $MgCl_2$, 0.2 mM dNTPs, and 1 U Taq DNA polymerase (Perkin Elmer-Cetus; Norwalk, Conn.). The following thermal cycle was used; Step 1, 94° C. for 5 min; Step 2, 94° C. for 1 min; Step 3, 45° C. for 2 min; Step 4, 2° C./sec to 72° C.; Step 5, repeat steps 2 to 4 for 30 times total; and Step 6, 72° C. for 8 min.

Using these primers, a 146-bp fragment was amplified from *C. cryptica* total DNA. This fragment was subcloned into the phagemid pBluescript KS+ (Stratagene; La Jolla, Calif.) that had been digested with EcoRV. The deduced amino acid sequence of this fragment exhibited 58% identity with the corresponding sequence of rat ACCase, thereby confirming that a *C. cryptica* ACCase gene fragment had been amplified. This sequence is shown below:

| | | |
|---|---|---|
| CYCLOTELLA | . . . LRNAFVQVSNEVIGSPIFLMQLCKNARHIEVQIVG . . . | SEQ ID NO:15 |
| RAT | . . . FPNLFRQVQAEVPGSPIFVMRLAKQSRHLEVQILA . . . | SEQ ID NO:16 |

In order to isolate the full-length ACCase gene, a genomic Lambda library was constructed. Total DNA was purified from *C. cryptica* as described by Jarvis et al. (Jarvis et al., J. Phycol. 28: 356–362 (1992)), except that the cells were disrupted in the extraction buffer by gentle inversions instead of by agitation with glass beads. The DNA was purified from contaminating polysaccharides by the use of hexadecyltrimethylammonium bromide (CTAB) (Murray et al., Nucleic Acids Res. 8: 4321–4325 (1980)), and then partially digested with Sau3AI. After partially filling in the overhangs by the addition of dGTP, dATP, and the Klenow fragment of *E. coli* DNA Polymerase I, the DNA was ligated to XhoI half-site arms of the Lambda phage derivative LambdaGEM-12 (Promega Corp.; Madison, Wis.) according to the manufacturer's instructions.

The entire unamplified library (~4×$10^4$) was plated out, using *E. coli* KW251 as the host strain. Plaques were lifted onto nitrocellulose membrane filters, which were treated with NaOH and neutralized via standard conditions (Sambrook et al., Molecular Cloning: A Laboratory Manual, 2nd Ed., Cold Spring Harbor Laboratory Press, N.Y. (1989)). After baking in vacuo for 1 h at 80° C., the filters were washed for 10 h at 42° C. in 5X SSPE/0.5% SDS, and then prehybridized for 6 h at 42° C. in hybridization solution (7% SDS/30% formamide/2X SSPE). The filters were then immersed in fresh hybridization solution containing a $^{32}$P-labeled RNA transcript generated in vitro from the subcloned 146-bp PCR product and incubated for 20 h at 42° C. The filters were washed for 5 min at 20° C. with 2X SSPE/0.2% SDS (twice), and then once with 1X SSPE/0.2% SDS for 30 min at 50° C. Autoradiograms of the filters were made with the aid of an enhancement screen (DuPont Cronex, Wilmington, Del.).

Four independent clones were isolated in this manner, and restriction mapping indicated that all four clones contained common sequences. The largest insert (14 kb) was digested separately with EcoRI and BamHI and the resulting restriction fragments were subcloned into pUCl18 or pBluescript KS+.

These subclones were sequenced by the method of Kraft et al. (Kraft et al, Biotechniques 6: 544–546 (1988)) using a combination of universal and gene-specific primers.

This analysis indicated the presence of two large open reading frames (ORFs) in close proximity to one another; the largest ORF was 4.1 kb long and was immediately downstream from a smaller 2.2-kb ORF.

Comparison of the deduced amino acid sequences of these ORFs to the sequences of animal and yeast ACCase indicated that the 2.2-kb ORF corresponded to the biotin carboxylase domain of ACCase whereas the 4.1-kb ORF contained sequences that could be aligned with the biotin carboxyl carrier protein and carboxyltransferase domains.

The lack of an ORF long enough to encode a 200-kDa polypeptide suggested the presence of an intron between the 2.2kb and 4.1-kbORFs. This possibility was tested by using the PCR procedure to amplify cDNA generated from *C. cryptica* total RNA, utilizing opposing gene-specific primers (JO49 and JO63) that annealed to the cDNA on each side of the predicted intron splicing site. The nucleotide sequence for these two primers is as follows.

| JO49 = TGTCCAATTTGCCCGAA SEQ ID NO:17 |
| JO63 = TAAAGTTGAGATGCCCT SEQ ID NO:18 |

For this procedure, total RNA was isolated from *C. cryptica* cells by a modification of the procedure described by Bascomb et al., Plant Physiol. 83: 75–84 (1987). The modifications included grinding the cells with a mortar and pestle in liquid nitrogen, instead of using a French press, and passing the isolated RNA through a Sigmacell 50 (Sigma; St. Louis, Mo.) column to remove contaminating polysaccharides. Randomly primed synthesis of cDNA and subsequent PCR amplification of ACCase-encoding cDNA using ACCase-specific oligonucleotide primers were carried out by the use of a "GeneAmp" RNA-PCR kit (Perkin Elmer-Cetus). The following PCR thermal cycle was used: Step 1, 94° C. for 2 min; Step 2, 94° C. for 1 min; Step 3, 45° C. for 1 min; Step 4, 2° C./sec to 72° C.; Step 5, 72° C. for 1.5 min; Step 6, repeat steps 2 to 5 for 45 times total; and Step 7, 72° C. for 10 min. PCR products were gel-purified and subcloned into the plasmid pCR 1000 (Invitrogen; San Diego, Calif.). *E. coli* INVαF' cells were transformed with the recombinant plasmids, and plasmid DNA was purified and sequenced as described above.

Sequence analysis of the resulting PCR product confirmed that a 73-bp intron is located approximately 125 bp upstream from the region of the gene that encodes the biotin binding site.

An in-frame translation initiation codon was not present in the first large (2.2-kb) ORF upstream from a region that exhibited strong similarity to ACCase sequences from other species. The 5'-RACE procedure ("Rapid Amplification of cDNA Ends", Frohman et al., Proc. Natl. Acad. Sci. U.S.A. 85: 8998–9002 (1988)) was used to examine this possibility. 5'-RACE was carried out by the use of a kit (BRL-Life Technologies; Gaithersburg, Md.). The primer used for cDNA synthesis was PR10, while JO66 and the kit-supplied anchor primer were used for PCR amplification.

| PR10 = CCAAACGGCATCAACCC SEQ ID NO:19 |
| JO66 = GTTGGCGTAGTTGTTCA. SEQ ID NO:20 |

The following PCR thermal cycle was used: Step 1, 94° C. for 3 min; Step 2, 94° C. for 1 min; Step 3, 45° C. for 1 min; Step 4, 72° C. for 2 min; Step 5, repeat steps 2 to 4 for 40 times total; and Step 6, 72° C. for 10 min. RACE products were digested with SpeI (which cleaves within the anchor primer) and KpnI (which cleaves within the coding region of the ACCase gene), gel-purified, and subcloned into SpeI/KpnI-digested pBluescript KS+. *E. coli* DH5αF' cells were transformed with the recombinant plasmids, and transformants were screened with a labeled DNA probe specific for the 5' end of the ACCase gene. The plasmids containing the largest inserts were sequenced as described above.

The longest RACE product obtained indicated the presence of a 447-bp intron. However, the amplified DNA did not extend in the 5' direction far enough to include a potential initiation codon, although analysis of the genomic sequence indicated that an in-frame ATG codon was present less than 50 bp upstream from the 5' end of the RACE clone. Therefore, a forward PCR primer (PR19) having a sequence of:

| PR19 = GCATTTCCTCACGATAG SEQ ID NO:21 | that annealed slightly upstream from this putative initiation codon was used along with a reverse primer (JO66) that annealed downstream from the 447-bp intron to amplify cDNA generated from total RNA.

An intron-free ACCase gene fragment was obtained by this procedure, and since an in-frame stop codon is present in the cDNA only 15 bp upstream from the putative ATG initiation site, this ATG appears to represent the true translation initiation codon. Removal of the 73-bp and 447-bp introns yields an ORF of nearly 6.3 kb. Additional RNA-PCR experiments using primer pairs bracketing other regions of the ACCase gene have not indicated the presence of other introns.

The DNA sequence from start codon to stop codon including introns is as follows. The introns are represented by being in lower case.

```
ATGGCTCTCCGTAGGGGCCTTTACGCTGCTGCAGCGACTGCCATCTTGGTCACGGCTTCAGT
GACCGCTTTTGgtaagtctgcatttggattgatggttagcattccccacgagcagcatgttg
tgttacgcgttgttgcgtagtgtcagttgtgataattatgatcgacaagaatgggaggactc
tttttgtatcgtttgtagagtgttacactggaccttcgcctaaacacgtttggaggtcctca
catccgcgacgagagctcccacatttcatctacatctctacgtgagcgaatttacgtcacct
ggctattcatttgaggtcccttcctcccacgtgcttccatgttccttagggcgcttaagcat
agttgcacttggagcacttgttgtcaaattgtcgtgtacccgtcactttcgaagcgttattt
ggggttggctggtcctatttaaacagaaattattacgatgtttcgctaacgattctttctct
cattttttaacctacacgaaacagCTCCTCAGCATTCGACATTCACCCCCCAATCGCTCTCG
GCGGCACCCACGCGCAACGTCTTCGGCCAGATCAAAAGCGCCTTCTTCAACCATGATGTTGC
CACCTCTCGAACCATTCTTCACGCCGCGACACTAGATGAAACTGTTCTTTCCGCTTCAGACT
CCGTCGCCAAATCTGTCGAAGACTACGTGAAATCCCGTGGTGGAAATCGCGTCATTCGTAAA
GTCCTCATCGCCAACAACGGCATGGCCGCGACAAAGTCCATCCTCTCCATGCGTCAATGGGC
CTACATGGAATTCGGGGACGAACGTGCCATCCAGTTCGTTGCGATGGCGACTCCCGAGGATT
TGAAGGCGAACGCCGAATTTATTCGCTTGGCGGATTCTTTCGTCGAGGTACCGGGAGGAAAG
AACTTGAACAACTACGCCAACGTCGATGTCATTACCCGCATCGCTAAGGAGCAGGGGGTTGA
TGCCGTTTGGCCTGGATGGGGTCATGCATCTGAGAATCCGAAGCTCCCTAATGCGCTTGACA
AATTGGGAATCAAGTTCATTGGACCAACTGGGCCTGTCATGAGCGTTTTGGGAGACAAGATT
GCTGCGAACATTCTAGCACAGACAGCGAAAGTCCCCTCCATTCCCTGGAGTGGATCCTTTGG
TGGACCAGACGATGGACCCCTTCAGGCGGATCTGACCGAGGAGGGTACTATCCCAATGGAAA
TCTTTAACAAGGGATTAGTAACCTCTGCTGATGAAGCCGTCATTGTGGCGAACAAGATTGGC
TGGGAGAACGGAATCATGATCAAGGCTTCTGAGGGTGGAGGAGGAAAGGGTATACGCTTTGT
CGACAATGAGGCCGACTTACGGAACGCGTTCGTTCAGGTGTCCAATGAAGTGATTGGCTCTC
```

```
CTATTTTCCTCATGCAGTTGTGTAAGAACGCTCGTCACATCGAAGTGCAAATTGTTGGCGAC
CAGCACGGAAATGCTGTAGCGTTGAACGGTCGAGATTGCTCCACTCAGCGTCGCTTCCAGAA
GATCTTCGAGGAAGGTCCTCCGTCCATTGTACCGAAAGAAACATTCCACGAGATGGAACTTG
CGGCTCAACGGTTGACTCAAAACATTGGGTATCAAGGTGCTGGAACTGTGGAATACTTGTAC
AACGCCGCTGACAATAAGTTTTTCTTCCTTGAGTTGAACCCCCGTCTCCAAGTGGAGCATCC
TGTGACTGAAGGAATTACCGGCGCTAATCTTCCTGCCACTCAGCTTCAAGTTGCTATGGGTA
TTCCTCTCTTCAACATTCCTGACATTCGCCGTCTCTATGGAAGAGAGGATGCTTACGGAACG
GATCCCATTGATTTTCTTCAAGAACGTTACCGCGAACTCGACTCTCATGTAATTGCTGCCCG
CATCACTGCTGAAAACCCCGATGAAGGATTCAAACCCACCTCAGGCTCAATTGAGCGAATCA
AATTTCAATCCACCCCAAATGTTTGGGGATATTTCTCTGTTGGTGCTAACGGTGGAATCCAT
GAATTTGCCGACTCTCAGTTTGGCCATCTTTTCGCTAAGGGTCCGAACCGTGAGCAAGCCCG
CAAGGCATTGGTTTTGGCTCTTAAGGAGATGGAAGTGCGCGGAGACATTCGTAACTCTGTTG
AATACCTAGTCAAGTTGCTCGAAACTGAAGCTTTCAAGAAGAACACTATCGACACGTCTTGG
TTAGATGGCATTATTAAGGAGAAGTCCGTTAAAGTTGAGATGCCCTCTCACTTAGTGGTTGT
CGGAGCCGCTGTTTTCAAGGCCTTCGAACATGTTAAGGTGGCCACTGAAGAAGTTAAGGAAT
CGTTTCGAAAAGGACAAGTCTCCACTGCAGGGATTCCAGGCATAAACTCGTTCAACATCGAA
GTTGCGTACTTAGACACGAAGTACCCATTCCACGTAGAACGGATCTCTCCAGATGTTTACAG
GTTTACCTTGGACGGGAACACGATTGATGTGGAAGTTACCCAAACCGCTGAAGGAGCACTTT
TGGCAACCTTTGGAGGAGAGACTCATCGTATCTTTGGTATGGACGAACCACTTGGCCTTCGA
CTGTCATTGGACGGGGCAACTGTCCTAATgtaagttgtctgtccctcgatgtcgctgtttca
tctgtagtcaagtatcctcaccttatgtacttattcgtagGCCAACAATTTTTGACCCCTCT
GAACTCCGCACTGATGTGACTGGAAAGGTTGTTCGTTACCTCCAAGACAATGGAGCAACTGT
TGAAGCGGGCCAGCCCTATGTCGAGGTTGAAGCGATGAAGATGATCATGCCAATCAAGGCTA
CTGAGTCTGGAAAAATTACTCACAACCTAAGTGCTGGTCTGTAATCTCTGCTGGTGACCTT
CTTGCTTCTCTCGAACTTAAGGATCCCTCTAGGGTTAAGAAAATAGAAACTTTTTCGGGCAA
ATTGGACATTATGGAATCGAAGGTTGACTTAGAACCGCAGAAAGCAGTCATGAATGTCCTCT
CTGGGTTCAACTTAGACCCTGAGGCAGTTGCGCAGCAAGCAATTGACAGTGCTACCGACAGC
TCTGCCGCAGCCGATCTTCTTGTCCAAGTATTAGACGAATTCTATCGCGTTGAATCTCAGTT
TGATGGTGTCATCGCTGATGATGTTGTCCGCACTCTCACCAAAGCGAACACCGAGACACTTG
ATGTTGTCATCTCCGAGAACTTGGCCCACCAGCAGCTCAAGAGGCGTAGTCAGCTTCTCCTC
GCTATGATCCGTCAACTTGACACGTTTCAAGACAGATTTGGCAGAGAAGTTCCGGATGCTGT
CATTGAAGCATTGAGTAGGCTTTCTACCTTGAAAGACAAATCTTACGGTGAAATCATTCTTG
CGGCTGAGGAGAGAGTCCGCGAAGCCAAGGTGCCGTCCTTCGAAGTGCGTCGTGCTGATTTG
CGTGCAAAGCTTGCTGACCCGGAGACAGATTTGATTGACCTGAGTAAGAGCTCAACACTCTC
AGCAGGGGTTGACCTTCTCACAAATCTTTTTGATGACGAAGATGAATCTGTCCGCGCTGCTG
CTATGGAAGTATATACTCGCCGTGTCTACCGTACCTACAACATCCCCGAGCTAACTGTTGGA
GTTGAGAATGGCCGCCTCTCATGTAGCTTCTCCTTCCAATTTGCTGATGTCCCGGCGAAAGA
CCGTGTCACCCGCCAAGGGTTCTTCTCAGTTATCGACGACGCTTCAAAGTTCGCGCAACAGC
TTCCTGAGATTCTCAACTCGTTTGGATCAAAGATCGCAGGGGATGCAAGCAAAGAAGGCCCT
GTCAATGTTTTGCAGGTTGGTGCTCTCTCGGGAGATATCAGTATTGAGGACCTCGAGAAAGC
TACTTCCGCTAACAAGGACAAGTTGAATATGCTTGGTGTCCGCACTGTGACGGCTCTTATCC
CAAGGGGAAAGAAGGACCCAAGCTATTATTCATTCCCCCAATGCAGTGGCTTCAAGGAGGAT
CCTCTTCGCAGAGGCATGCGCCCAACCTTTCATCATCTCCTGGAACTCGGACGGCTGGAGGA
AAACTTTGCTCTTGAACGAATTCCTGCAGTTGGACGCAACGTACAGATTTATGTTGGTTCCG
AGAAGACGGCAAGGCGAAATGCAGCTCAAGTTGTTTTCTTGAGAGCTATCTCACATACTCCT
GGCCTAACTACCTTCTCTGGTGCACGCCGAGCTCTTCTCCAGGGGCTTGACGAATTGGAACG
TGCTCAAGCAAACTCAAAGGTCAGTGTCCAGTCATCGTCTCGCATCTACCTTCACTCTCTCC
CAGAACAGTCTGATGCAACTCCCGAGGAGATTGCTAAAGAATTCGAAGGTGTCATTGACAAG
CTAAAGAGTCGATTGGCCCAACGTCTTACGAAACTGCGTTGGGATGAGATTGAAACCAAGGT
TCGCGTGACTGTCCAGGATGAAGACGGTAGTCCCAGGGTTGTGCCTGTACGCCTTGTGGCTT
CTTCAATGCAAGGCGAATGGCTTAAAACATCTGCTTACATTGATCGTCCGGACCCGGTCACT
GGAGTCACCCGTGAACGGTGCGTGATTGGAGAAGGCATTGACGAGGTTTGTGAACTTGAGTC
GTATGACTCTACCAGTACCATCCAAACAAAGCGCTCAATTGCAAGACGTGTGGGATCTACCT
ACGCTTATGACTACCTTGGACTCCTTGAGGTCAGCTTGCTGGAGAATGGGATAAGTATCTC
AGCAGTCTCTCAGGACCGGACACCCCTACCATCCCGTCGAATGTTTTGAAGCTCAAGAGTT
ACTTGAAGGACCTGATGGCGAGCTTGTCACCGGGAAACGTGAAATTGGAACAAATAAGGTTG
GTATGGTTGCATGGGTGGTAACAATGAAAACACCTGAATATCCTGAGGGTCGACAGGTTGTT
GTAATTGTGAACGATGTCACTGTACAAAGTGGTTCATTTGGAGTTGAGGAGGATGAAGTTTT
CTTCAAGGCCTCCAAATATGCTCGCGAAAATAAGCTCCCCCGTGTCTACATTGCGTGCAACT
CTGGTGCTAGAATTGGTTTGGTGGATGATCTCAAGCCAAAGTTCCAGATCAAATTCATTGAT
GAGGCGAGTCCATCTAAGGGTTTTGAGTACCTTTATCTTGATGATGCAACGTACAAATCTCT
TCCAGAAGGGTCGGTAAATGTAAGGAAGGTCCCTGAAGGCTGGGCTATCACTGATATCATTG
GAACGAACGAAGGAATTGGGGTTGAGAACCTTCAAGGAAGTGGCAAAATTGCTGGCGAGACA
TCAAGGGCATATGATGAAATCTTCACCTTGAGTTACGTCACAGGTAGAAGTGTTGGTATTGG
AGCTTACCTTGTCCGTCTCGGCCAGCGTATTATTCAGATGAAACAAGGACCCATGATTCTCA
CAGGCTATGGTGCCCTGAATAAGCTTCTCGGCCGTGAAGTGTCAACTCAAACGACCAACTT
GGTGGTCCTCAAGTCATGTTCCCAAACGGCTGCTCTCATGAAATTGTAGATGATGACCAACA
AGGCATCCAGTCCATTATCCAATGGCTAAGCTTTGTTCCCAAGACAACTGATGCTGTGTCAC
CCGTCCGTGAATGTGCCGACCCTGTCAACAGGGATGTTCAATGGCGCCCTACCCCCACTCCT
TATGATCCACGCCTCATGCTCTCAGGAACTGACGAGGAACTCGGTTTTTTTGACACAGGAAG
CTGGAAGGAATATCTTGCTGGCTGGGGGAAGAGTGTTGTTATTGGCCGCGGTCGCCTTGGTG
GCATTCCTATGGGTGCTATTGCCGTGGAGACCCGGCTTGTTGAAGAGATTATCCCTGCAGAT
CCAGCAGACCCCAACTCCCGCGAAGCTGTCATGCCCCAGGCTGGACAAGTTCTTTTCCCTGA
CTCATCCTACAAGACAGCCCAAGCTCTCCGCGACTTTAATAACGAGGGCCTCCCTGTGATGA
TTTTCGGCAACTGGCGTGGATTTAGTGGTGGAAGTCGTGACATGTCTGGTGAAATCCTCAAA
TTTGGATCCATGATTGTCGATTCACTCCGAGAGTACAAACATCCTATTTACATATACTTCCC
TCCATATGGTGAACTTCGAGGAGGATCGTGGGTTGTGGTGGACCCCACTATCAATGAGGACA
AGATGACCATGTTCTCAGATCCTGATGCTCGTGGTATTCTCGAACCTGCTGGTATTGTA
GAAATCAAGTTCCGCTTGGCAGACCAGCTGAAAGCCATGCACCGCATTGATCCCCAGCTGAA
GATGCTAGATTCAGAGCTTGAGTCGACAGACGACACAGATGTCGCTGCTCAAGAAGCAATCA
```

```
AAGAGCAGATTGCTGCAAGAGAGGAGCTTCTTAAACCCGTCTATCTTCAGGCTGCTACTGAA
TTTGCTGATCTCCACGACAAGACGGGACGGATGAAGGCGAAGGGTGTTATCAAAGAAGCAGT
TCCATGGGCTCGCTCTCGTGAATACTTCTTTTATCTTGCTAAGCGCCGCATTTTTCAAGACA
ACTATGTGTTGCAAATCACTGCTGCTGATCCTTCGTTAGACTCTAAGGCTGCTCTTGAGGTG
TTGAAGAACATGTGCACTGCAGACTGGGATGACAACAAAGCCGTTCTTGACTATTATCTGTC
CAGCGATGGAGACATCACAGCCAAGATTAGCGAGATGAAGAAGGCAGCTATCAAGGCACAGA
TCGAGCAGCTTCAGAAAGCTTTGGAGGGTTGA SEQ ID NO:22
```

The deduced amino acid sequence for the corresponding ACCase protein is:

```
MALRRGLYAAAATAILVTASVTAFAPQHSTFTPQSLSAAPTRNVFGQIKSAFFNHDVATSRT
ILHAATLDETVLSASDSVAKSVEDYVKSRGGNRVIRKVLIANNGMAATKSILSMRQWAYMEF
GDERAIQFVAMATPEDLKANAEFIRLADSFVEVPGGKNLNNYANVDVITRIAKEQGVDAVWP
GWGHASENPKLPNALDKLGIKFIGPTGPVMSVLGDKIAANILAQTAKVPSIPWSGSFGGPDD
GPLQADLTEEGTIPMEIFNKGLVTSADEAVIVANKIGWENGIMIKASEGGGGKGIRFVDNEA
DLRNAFVQVSNEVIGSPIFLMQLCKNARHIEVQIVGDQHGNAVALNGRDCSTQRRFQKIFEE
GPPSIVPKETFHEMELAAQRLTQNIGYQGAGTVEYLYNAADNKFFFLELNPRLQVEHPVTEG
ITGANLPATQLQVAMGIPLFNIPDIRRLYGREDAYGTDPIDFLQERYRELDSHVIAARITAE
NPDEGFKPTSGSIERIKFQSTPNVWGYFSVGANGGIHEFADSQFGHLFAKGPNREQARKALV
LALKEMEVRGDIRNSVEYLVKLLETEAFKKNTIDTSWLDGIIKEKSVKVEMPSHLVVVGAAV
FKAFEHVKVATEEVKESFRKGQVSTAGIPGINSFNIEVAYLDTKYPFHVERISPDVYRFTLD
GNTIDVEVTQTAEGALLATFGGETHRIFGMDEPLGLRLSLDGATVLMPTIFDPSELRTDVTG
KVVRYLQDNGATVEAGQPYVEVEAMKMIMPIKATESGKITHNLSAGSVISAGDLLASLELKD
PSRVKKIETFSGKLDIMESKVDLEPQKAVMNVLSGFNLDPEAVAQQAIDSATDSSAAADLLV
QVLDEFYRVESQFDGVIADDVVRTLTKANTETLDVVISENLAHQQLKRRSQLLLAMIRQLDT
FQDRFGREVPDAVIEALSRLSTLKDKSYGEIILAAEERVREAKVPSFEVRRADLRAKLADPE
TDLIDLSKSSTLSAGVDLLTNLFDDEDESVRAAAMEVYTRRVYRTYNIPELTVGVENGRLSC
SFSFQFADVPAKDRVTRQGFFSVIDDASKFAQQLPEILNSFGSKIAGDASKEGPVNVLQVGA
LSGDISIEDLEKATSANKDKLNMLGVRTVTALIPRGKKDPSYYSFPQCSGFKEDPLRRGMRP
TFHHLLELGRLEENFALERIPAVGRNVQIYVGSEKTARRNAAQVVFLRAISHTPGLTTFSGA
RRALLQGLDELERAQANSKVSVQSSSRIYLHSLPEQSDATPEEIAKEFEGVIDKLKSRLAQR
LTKLRVDEIETKVRVTVQDEDGSPRVVPVRLVASSMQGEWLKTSAYIDRPDPVTGVTRERCV
IGEGIDEVCELESYDSTSTIQTKRSIARRVGSTYAYDYLGLLEVSLLGEWDKYLSSLSGPDT
PTIPSNVFEAQELLEGPDGELVTGKREIGTNKVGMVAWVVTMKTPEYPEGRQVVVIVNDVTV
QSGSFGVEEDEVFFKASKYARENKLPRVYIACNSGARIGLVDDLKPKFQIKFIDEASPSKGF
EYLYLDDATYKSLPEGSVNVRKVPEGWAITDIIGTNEGIGVENLQGSGKIAGETSRAYDEIF
TLSYVTGRSVGIGAYLVRLGQRIIQMKQGPMILTGYGALNKLLGREVYNSNDQLGGPQVMFP
NGCSHEIVDDDQQGIQSIIQWLSFVPKTTDAVSPVRECADPVNRDVQWRPTPTPYDPRLMLS
GTDEELGFFDTGSWKEYLAGWGKSVVIGRGRLGGIPMGAIAVETRLVEKIIPADPADPNSRE
AVMPQAGQVLFPDSSYKTAQALRDFNNEGLPVMIFANWRGFSGGSRDMSGEILKFGSMIVDS
LREYKHPIYIYFPPYGELRGGSWVVVDPTINEDKMTMFSDPDARGGILEPAGIVEIKFRLAD
QLKAMHRIDPQLKMLDSELESTDDTDVAAQEAIKEQIAAREELLKPVYLQAATEFADLHDKT
GRMKAKGVIKEAVPWARSREYFFYLAKRRIFQDNYVLQITAADPSLDSKAALEVLKNMCTAD
WDDNKAVLDYYLSSDGDITAKISEMKKAAIKAQIEQLQKALEG SEQ ID NO:23
```

The experimentally determined amino acid sequences are underlined below. Sequences used for design of the PR1 and PR2 PCR primers are double underlined.

| | |
|---|---:|
| MALRRGLYAAAATAILVTASVTAFAPQHSTFTPQSLSAAPTRNVFGQIKSAFFNHDVATS | 60 |
| RTILHAATLDETVLSASDSVAKSVEDYVKSRGGNRVIRKVLIANNGMAATKSILSMRQWA | 120 |
| YMEFGDERAIQFVAMATPEDLKANAEFIRLADSFVEVPGGKNLNNYANVDVITRIAKEQG | 180 |
| VDAVWPGWGHASENPKLPNALDKLGIKFIGPTGPVMSVLGDKIAANILAQTAKVPSIPWS | 240 |
| GSFGGPDDGPLQADLTEEGTIPMEIFNKGLVTSADEAVIVANKIGWENGIMIKASEGGGG | 300 |
| KGIRFVDNEADLRNAFVQVSNEVIGSPIFLMQLCKNARHIEVQIVGDQHGNAVALNGRDC | 360 |
| STQRRFQKIFEEGPPSIVPKETFHEMELAAQRLTQNIGYQGAGTVEYLYNAADNKFFFLE | 420 |
| LNPRLQVEHPVTEGITGANLPATQLQVAMGIPLFNIPDIRRLYGREDAYGTDPIDFLQER | 480 |
| YRELDSHVIAARITAENPDEGFKPTSGSIERIKFQSTPNVWGYFSVGANGGIHEFADSQF | 540 |
| GHLFAKGPNREQARKALVLALKEMEVRGDIRNSVEYLVKLLETEAFKKNTIDTSWLDGII | 600 |
| KEKSVKVEMPSHLVVVGAAVFKAFEHVKVATEEVKESFRKGQVSTAGIPGINSFNIEVAY | 660 |
| LDTKYPFHVERISPDVYRFTLDGNTIDVEVTQTAEGALLATFGGETHRIFGMDEPLGLRL | 720 |
| SLDGATVLMPTIFDPSELRTDVTGKVVRYLQDNGATVEAGQPYVEVEAMKMIMPIKATES | 780 |
| GKITHNLSAGSVISAGDLLASLELKDPSRVKKIETFSGKLDIMESKVDLEPQKAVMNVLS | 840 |
| GFNLDPEAVAQQAIDSATDSSAAADLLVQVLDEFYRVESQFDGVIADDVVRTLTKANTET | 900 |
| LDVVISENLAHQQLKRRSQLLLAMIRQLDTFQDRFGREVPDAVIEALSRLSTLKDKSYGE | 960 |
| IILAAEERVREAKVPSFEVRRADLRAKLADPETDLIDLSKSSTLSAGVDLLTNLFDDEDE | 1020 |
| SVRAAAMEVYTRRVYRTYNIPELTVGVENGRLSCSFSFQFADVPAKDRVTRQGFFSVIDD | 1080 |
| ASKFAQQLPEILNSFGSKIAGDASKEGPVNVLQVGALSGDISIEDLEKATSANKDKLNML | 1140 |
| GVRTVTALIPRGKKDPSYYSFPQCSGFKEDPLRRGMRPTFHHLLELGRLEENFALERIPA | 1200 |

| | |
|---|---|
| VGRNVQIYVGSEKTARRNAAQVVFLRAISHTPGLTTFSGARRALLQGLDELERAQANSKV | 1260 |
| SVQSSSRIYLHSLPEQSDATPEEIAKEFEGVIDKLKSRLAQRLTKLRVDEIETKVRVTVQ | 1320 |
| DEDGSPRVVPVRLVASSMQGEWLKTSAYIDRPDPVTGVTRERCVIGEGIDEVCELESYDS | 1380 |
| TSTIQTKRSIARRVGSTYAYDYLGLLEVSLLGEWDKYLSSLSGPDTPTIPSNVFEAQELL | 1440 |
| EGPDGELVTGKREIGTNKVGMVAWVVTMKTPEYPEGRQVVVIVNDVTVQSGSFGVEEDEV | 1500 |
| FFKASKYARENKLPRVYIACNSGARIGLVDDLKPKFQIKFIDEASPSKGFEYLYLDDATY | 1560 |
| KSLPEGSVNVRKVPEGWAITDIIGTNEGIGVENLQGSGKIAGETSRAYDEIFTLSYVTGR | 1620 |
| SVGIGAYLVRLGQRIIQMKQGPMILTGYGALNKLLGREVYNSNDQLGGPQVMFPNGCSHE | 1680 |
| IVDDDQQGIQSIIQWLSFVPKTTDAVSPVRECADPVNRDVQWRPTPTPYDPRLMLSGTDE | 1740 |
| ELGFFDTGSWKEYLAGWGKSVVIGRGRLGGIPMGAIAVETRLVEKIIPADPADPNSREAV | 1800 |
| MPQAGGQVLFPDSSYKTAQALRDFNNEGLPVMIFANWRGFSGGSRDMSGEILKFGSMIVDS | 1860 |
| LREYKHPIYIYFPPYGELRGGSWVVVDPTINEDKMTMFSDPDARGGILEPAGIVEIKFRL | 1920 |
| ADQLKAMHRIDPQLKMLDSELESTDDTDVAAQEAIKEQIAAREELLKPVYLQAATEFADL | 1980 |
| HDKTGRMKAKGVIKEAVPWARSREYFFYLAKRRIFQDNYVLQITAADPSLDSKAALEVLK | 2040 |
| NMCTADWDDNKAVLDYYLSSDGDITAKISEMKKAAIKAQIEQLQKALEG | 2089 |
| SEQ ID NO:24 | |

GENE ANALYSIS

The ACCase polypeptide from *C. cryptica* is predicted to be composed of 2089 amino acids and to have an unglycosylated molecular mass of 229,836 daltons before any post translational modification. Previous research has indicated that *C. cryptica* ACCase co-migrates with myosin in SDS-PAGE gels, therefore the molecular mass of the polypeptide was previously estimated to be 185 to 200 kDa (Roessler, Plant Physiol. 92: 73–78 (1990)). This discrepancy is most likely attributable to inaccurate size estimation by SDS-PAGE or by post-translational cleavage of the protein. The N-terminal sequence of the predicted protein has characteristics of a signal sequence, with two positively charged arginine residues within the first five amino acids of the polypeptide, followed by a hydrophobic region (von Heijne, J. Membrane Biol. 115: 195–201 (1990)).

In eukaryotes, signal sequences direct proteins into the endoplasmic reticulum (ER). Signal sequences have also been shown to be necessary for transport of nuclear-encoded proteins into the chloroplasts of diatoms (Bhaya et al., Mol. Gen. Genet. 229: 400–404 (1991)). This observation is consistent with the fact that diatom chloroplasts are completely enclosed by closely expressed ER membranes (Gibbs, J. Cell. Sci. 35: 253–266 (1979)). Fatty acid biosynthesis occurs primarily in the plastids of higher plants (Harwood, Ann. Rev. Plant Physiol. Plant Mol. Biol. 39: 101–138 (1988)). It is assumed that ACCase is located in the chloroplasts of diatoms, and therefore a signal sequence may be necessary for chloroplast targeting. Alternatively, it is possible that the cloned gene of the present invention is an ER-localized isoform of ACCase.

Diatoms produce substantial quantities of $C_{20}$ and $C_{22}$ fatty acids (primarily eicosapentaenoic acid and docosahexaenoic acid). In higher plants and diatoms, elongation of fatty acids to lengths greater than 18 carbons occurs within the ER, implicating the need for malonyl-CoA in this cellular compartment. (Harwood, Ann. Rev. Plant Physiol. Plant Mol. Biol. 39: 101–138 (1988); Schreiner et al., Plant. Physiol. 96(S): 14 (1991)), However, malonyl-CoA is not able to pass through the chloroplast envelope, and therefore either an additional ACCase isoform exists outside of the chloroplast or there must be an alternative means of malonyl-CoA synthesis or transport. Accordingly, the present invention encompasses expressing the ACCase gene with and/or without a signal sequence to transport the enzyme into a plastid.

It should be noted, however, that the ACCase which was used in the Example for amino acid sequencing (and subsequent PCR primer design) was by far the most abundant ACCase in *C. cryptica* under the purification/assay conditions that were employed. It therefore appears likely that the cloned gene sequence recited above is for an ACCase that is responsible for chloroplastic fatty acid biosynthesis.

In order to test for the possible presence of compartment-specific ACCase isoforms, Southern blots of *C. cryptica* total DNA that had been digested with five different restriction enzymes were probed with the ACCase-encoding 146-bp PCR product described above. Total DNA (10 µg) isolated from *C. cryptica* was digested for 18 h at 37° C. with 40 units or either EcoRI, EcoRV, HindIII, PstI, or SacI. Agarose gel electrophoresis and alkaline blotting were carried out under standard conditions (Sambrook et al., Molecular Cloning: A Laboratory Manual, 2nd Ed., Cold Spring Harbor Laboratory Press, N.Y. (1989)). The prehybridization, hybridization, and washing steps were performed as described above for genomic library screening. The results suggest the presence of a single isoform. If isoforms do exist, the sequences of the genes must be different enough in this region to prevent cross-hybridization under the conditions utilized. The fact that ACCase must pass through the ER in order to enter the chloroplast raises the possibility that this one isoform could actually be functional in two distinct cellular compartments.

Several other features of the predicted ACCase primary structure warrant discussion. Two computer alignment programs (MACAW and ALIGN) were used to search for regions of the ACCase amino acid sequences from rat, yeast, and *C. cryptica* that were similar. The MACAW program was developed by Schuler et al. (Schuler et al., Proteins Struct. Funct. Genet. 9: 180–190 (1991)) and the ALIGN program (Scientific and Educational Software, State Line, Pa.) is based on the method of Myers and Miller (Myenrs et al., CABIOS 4: 11–17 (1988)). Calculations for "% identity" used the ALIGN program with default penalties for mismatches, gap introductions, and gap elongation.

In the region of the *C. cryptica* ACCase polypeptide that includes the biotin carboxylase domain (residues 1 to 620), there is 52% and 50% identity with the rat and yeast ACCase sequences, respectively. Likewise, the region of *C. cryptica* ACCase that includes the carboxyltransferase domain (residues 1426 to 2089) exhibits 50% identity with both the rat and yeast sequences. Therefore, considerable variations can be made to the sequence while maintaining the biological activity.

Figure 1B:
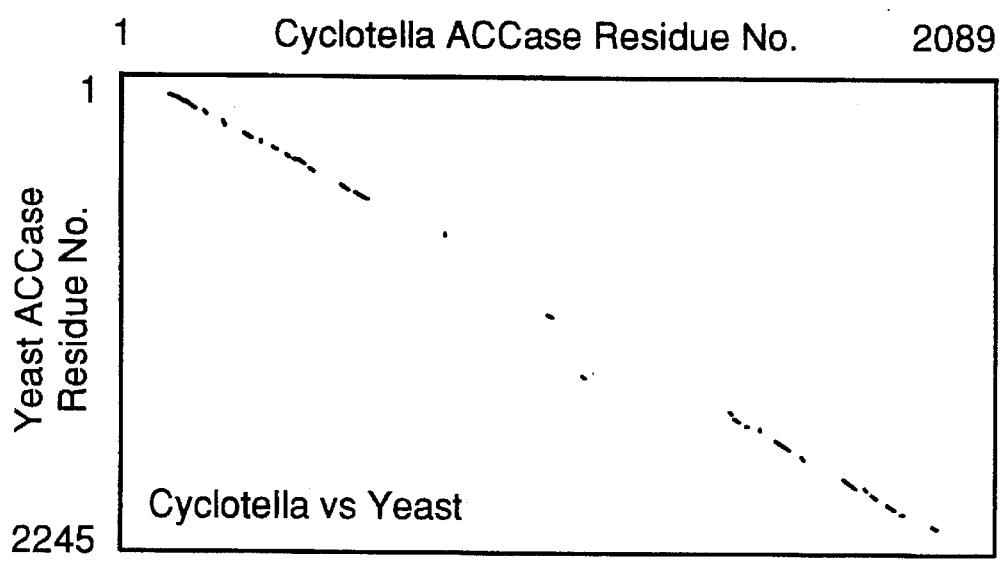

On the other hand, there is less sequence conservation in the middle region of the protein among any of these ACCase enzymes (30% identity, with the bulk of this similarity occurring in the vicinity of the biotin binding site). This relationship is graphically demonstrated by the homology plots of FIG. 1. This middle region, which includes portions of the biotin carboxyl carrier protein domain, may be little more than a spacer region that facilitates the physical movement of the carboxylated biotin from the biotin carboxylase active site to the carboxyltransferase active site. In this case, a high degree of sequence conservation would not be expected.

Variants of ACCase may be constructed using the principal of maintaining a high degree of homology in the conserved regions and making any of a large number of changes to the regions which are not conserved.

Unlike the multifunctional fatty acid synthase enzyme from animals and yeast (McCarthy et al., Trends Biochem. Sciences 9: 60–63 (1984)), the domains of ACCases from animals, yeast, and *C. cryptica* are in the same relative positions. This suggests either that an early, single gene fusion event occurred in the course of evolution or that there is a strict, functional requirement for this particular arrangement.

The presumed biotin binding site is a lysine residue (No. 770) that is flanked by two methionines. This tripeptide has been observed in every biotin-containing enzyme for which the amino acid sequence is known. Another characteristic of this region is the presence of one or more proline residues approximately 25 to 30 positions upstream from the biotin binding site that are believed to form a hinge region for carboxybiotin movement (Samols et al., J. Biol. Chem. 263: 6461–6464 (1988)). Proline residues are also found at this location in *C. cryptica* ACCase, although they are displaced five to six residues toward the N-terminus in *C. cryptica* ACCase relative to yeast and animal ACCases.

Regions of the carboxyltransferase subunit from *E. coli* that are proposed to be involved in acetyl-CoA and carboxybiotin binding have been identified (Li et al., J. Biol. Chem. 267: 16841–16847, (1992)). Another highly conserved region is the putative ATP-binding site of the biotin carboxylase domain/subunit. A comparison of the amino acid sequence in these areas of ACCase from *C. cryptica*, yeast, rat and *E. coli* is shown in FIG. 2. Accordingly, while the nucleotide sequence may be changed significantly, careful selection of any variation in the amino acid sequence in these regions is needed. Additionally, changes in these areas may be desirable for making changes in the enzyme's activity or properties.

The foregoing description of the specific embodiments reveal the general nature of the invention so that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

All references mentioned in this application are incorporated by reference.

SEQUENCE LISTING ( 1 ) GENERAL INFORMATION:

( i i i ) NUMBER OF SEQUENCES: 25

( 2 ) INFORMATION FOR SEQ ID NO:1:

( i ) SEQUENCE CHARACTERISTICS:
        ( A ) LENGTH: 51 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( x i ) SEQUENCE DESCRIPTION: SEQ ID NO:1:

```
Gly  Arg  Gln  Val  Val  Val  Ile  Val  Asn  Asp  Val  Thr  Val  Gln  Ser  Gly
 1              5                         10                        15

Ser  Phe  Gly  Val  Glu  Glu  Asp  Glu  Val  Phe  Phe  Lys  Ala  Ser  Lys  Tyr
              20                        25                        30

Ala  Arg  Glu  Asn  Lys  Leu  Pro  Arg  Val  Tyr  Ile  Ala  Cys  Asn  Ser  Gly
              35                        40                        45

Ala  Arg  Ile
      50
```

( 2 ) INFORMATION FOR SEQ ID NO:2:

( i ) SEQUENCE CHARACTERISTICS:
        ( A ) LENGTH: 51 amino acids
        ( B ) TYPE: amino acid (C) STRANDEDNESS: single
(D) TOPOLOGY: linear (ii) MOLECULE TYPE: protein (iii) HYPOTHETICAL: NO (iv) ANTI-SENSE: NO (v) FRAGMENT TYPE: internal (xi) SEQUENCE DESCRIPTION: SEQ ID NO:2:

| Gly | Arg | Gln | Phe | Val | Val | Val | Ala | Asn | Asp | Ile | Thr | Phe | Lys | Ile | Gly |
|---|---|---|---|---|---|---|---|---|---|---|---|---|---|---|---|
| 1 | | | | 5 | | | | | 10 | | | | | 15 | |

| Ser | Phe | Gly | Pro | Gln | Glu | Asp | Glu | Phe | Phe | Asn | Lys | Val | Thr | Glu | Tyr |
|---|---|---|---|---|---|---|---|---|---|---|---|---|---|---|---|
| | | | 20 | | | | | 25 | | | | | 30 | | |

| Ala | Arg | Lys | Arg | Gly | Ile | Pro | Arg | Ile | Tyr | Leu | Ala | Ala | Asn | Ser | Gly |
|---|---|---|---|---|---|---|---|---|---|---|---|---|---|---|---|
| | | 35 | | | | | 40 | | | | | 45 | | | |

| Ala | Arg | Ile |
|---|---|---|
| | | 50 |

(2) INFORMATION FOR SEQ ID NO:3:

(i) SEQUENCE CHARACTERISTICS:
(A) LENGTH: 51 amino acids
(B) TYPE: amino acid
(C) STRANDEDNESS: single
(D) TOPOLOGY: linear (ii) MOLECULE TYPE: protein (iii) HYPOTHETICAL: NO (iv) ANTI-SENSE: NO (v) FRAGMENT TYPE: internal (xi) SEQUENCE DESCRIPTION: SEQ ID NO:3:

| Gly | Arg | Asp | Val | Ile | Val | Ile | Gly | Asn | Asp | Ile | Thr | Tyr | Arg | Ile | Gly |
|---|---|---|---|---|---|---|---|---|---|---|---|---|---|---|---|
| 1 | | | | 5 | | | | | 10 | | | | | 15 | |

| Ser | Phe | Gly | Pro | Gln | Glu | Asp | Leu | Leu | Phe | Leu | Arg | Ala | Ser | Glu | Leu |
|---|---|---|---|---|---|---|---|---|---|---|---|---|---|---|---|
| | | | 20 | | | | | 25 | | | | | 30 | | |

| Ala | Arg | Ala | Glu | Gly | Ile | Pro | Arg | Ile | Tyr | Val | Ala | Ala | Asn | Ser | Gly |
|---|---|---|---|---|---|---|---|---|---|---|---|---|---|---|---|
| | | 35 | | | | | 40 | | | | | 45 | | | |

| Ala | Arg | Ile |
|---|---|---|
| | | 50 |

(2) INFORMATION FOR SEQ ID NO:4:

(i) SEQUENCE CHARACTERISTICS:
(A) LENGTH: 51 amino acids
(B) TYPE: amino acid
(C) STRANDEDNESS: single
(D) TOPOLOGY: linear (ii) MOLECULE TYPE: protein (iii) HYPOTHETICAL: NO (iv) ANTI-SENSE: NO (v) FRAGMENT TYPE: internal (xi) SEQUENCE DESCRIPTION: SEQ ID NO:4:

| Gly | Met | Pro | Val | Val | Ala | Ala | Ala | Phe | Glu | Phe | Ala | Phe | Met | Gly | Gly |
|---|---|---|---|---|---|---|---|---|---|---|---|---|---|---|---|
| 1 | | | | 5 | | | | | 10 | | | | | 15 | |

| Ser | Met | Gly | Ser | Val | Val | Gly | Ala | Arg | Phe | Val | Arg | Ala | Val | Glu | Gln |
|---|---|---|---|---|---|---|---|---|---|---|---|---|---|---|---|
| | | | 20 | | | | | 25 | | | | | 30 | | |

```
        Ala  Leu  Glu  Asp  Asn  Cys  Pro  Leu  Ile  Cys  Phe  Ser  Ala  Ser  Gly  Gly
                   35                      40                      45

Ala  Arg  Met
                   50
```

( 2 ) INFORMATION FOR SEQ ID NO:5:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( x i ) SEQUENCE DESCRIPTION: SEQ ID NO:5:

```
        Gly  Lys  Ser  Val  Val  Ile  Gly  Arg  Gly  Arg  Leu  Gly  Gly  Ile  Pro  Met
        1               5                        10                      15

Gly  Ala  Ile  Ala
                    20
```

( 2 ) INFORMATION FOR SEQ ID NO:6:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( x i ) SEQUENCE DESCRIPTION: SEQ ID NO:6:

```
        Ala  Lys  Gly  Val  Val  Val  Gly  Arg  Ala  Arg  Leu  Gly  Gly  Ile  Pro  Leu
        1               5                        10                      15

Gly  Val  Ile  Gly
                    20
```

( 2 ) INFORMATION FOR SEQ ID NO:7:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( x i ) SEQUENCE DESCRIPTION: SEQ ID NO:7:

```
        Ala  Gln  Thr  Val  Val  Val  Gly  Arg  Ala  Arg  Leu  Gly  Gly  Ile  Pro  Val
        1               5                        10                      15

Gly  Val  Val  Ala
```

2 0

( 2 ) INFORMATION FOR SEQ ID NO:8:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( x i ) SEQUENCE DESCRIPTION: SEQ ID NO:8:

Asp Lys Ala Ile Val Gly Gly Ile Ala Arg Leu Asp Gly Arg Pro Val
1               5                   10                  15
Met Ile Ile Gly
            20

( 2 ) INFORMATION FOR SEQ ID NO:9:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( x i ) SEQUENCE DESCRIPTION: SEQ ID NO:9:

Glu Asn Gly Ile Met Ile Lys Ala Ser Glu Gly Gly Gly Gly Lys Gly
1               5                   10                  15
Ile Arg Phe Val Asp
            20

( 2 ) INFORMATION FOR SEQ ID NO:10:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( x i ) SEQUENCE DESCRIPTION: SEQ ID NO:10:

Gly Phe Pro Val Met Ile Lys Ala Ser Glu Gly Gly Gly Gly Lys Gly
1               5                   10                  15
Ile Arg Gln Val Glu
            20

( 2 ) INFORMATION FOR SEQ ID NO:11:

( i ) SEQUENCE CHARACTERISTICS:
( A ) LENGTH: 21 amino acids
( B ) TYPE: amino acid
( C ) STRANDEDNESS: single
( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( x i ) SEQUENCE DESCRIPTION: SEQ ID NO:11:

```
Gly Tyr Pro Asx Met Ile Lys Ala Ser Glu Gly Gly Gly Gly Lys Gly
 1               5                  10                      15
Ile Arg Lys Asx Asn
            20
```

( 2 ) INFORMATION FOR SEQ ID NO:12:

( i ) SEQUENCE CHARACTERISTICS:
( A ) LENGTH: 21 amino acids
( B ) TYPE: amino acid
( C ) STRANDEDNESS: single
( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( x i ) SEQUENCE DESCRIPTION: SEQ ID NO:12:

```
Gly Tyr Pro Val Ile Ile Lys Ala Ser Gly Gly Gly Gly Gly Arg Gly
 1               5                  10                      15
Met Arg Val Val Arg
            20
```

( 2 ) INFORMATION FOR SEQ ID NO:13:

( i ) SEQUENCE CHARACTERISTICS:
( A ) LENGTH: 20 bases
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:13:

TTYGTNTGGA AYGARGCNGA                    20

( 2 ) INFORMATION FOR SEQ ID NO: 14:

( i ) SEQUENCE CHARACTERISTICS:
( A ) LENGTH: 20 bases
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO (x i) SEQUENCE DESCRIPTION: SEQ ID NO:14:

ACNGCRTTNC CRTGYTGRTC                                           20

(2) INFORMATION FOR SEQ ID NO:15:

(i) SEQUENCE CHARACTERISTICS:
        (A) LENGTH: 35 amino acids
        (B) TYPE: amino acid
        (C) STRANDEDNESS: single
        (D) TOPOLOGY: linear (i i) MOLECULE TYPE: protein (i i i) HYPOTHETICAL: NO (i v) ANTI-SENSE: NO (v) FRAGMENT TYPE: internal (x i) SEQUENCE DESCRIPTION: SEQ ID NO:15:

```
Leu  Arg  Asn  Ala  Phe  Val  Gln  Val  Ser  Asn  Glu  Val  Ile  Gly  Ser  Pro
1                   5                        10                       15
Ile  Phe  Leu  Met  Gln  Leu  Cys  Lys  Asn  Ala  Arg  His  Ile  Glu  Val  Gln
               20                       25                       30
Ile  Val  Gly
          35
```

(2) INFORMATION FOR SEQ ID NO:16:

(i) SEQUENCE CHARACTERISTICS:
        (A) LENGTH: 35 amino acids
        (B) TYPE: amino acid
        (C) STRANDEDNESS: single
        (D) TOPOLOGY: linear (i i) MOLECULE TYPE: protein (i i i) HYPOTHETICAL: NO (i v) ANTI-SENSE: NO (v) FRAGMENT TYPE: internal (x i) SEQUENCE DESCRIPTION: SEQ ID NO:16:

```
Phe  Pro  Asn  Leu  Phe  Arg  Gln  Val  Gln  Ala  Glu  Val  Pro  Gly  Ser  Pro
1                   5                        10                       15
Ile  Phe  Val  Met  Arg  Leu  Ala  Lys  Gln  Ser  Arg  His  Leu  Glu  Val  Gln
               20                       25                       30
Ile  Leu  Ala
          35
```

(2) INFORMATION FOR SEQ ID NO:17:

(i) SEQUENCE CHARACTERISTICS:
        (A) LENGTH: 17 bases
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:17:

TGTCCAATTT GCCCGAA                                              17

( 2 ) INFORMATION FOR SEQ ID NO:18:

( i ) SEQUENCE CHARACTERISTICS:
        ( A ) LENGTH: 17 bases
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:18:

TAAAGTTGAG ATGCCCT            17

( 2 ) INFORMATION FOR SEQ ID NO:19:

( i ) SEQUENCE CHARACTERISTICS:
        ( A ) LENGTH: 17 bases
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:19:

CCAAACGGCA TCAACCC            17

( 2 ) INFORMATION FOR SEQ ID NO:20:

( i ) SEQUENCE CHARACTERISTICS:
        ( A ) LENGTH: 17 bases
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:20:

GTTGGCGTAG TTGTTCA            17

( 2 ) INFORMATION FOR SEQ ID NO:21:

( i ) SEQUENCE CHARACTERISTICS:
        ( A ) LENGTH: 17 bases
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:21:

GCATTTCCTC ACGATAG            17

( 2 ) INFORMATION FOR SEQ ID NO:22:

( i ) SEQUENCE CHARACTERISTICS:

5,559,220

(A) LENGTH: 6790 bases
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:22:

```
ATGGCTCTCC GTAGGGGCCT TTACGCTGCT GCAGCGACTG CCATCTTGGT CACGGCTTCA    60
GTGACCGCTT TTGGTAAGTC TGCATTTGGA TTGATGGTTA GCATTCCCCA CGAGCAGCAT   120
GTTGTGTTAC GCGTTGTTGC GTAGTGTCAG TTGTGATAAT TATGATCGAC AAGAATGGGA   180
GGACTCTTTT TGTATCGTTT GTAGAGTGTT ACACTGGACC TTCGCCTAAA CACGTTTGGA   240
GGTCCTCACA TCCGCGACGA GAGCTCCCAC ATTTCATCTA CATCTCTACG TGAGCGAATT   300
TACGTCACCT GGCTATTCAT TTGAGGTCCC TTCCTCCCAC GTGCTTCCAT GTTCCTTAGG   360
GCGCTTAAGC ATAGTTGCAC TTGGAGCACT TGTTGTCAAA TTGTCGTGTA CCCGTCACTT   420
TCGAAGCGTT ATTTGGGGTT GGCTGGTCCT ATTTAAACAG AAATTATTAC GATGTTTCGC   480
TAACGATTCT TTCTCTCATT TTTTAACCTA CACGAAACAG CTCCTCAGCA TTCGACATTC   540
ACCCCCCAAT CGCTCTCGGC GGCACCCACG CGCAACGTCT TCGGCCAGAT CAAAAGCGCC   600
TTCTTCAACC ATGATGTTGC CACCTCTCGA ACCATTCTTC ACGCCGCGAC ACTAGATGAA   660
ACTGTTCTTT CCGCTTCAGA CTCCGTCGCC AAATCTGTCG AAGACTACGT GAAATCCCGT   720
GGTGGAAATC GCGTCATTCG TAAAGTCCTC ATCGCCAACA ACGGCATGGC CGCGACAAAG   780
TCCATCCTCT CCATGCGTCA ATGGGCCTAC ATGGAATTCG GGACGAACG TGCCATCCAG   840
TTCGTTGCGA TGGCGACTCC CGAGGATTTG AAGGCGAACG CCGAATTTAT TCGCTTGGCG   900
GATTCTTTCG TCGAGGTACC GGGAGGAAAG AACTTGAACA ACTACGCCAA CGTCGATGTC   960
ATTACCCGCA TCGCTAAGGA GCAGGGGGTT GATGCCGTTT GGCCTGGATG GGTCATGCA  1020
TCTGAGAATC CGAAGCTCCC TAATGCGCTT GACAAATTGG GAATCAAGTT CATTGGACCA  1080
ACTGGGCCTG TCATGAGCGT TTTGGGAGAC AAGATTGCTG CGAACATTCT AGCACAGACA  1140
GCGAAAGTCC CCTCCATTCC CTGGAGTGGA TCCTTTGGTG GACCAGACGA TGGACCCCTT  1200
CAGGCGGATC TGACCGAGGA GGGTACTATC CCAATGGAAA TCTTTAACAA GGGATTAGTA  1260
ACCTCTGCTG ATGAAGCCGT CATTGTGGCG AACAAGATTG GCTGGGAGAA CGGAATCATG  1320
ATCAAGGCTT CTGAGGGTGG AGGAGGAAAG GGTATACGCT TTGTCGACAA TGAGGCCGAC  1380
TTACGGAACG CGTTCGTTCA GGTGTCCAAT GAAGTGATTG CTCTCCTAT TTTCCTCATG  1440
CAGTTGTGTA AGAACGCTCG TCACATCGAA GTGCAAATTG TTGGCGACCA GCACGGAAAT  1500
GCTGTAGCGT TGAACGGTCG AGATTGCTCC ACTCAGCGTC GCTTCCAGAA GATCTTCGAG  1560
GAAGGTCCTC CGTCCATTGT ACCGAAAGAA ACATTCCACG AGATGGAACT TGCGGCTCAA  1620
CGGTTGACTC AAAACATTGG GTATCAAGGT GCTGGAACTG TGGAATACTT GTACAACGCC  1680
GCTGACAATA AGTTTTTCTT CCTTGAGTTG AACCCCCGTC TCCAAGTGGA GCATCCTGTG  1740
ACTGAAGGAA TTACCGGCGC TAATCTTCCT GCCACTCAGC TTCAAGTTGC TATGGGTATT  1800
CCTCTCTTCA ACATTCCTGA CATTCGCCGT CTCTATGGAA GAGAGGATGC TTACGGAACG  1860
GATCCCATTG ATTTTCTTCA AGAACGTTAC CGCGAACTCG ACTCTCATGT AATTGCTGCC  1920
CGCATCACTG CTGAAAACCC CGATGAAGGA TTCAAACCCA CCTCAGGCTC AATTGAGCGA  1980
ATCAAATTTC AATCCACCCC AAATGTTTGG GGATATTTCT CTGTTGGTGC TAACGGTGGA  2040
```

-continued

```
ATCCATGAAT TTGCCGACTC TCAGTTTGGC CATCTTTTCG CTAAGGGTCC GAACCGTGAG 2100
CAAGCCCGCA AGGCATTGGT TTTGGCTCTT AAGGAGATGG AAGTGCGCGG AGACATTCGT 2160
AACTCTGTTG AATACCTAGT CAAGTTGCTC GAAACTGAAG CTTTCAAGAA GAACACTATC 2220
GACACGTCTT GGTTAGATGG CATTATTAAG GAGAAGTCCG TTAAAGTTGA GATGCCCTCT 2280
CACTTAGTGG TTGTCGGAGC CGCTGTTTTC AAGGCCTTCG AACATGTTAA GGTGGCCACT 2340
GAAGAAGTTA AGGAATCGTT TCGAAAAGGA CAAGTCTCCA CTGCAGGGAT TCCAGGCATA 2400
AACTCGTTCA ACATCGAAGT TGCGTACTTA GACACGAAGT ACCCATTCCA CGTAGAACGG 2460
ATCTCTCCAG ATGTTTACAG GTTTACCTTG GACGGGAACA CGATTGATGT GGAAGTTACC 2520
CAAACCGCTG AAGGAGCACT TTTGGCAACC TTTGGAGGAG AGACTCATCG TATCTTTGGT 2580
ATGGACGAAC CACTTGGCCT TCGACTGTCA TTGGACGGGG CAACTGTCCT AATGTAAGTT 2640
GTCTGTCCCT CGATGTCGCT GTTTCATCTG TAGTCAAGTA TCCTCACCTT ATGTACTTAT 2700
TCGTAGGCCA ACAATTTTTG ACCCCTCTGA ACTCCGCACT GATGTGACTG GAAAGGTTGT 2760
TCGTTACCTC CAAGACAATG GAGCAACTGT TGAAGCGGGC CAGCCCTATG TCGAGGTTGA 2820
AGCGATGAAG ATGATCATGC CAATCAAGGC TACTGAGTCT GGAAAAATTA CTCACAACCT 2880
AAGTGCTGGA TCTGTAATCT CTGCTGGTGA CCTTCTTGCT TCTCTCGAAC TTAAGGATCC 2940
CTCTAGGGTT AAGAAAATAG AAACTTTTTC GGGCAAATTG GACATTATGG AATCGAAGGT 3000
TGACTTAGAA CCGCAGAAAG CAGTCATGAA TGTCCTCTCT GGGTTCAACT TAGACCCTGA 3060
GGCAGTTGCG CAGCAAGCAA TTGACAGTGC TACCGACAGC TCTGCCGCAG CCGATCTTCT 3120
TGTCCAAGTA TTAGACGAAT CTATCGCGT TGAATCTCAG TTTGATGGTG TCATCGCTGA 3180
TGATGTTGTC CGCACTCTCA CCAAAGCGAA CACCGAGACA CTTGATGTTG TCATCTCCGA 3240
GAACTTGGCC CACCAGCAGC TCAAGAGGCG TAGTCAGCTT CTCCTCGCTA TGATCCGTCA 3300
ACTTGACACG TTTCAAGACA GATTTGGCAG AGAAGTTCCG GATGCTGTCA TTGAAGCATT 3360
GAGTAGGCTT TCTACCTTGA AAGACAAATC TTACGGTGAA ATCATTCTTG CGGCTGAGGA 3420
GAGAGTCCGC GAAGCCAAGG TGCCGTCCTT CGAAGTGCGT CGTGCTGATT TGCGTGCAAA 3480
GCTTGCTGAC CCGGAGACAG ATTTGATTGA CCTGAGTAAG AGCTAACAC TCTCAGCAGG 3540
GGTTGACCTT CTCACAAATC TTTTTGATGA CGAAGATGAA TCTGTCCGCG CTGCTGCTAT 3600
GGAAGTATAT ACTCGCCGTG TCTACCGTAC CTACAACATC CCCGAGCTAA CTGTTGGAGT 3660
TGAGAATGGC CGCCTCTCAT GTAGCTTCTC CTTCCAATTT GCTGATGTCC CGGCGAAAGA 3720
CCGTGTCACC CGCCAAGGGT TCTTCTCAGT TATCGACGAC GCTTCAAAGT TCGCGCAACA 3780
GCTTCCTGAG ATTCTCAACT CGTTTGGATC AAAGATCGCA GGGGATGCAA GCAAAGAAGG 3840
CCCTGTCAAT GTTTTGCAGG TTGGTGCTCT CTCGGGAGAT ATCAGTATTG AGGACCTCGA 3900
GAAAGCTACT TCCGCTAACA AGGACAAGTT GAATATGCTT GGTGTCCGCA CTGTGACGGC 3960
TCTTATCCCA AGGGGAAAGA AGGACCCAAG CTATTATTCA TTCCCCCAAT GCAGTGGCTT 4020
CAAGGAGGAT CCTCTTCGCA GAGGCATGCG CCCAACCTTT CATCATCTCC TGGAACTCGG 4080
ACGGCTGGAG GAAAACTTTG CTCTTGAACG AATTCCTGCA GTTGGACGCA ACGTACAGAT 4140
TTATGTTGGT TCCGAGAAGA CGGCAAGGCG AAATGCAGCT CAAGTTGTTT CTTGAGAGC 4200
TATCTCACAT ACTCCTGGCC TAACTACCTT CTCTGGTGCA CGCCGAGCTC TTCTCCAGGG 4260
GCTTGACGAA TTGGAACGTG CTCAAGCAAA CTCAAAGGTC AGTGTCCAGT CATCGTCTCG 4320
CATCTACCTT CACTCTCTCC CAGAACAGTC TGATGCAACT CCCGAGGAGA TTGCTAAAGA 4380
ATTCGAAGGT GTCATTGACA AGCTAAAGAG TCGATTGGCC CAACGTCTTA CGAAACTGCG 4440
```

```
TGTGGATGAG ATTGAAACCA AGGTTCGCGT GACTGTCCAG GATGAAGACG GTAGTCCCAG    4500
GGTTGTGCCT GTACGCCTTG TGGCTTCTTC AATGCAAGGC GAATGGCTTA AAACATCTGC    4560
TTACATTGAT CGTCCGGACC CGGTCACTGG AGTCACCCGT GAACGGTGCG TGATTGGAGA    4620
AGGCATTGAC GAGGTTTGTG AACTTGAGTC GTATGACTCT ACCAGTACCA TCCAAACAAA    4680
GCGCTCAATT GCAAGACGTG TGGGATCTAC CTACGCTTAT GACTACCTTG GACTCCTTGA    4740
GGTCAGCTTG CTTGGAGAAT GGGATAAGTA TCTCAGCAGT CTCTCAGGAC CGGACACCCC    4800
TACCATCCCG TCGAATGTTT TTGAAGCTCA AGAGTTACTT GAAGGACCTG ATGGCGAGCT    4860
TGTCACCGGG AAACGTGAAA TTGGAACAAA TAAGGTTGGT ATGGTTGCAT GGGTGGTAAC    4920
AATGAAAACA CCTGAATATC CTGAGGGTCG ACAGGTTGTT GTAATTGTGA ACGATGTCAC    4980
TGTACAAAGT GGTTCATTTG GAGTTGAGGA GGATGAAGTT TTCTTCAAGG CCTCCAAATA    5040
TGCTCGCGAA AATAAGCTCC CCGTGTCTA CATTGCGTGC AACTCTGGTG CTAGAATTGG    5100
TTTGGTGGAT GATCTCAAGC CAAAGTTCCA GATCAAATTC ATTGATGAGG CGAGTCCATC    5160
TAAGGGTTTT GAGTACCTTT ATCTTGATGA TGCAACGTAC AAATCTCTTC CAGAAGGGTC    5220
GGTAAATGTA AGGAAGGTCC CTGAAGGCTG GGCTATCACT GATATCATTG GAACGAACGA    5280
AGGAATTGGG GTTGAGAACC TTCAAGGAAG TGGCAAAATT GCTGGCGAGA CATCAAGGGC    5340
ATATGATGAA ATCTTCACCT TGAGTTACGT CACAGGTAGA AGTGTTGGTA TTGGAGCTTA    5400
CCTTGTCCGT CTCGGCCAGC GTATTATTCA GATGAAACAA GGACCCATGA TTCTCACAGG    5460
CTATGGTGCC CTGAATAAGC TTCTCGGCCG TGAAGTGTAC AACTCAAACG ACCAACTTGG    5520
TGGTCCTCAA GTCATGTTCC CAAACGGCTG CTCTCATGAA ATTGTAGATG ATGACCAACA    5580
AGGCATCCAG TCCATTATCC AATGGCTAAG CTTTGTTCCC AAGACAACTG ATGCTGTGTC    5640
ACCCGTCCGT GAATGTGCCG ACCCTGTCAA CAGGGATGTT CAATGGCGCC CTACCCCCAC    5700
TCCTTATGAT CCACGCCTCA TGCTCTCAGG AACTGACGAG GAACTCGGTT TTTTTGACAC    5760
AGGAAGCTGG AAGGAATATC TTGCTGGCTG GGGGAAGAGT GTTGTTATTG CCACGGTCG    5820
CCTTGGTGGC ATTCCTATGG GTGCTATTGC CGTGGAGACC CGGCTTGTTG AGAAGATTAT    5880
CCCTGCAGAT CCAGCAGACC CCAACTCCCG CGAAGCTGTC ATGCCCCAGG CTGGACAAGT    5940
TCTTTTCCCT GACTCATCCT ACAAGACAGC CCAAGCTCTC CGCGACTTTA ATAACGAGGG    6000
CCTCCCTGTG ATGATTTTCG GCAACTGGCG TGGATTTAGT GGTGGAAGTC GTGACATGTC    6060
TGGTGAAATC CTCAAATTTG GATCCATGAT TGTCGATTCA CTCCGAGAGT ACAAACATCC    6120
TATTTACATA TACTTCCCTC CATATGGTGA ACTTCGAGGA GGATCGTGGG TTGTGGTGGA    6180
CCCCACTATC AATGAGGACA AGATGACCAT GTTCTCAGAT CCTGATGCTC GTGGTGGTAT    6240
TCTCGAACCT GCTGGTATTG TAGAAATCAA GTTCCGCTTG GCAGACCAGC TGAAAGCCAT    6300
GCACCGCATT GATCCCCAGC TGAAGATGCT AGATTCAGAG CTTGAGTCGA CAGACGACAC    6360
AGATGTCGCT GCTCAAGAAG CAATCAAAGA GCAGATTGCT GCAAGAGAGG AGCTTCTTAA    6420
ACCCGTCTAT CTTCAGGCTG CTACTGAATT TGCTGATCTC CACGACAAGA CGGGACGGAT    6480
GAAGGCGAAG GGTGTTATCA AGAAGCAGT TCCATGGGCT CGCTCTCGTG AATACTTCTT    6540
TTATCTTGCT AAGCGCCGCA TTTTTCAAGA CAACTATGTG TTGCAAATCA CTGCTGCTGA    6600
TCCTTCGTTA GACTCTAAGG CTGCTCTTGA GGTGTTGAAG AACATGTGCA CTGCAGACTG    6660
GGATGACAAC AAAGCCGTTC TTGACTATTA TCTGTCCAGC GATGGAGACA TCACAGCCAA    6720
GATTAGCGAG ATGAAGAAGG CAGCTATCAA GGCACAGATC GAGCAGCTTC AGAAAGCTTT    6780
GGAGGGTTGA                                                           6790
```

( 2 ) INFORMATION FOR SEQ ID NO:23:

( i ) SEQUENCE CHARACTERISTICS:
        ( A ) LENGTH: 2089 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:23:

```
Met  Ala  Leu  Arg  Arg  Gly  Leu  Tyr  Ala  Ala  Ala  Ala  Thr  Ala  Ile  Leu
 1              5                        10                       15

Val  Thr  Ala  Ser  Val  Thr  Ala  Phe  Ala  Pro  Gln  His  Ser  Thr  Phe  Thr
              20                        25                       30

Pro  Gln  Ser  Leu  Ser  Ala  Ala  Pro  Thr  Arg  Asn  Val  Phe  Gly  Gln  Ile
              35                        40                       45

Lys  Ser  Ala  Phe  Phe  Asn  His  Asp  Val  Ala  Thr  Ser  Arg  Thr  Ile  Leu
     50                       55                  60

His  Ala  Ala  Thr  Leu  Asp  Glu  Thr  Val  Leu  Ser  Ala  Ser  Asp  Ser  Val
 65                      70                       75                       80

Ala  Lys  Ser  Val  Glu  Asp  Tyr  Val  Lys  Ser  Arg  Gly  Gly  Asn  Arg  Val
                    85                       90                       95

Ile  Arg  Lys  Val  Leu  Ile  Ala  Asn  Asn  Gly  Met  Ala  Ala  Thr  Lys  Ser
                  100                      105                      110

Ile  Leu  Ser  Met  Arg  Gln  Trp  Ala  Tyr  Met  Glu  Phe  Gly  Asp  Glu  Arg
               115                      120                      125

Ala  Ile  Gln  Phe  Val  Ala  Met  Ala  Thr  Pro  Glu  Asp  Leu  Lys  Ala  Asn
     130                      135                      140

Ala  Glu  Phe  Ile  Arg  Leu  Ala  Asp  Ser  Phe  Val  Glu  Val  Pro  Gly  Gly
145                      150                      155                      160

Lys  Asn  Leu  Asn  Asn  Tyr  Ala  Asn  Val  Asp  Val  Ile  Thr  Arg  Ile  Ala
                    165                      170                      175

Lys  Glu  Gln  Gly  Val  Asp  Ala  Val  Trp  Pro  Gly  Trp  Gly  His  Ala  Ser
               180                      185                      190

Glu  Asn  Pro  Lys  Leu  Pro  Asn  Ala  Leu  Asp  Lys  Leu  Gly  Ile  Lys  Phe
          195                      200                      205

Ile  Gly  Pro  Thr  Gly  Pro  Val  Met  Ser  Val  Leu  Gly  Asp  Lys  Ile  Ala
     210                      215                      220

Ala  Asn  Ile  Leu  Ala  Gln  Thr  Ala  Lys  Val  Pro  Ser  Ile  Pro  Trp  Ser
225                      230                      235                      240

Gly  Ser  Phe  Gly  Gly  Pro  Asp  Asp  Gly  Pro  Leu  Gln  Ala  Asp  Leu  Thr
                    245                      250                      255

Glu  Glu  Gly  Thr  Ile  Pro  Met  Glu  Ile  Phe  Asn  Lys  Gly  Leu  Val  Thr
               260                      265                      270

Ser  Ala  Asp  Glu  Ala  Val  Ile  Val  Ala  Asn  Lys  Ile  Gly  Trp  Glu  Asn
          275                      280                      285

Gly  Ile  Met  Ile  Lys  Ala  Ser  Glu  Gly  Gly  Gly  Gly  Lys  Gly  Ile  Arg
     290                      295                      300

Phe  Val  Asp  Asn  Glu  Ala  Asp  Leu  Arg  Asn  Ala  Phe  Val  Gln  Val  Ser
305                      310                      315                      320

Asn  Glu  Val  Ile  Gly  Ser  Pro  Ile  Phe  Leu  Met  Gln  Leu  Cys  Lys  Asn
                    325                      330                      335
```

```
Ala  Arg  His  Ile  Glu  Val  Gln  Ile  Val  Gly  Asp  Gln  His  Gly  Asn  Ala
               340                 345                      350

Val  Ala  Leu  Asn  Gly  Arg  Asp  Cys  Ser  Thr  Gln  Arg  Arg  Phe  Gln  Lys
               355                 360                      365

Ile  Phe  Glu  Glu  Gly  Pro  Pro  Ser  Ile  Val  Pro  Lys  Glu  Thr  Phe  His
          370                 375                      380

Glu  Met  Glu  Leu  Ala  Ala  Gln  Arg  Leu  Thr  Gln  Asn  Ile  Gly  Tyr  Gln
385                      390                      395                         400

Gly  Ala  Gly  Thr  Val  Glu  Tyr  Leu  Tyr  Asn  Ala  Ala  Asp  Asn  Lys  Phe
                    405                      410                     415

Phe  Phe  Leu  Glu  Leu  Asn  Pro  Arg  Leu  Gln  Val  Glu  His  Pro  Val  Thr
               420                 425                      430

Glu  Gly  Ile  Thr  Gly  Ala  Asn  Leu  Pro  Ala  Thr  Gln  Leu  Gln  Val  Ala
               435                 440                      445

Met  Gly  Ile  Pro  Leu  Phe  Asn  Ile  Pro  Asp  Ile  Arg  Arg  Leu  Tyr  Gly
     450                      455                      460

Arg  Glu  Asp  Ala  Tyr  Gly  Thr  Asp  Pro  Ile  Asp  Phe  Leu  Gln  Glu  Arg
465                      470                      475                         480

Tyr  Arg  Glu  Leu  Asp  Ser  His  Val  Ile  Ala  Ala  Arg  Ile  Thr  Ala  Glu
               485                 490                      495

Asn  Pro  Asp  Glu  Gly  Phe  Lys  Pro  Thr  Ser  Gly  Ser  Ile  Glu  Arg  Ile
          500                 505                      510

Lys  Phe  Gln  Ser  Thr  Pro  Asn  Val  Trp  Gly  Tyr  Phe  Ser  Val  Gly  Ala
          515                 520                      525

Asn  Gly  Gly  Ile  His  Glu  Phe  Ala  Asp  Ser  Gln  Phe  Gly  His  Leu  Phe
     530                 535                      540

Ala  Lys  Gly  Pro  Asn  Arg  Glu  Gln  Ala  Arg  Lys  Ala  Leu  Val  Leu  Ala
545                 550                      555                          560

Leu  Lys  Glu  Met  Glu  Val  Arg  Gly  Asp  Ile  Arg  Asn  Ser  Val  Glu  Tyr
               565                 570                      575

Leu  Val  Lys  Leu  Leu  Glu  Thr  Glu  Ala  Phe  Lys  Lys  Asn  Thr  Ile  Asp
               580                 585                      590

Thr  Ser  Trp  Leu  Asp  Gly  Ile  Ile  Lys  Glu  Lys  Ser  Val  Lys  Val  Glu
          595                 600                      605

Met  Pro  Ser  His  Leu  Val  Val  Gly  Ala  Ala  Val  Phe  Lys  Ala  Phe
     610                 615                      620

Glu  His  Val  Lys  Val  Ala  Thr  Glu  Glu  Val  Lys  Glu  Ser  Phe  Arg  Lys
625                      630                      635                         640

Gly  Gln  Val  Ser  Thr  Ala  Gly  Ile  Pro  Gly  Ile  Asn  Ser  Phe  Asn  Ile
                    645                      650                     655

Glu  Val  Ala  Tyr  Leu  Asp  Thr  Lys  Tyr  Pro  Phe  His  Val  Glu  Arg  Ile
                    660                      665                     670

Ser  Pro  Asp  Val  Tyr  Arg  Phe  Thr  Leu  Asp  Gly  Asn  Thr  Ile  Asp  Val
          675                      680                     685

Glu  Val  Thr  Gln  Thr  Ala  Glu  Gly  Ala  Leu  Leu  Ala  Thr  Phe  Gly  Gly
     690                 695                      700

Glu  Thr  His  Arg  Ile  Phe  Gly  Met  Asp  Glu  Pro  Leu  Gly  Leu  Arg  Leu
705                      710                      715                         720

Ser  Leu  Asp  Gly  Ala  Thr  Val  Leu  Met  Pro  Thr  Ile  Phe  Asp  Pro  Ser
               725                      730                     735

Glu  Leu  Arg  Thr  Asp  Val  Thr  Gly  Lys  Val  Val  Arg  Tyr  Leu  Gln  Asp
               740                 745                      750

Asn  Gly  Ala  Thr  Val  Glu  Ala  Gly  Gln  Pro  Tyr  Val  Glu  Val  Glu  Ala
```

-continued

```
              755                          760                          765
    Met Lys Met Ile Met Pro Ile Lys Ala Thr Glu Ser Gly Lys Ile Thr
            770                 775                 780
    His Asn Leu Ser Ala Gly Ser Val Ile Ser Ala Gly Asp Leu Leu Ala
    785                 790                 795                     800
    Ser Leu Glu Leu Lys Asp Pro Ser Arg Val Lys Lys Ile Glu Thr Phe
                        805                 810                 815
    Ser Gly Lys Leu Asp Ile Met Glu Ser Lys Val Asp Leu Glu Pro Gln
                820                 825                 830
    Lys Ala Val Met Asn Val Leu Ser Gly Phe Asn Leu Asp Pro Glu Ala
                835                 840                 845
    Val Ala Gln Gln Ala Ile Asp Ser Ala Thr Asp Ser Ser Ala Ala Ala
        850                 855                 860
    Asp Leu Leu Val Gln Val Leu Asp Glu Phe Tyr Arg Val Glu Ser Gln
    865                 870                 875                     880
    Phe Asp Gly Val Ile Ala Asp Asp Val Val Arg Thr Leu Thr Lys Ala
                        885                 890                 895
    Asn Thr Glu Thr Leu Asp Val Val Ile Ser Glu Asn Leu Ala His Gln
                900                 905                 910
    Gln Leu Lys Arg Arg Ser Gln Leu Leu Ala Met Ile Arg Gln Leu
                915                 920                 925
    Asp Thr Phe Gln Asp Arg Phe Gly Arg Glu Val Pro Asp Ala Val Ile
        930                 935                 940
    Glu Ala Leu Ser Arg Leu Ser Thr Leu Lys Asp Lys Ser Tyr Gly Glu
    945                 950                 955                     960
    Ile Ile Leu Ala Ala Glu Glu Arg Val Arg Glu Ala Lys Val Pro Ser
                        965                 970                 975
    Phe Glu Val Arg Arg Ala Asp Leu Arg Ala Lys Leu Ala Asp Pro Glu
                980                 985                 990
    Thr Asp Leu Ile Asp Leu Ser Lys Ser Ser Thr Leu Ser Ala Gly Val
                995                 1000                1005
    Asp Leu Leu Thr Asn Leu Phe Asp Asp Glu Asp Glu Ser Val Arg Ala
        1010                1015                1020
    Ala Ala Met Glu Val Tyr Thr Arg Arg Val Tyr Arg Thr Tyr Asn Ile
    1025                1030                1035                    1040
    Pro Glu Leu Thr Val Gly Val Glu Asn Gly Arg Leu Ser Cys Ser Phe
                        1045                1050                1055
    Ser Phe Gln Phe Ala Asp Val Pro Ala Lys Asp Arg Val Thr Arg Gln
                1060                1065                1070
    Gly Phe Phe Ser Val Ile Asp Asp Ala Ser Lys Phe Ala Gln Gln Leu
                1075                1080                1085
    Pro Glu Ile Leu Asn Ser Phe Gly Ser Lys Ile Ala Gly Asp Ala Ser
        1090                1095                1100
    Lys Glu Gly Pro Val Asn Val Leu Gln Val Gly Ala Leu Ser Gly Asp
    1105                1110                1115                    1120
    Ile Ser Ile Glu Asp Leu Glu Lys Ala Thr Ser Ala Asn Lys Asp Lys
                        1125                1130                1135
    Leu Asn Met Leu Gly Val Arg Thr Val Thr Ala Leu Ile Pro Arg Gly
                1140                1145                1150
    Lys Lys Asp Pro Ser Tyr Tyr Ser Phe Pro Gln Cys Ser Gly Phe Lys
                1155                1160                1165
    Glu Asp Pro Leu Arg Arg Gly Met Arg Pro Thr Phe His His Leu Leu
        1170                1175                1180
```

```
Glu Leu Gly Arg Leu Glu Glu Asn Phe Ala Leu Glu Arg Ile Pro Ala
1185               1190               1195               1200

Val Gly Arg Asn Val Gln Ile Tyr Val Gly Ser Glu Lys Thr Ala Arg
               1205               1210               1215

Arg Asn Ala Ala Gln Val Val Phe Leu Arg Ala Ile Ser His Thr Pro
            1220               1225               1230

Gly Leu Thr Thr Phe Ser Gly Ala Arg Arg Ala Leu Leu Gln Gly Leu
        1235               1240               1245

Asp Glu Leu Glu Arg Ala Gln Ala Asn Ser Lys Val Ser Val Gln Ser
    1250               1255               1260

Ser Ser Arg Ile Tyr Leu His Ser Leu Pro Glu Gln Ser Asp Ala Thr
1265               1270               1275               1280

Pro Glu Glu Ile Ala Lys Glu Phe Glu Gly Val Ile Asp Lys Leu Lys
               1285               1290               1295

Ser Arg Leu Ala Gln Arg Leu Thr Lys Leu Arg Val Asp Glu Ile Glu
            1300               1305               1310

Thr Lys Val Arg Val Thr Val Gln Asp Glu Asp Gly Ser Pro Arg Val
        1315               1320               1325

Val Pro Val Arg Leu Val Ala Ser Ser Met Gln Gly Glu Trp Leu Lys
    1330               1335               1340

Thr Ser Ala Tyr Ile Asp Arg Pro Asp Pro Val Thr Gly Val Thr Arg
1345               1350               1355               1360

Glu Arg Cys Val Ile Gly Glu Gly Ile Asp Glu Val Cys Glu Leu Glu
               1365               1370               1375

Ser Tyr Asp Ser Thr Ser Thr Ile Gln Thr Lys Arg Ser Ile Ala Arg
            1380               1385               1390

Arg Val Gly Ser Thr Tyr Ala Tyr Asp Tyr Leu Gly Leu Leu Glu Val
        1395               1400               1405

Ser Leu Leu Gly Glu Trp Asp Lys Tyr Leu Ser Ser Leu Ser Gly Pro
    1410               1415               1420

Asp Thr Pro Thr Ile Pro Ser Asn Val Phe Glu Ala Gln Glu Leu Leu
1425               1430               1435               1440

Glu Gly Pro Asp Gly Glu Leu Val Thr Gly Lys Arg Glu Ile Gly Thr
               1445               1450               1455

Asn Lys Val Gly Met Val Ala Trp Val Val Thr Met Lys Thr Pro Glu
            1460               1465               1470

Tyr Pro Glu Gly Arg Gln Val Val Val Ile Val Asn Asp Val Thr Val
        1475               1480               1485

Gln Ser Gly Ser Phe Gly Val Glu Glu Asp Glu Val Phe Phe Lys Ala
    1490               1495               1500

Ser Lys Tyr Ala Arg Glu Asn Lys Leu Pro Arg Val Tyr Ile Ala Cys
1505               1510               1515               1520

Asn Ser Gly Ala Arg Ile Gly Leu Val Asp Asp Leu Lys Pro Lys Phe
            1525               1530               1535

Gln Ile Lys Phe Ile Asp Glu Ala Ser Pro Ser Lys Gly Phe Glu Tyr
        1540               1545               1550

Leu Tyr Leu Asp Asp Ala Thr Tyr Lys Ser Leu Pro Glu Gly Ser Val
    1555               1560               1565

Asn Val Arg Lys Val Pro Glu Gly Trp Ala Ile Thr Asp Ile Ile Gly
1570               1575               1580

Thr Asn Glu Gly Ile Gly Val Glu Asn Leu Gln Gly Ser Gly Lys Ile
1585               1590               1595               1600

Ala Gly Glu Thr Ser Arg Ala Tyr Asp Glu Ile Phe Thr Leu Ser Tyr
            1605               1610               1615
```

```
Val  Thr  Gly  Arg  Ser  Val  Gly  Ile  Gly  Ala  Tyr  Leu  Val  Arg  Leu  Gly
               1620                1625                     1630

Gln  Arg  Ile  Ile  Gln  Met  Lys  Gln  Gly  Pro  Met  Ile  Leu  Thr  Gly  Tyr
               1635                1640                     1645

Gly  Ala  Leu  Asn  Lys  Leu  Leu  Gly  Arg  Glu  Val  Tyr  Asn  Ser  Asn  Asp
     1650                1655                     1660

Gln  Leu  Gly  Gly  Pro  Gln  Val  Met  Phe  Pro  Asn  Gly  Cys  Ser  His  Glu
1665                1670                     1675                     1680

Ile  Val  Asp  Asp  Gln  Gln  Gly  Ile  Gln  Ser  Ile  Ile  Gln  Trp  Leu
                    1685                1690                     1695

Ser  Phe  Val  Pro  Lys  Thr  Thr  Asp  Ala  Val  Ser  Pro  Val  Arg  Glu  Cys
                    1700                1705                     1710

Ala  Asp  Pro  Val  Asn  Arg  Asp  Val  Gln  Trp  Arg  Pro  Thr  Pro  Thr  Pro
          1715                     1720                     1725

Tyr  Asp  Pro  Arg  Leu  Met  Leu  Ser  Gly  Thr  Asp  Glu  Glu  Leu  Gly  Phe
     1730                     1735                     1740

Phe  Asp  Thr  Gly  Ser  Trp  Lys  Glu  Tyr  Leu  Ala  Gly  Trp  Gly  Lys  Ser
1745                     1750                     1755                     1760

Val  Val  Ile  Gly  Arg  Gly  Arg  Leu  Gly  Gly  Ile  Pro  Met  Gly  Ala  Ile
                    1765                     1770                     1775

Ala  Val  Glu  Thr  Arg  Leu  Val  Glu  Lys  Ile  Ile  Pro  Ala  Asp  Pro  Ala
               1780                1785                     1790

Asp  Pro  Asn  Ser  Arg  Glu  Ala  Val  Met  Pro  Gln  Ala  Gly  Gln  Val  Leu
               1795                1800                     1805

Phe  Pro  Asp  Ser  Ser  Tyr  Lys  Thr  Ala  Gln  Ala  Leu  Arg  Asp  Phe  Asn
          1810                     1815                     1820

Asn  Glu  Gly  Leu  Pro  Val  Met  Ile  Phe  Ala  Asn  Trp  Arg  Gly  Phe  Ser
1825                     1830                     1835                     1840

Gly  Gly  Ser  Arg  Asp  Met  Ser  Gly  Glu  Ile  Leu  Lys  Phe  Gly  Ser  Met
                    1845                     1850                     1855

Ile  Val  Asp  Ser  Leu  Arg  Glu  Tyr  Lys  His  Pro  Ile  Tyr  Ile  Tyr  Phe
                    1860                     1865                     1870

Pro  Pro  Tyr  Gly  Glu  Leu  Arg  Gly  Gly  Ser  Trp  Val  Val  Val  Asp  Pro
               1875                     1880                     1885

Thr  Ile  Asn  Glu  Asp  Lys  Met  Thr  Met  Phe  Ser  Asp  Pro  Asp  Ala  Arg
     1890                     1895                     1900

Gly  Gly  Ile  Leu  Glu  Pro  Ala  Gly  Ile  Val  Glu  Ile  Lys  Phe  Arg  Leu
1905                     1910                     1915                     1920

Ala  Asp  Gln  Leu  Lys  Ala  Met  His  Arg  Ile  Asp  Pro  Gln  Leu  Lys  Met
                    1925                     1930                     1935

Leu  Asp  Ser  Glu  Leu  Glu  Ser  Thr  Asp  Asp  Thr  Asp  Val  Ala  Ala  Gln
                    1940                     1945                     1950

Glu  Ala  Ile  Lys  Glu  Gln  Ile  Ala  Ala  Arg  Glu  Glu  Leu  Leu  Lys  Pro
               1955                     1960                     1965

Val  Tyr  Leu  Gln  Ala  Ala  Thr  Glu  Phe  Ala  Asp  Leu  His  Asp  Lys  Thr
     1970                     1975                     1980

Gly  Arg  Met  Lys  Ala  Lys  Gly  Val  Ile  Lys  Glu  Ala  Val  Pro  Trp  Ala
1985                     1990                     1995                     2000

Arg  Ser  Arg  Glu  Tyr  Phe  Phe  Tyr  Leu  Ala  Lys  Arg  Arg  Ile  Phe  Gln
                    2005                     2010                     2015

Asp  Asn  Tyr  Val  Leu  Gln  Ile  Thr  Ala  Ala  Asp  Pro  Ser  Leu  Asp  Ser
               2020                     2025                     2030

Lys  Ala  Ala  Leu  Glu  Val  Leu  Lys  Asn  Met  Cys  Thr  Ala  Asp  Trp  Asp
```

2035                          2040                          2045

Asp  Asn  Lys  Ala  Val  Leu  Asp  Tyr  Tyr  Leu  Ser  Ser  Asp  Gly  Asp  Ile
             2050                         2055                    2060

Thr  Ala  Lys  Ile  Ser  Glu  Met  Lys  Lys  Ala  Ala  Ile  Lys  Ala  Gln  Ile
        2065                     2070                         2075                    2080

Glu  Gln  Leu  Gln  Lys  Ala  Leu  Glu  Gly
                            2085

( 2 ) INFORMATION FOR SEQ ID NO:24:

( i ) SEQUENCE CHARACTERISTICS:
      ( A ) LENGTH: 2089 amino acids
      ( B ) TYPE: amino acid
      ( C ) STRANDEDNESS: single
      ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:24:

Met  Ala  Leu  Arg  Arg  Gly  Leu  Tyr  Ala  Ala  Ala  Ala  Thr  Ala  Ile  Leu
        1                   5                        10                       15

Val  Thr  Ala  Ser  Val  Thr  Ala  Phe  Ala  Pro  Gln  His  Ser  Thr  Phe  Thr
                            20                       25                       30

Pro  Gln  Ser  Leu  Ser  Ala  Ala  Pro  Thr  Arg  Asn  Val  Phe  Gly  Gln  Ile
                       35                       40                       45

Lys  Ser  Ala  Phe  Phe  Asn  His  Asp  Val  Ala  Thr  Ser  Arg  Thr  Ile  Leu
             50                       55                       60

His  Ala  Ala  Thr  Leu  Asp  Glu  Thr  Val  Leu  Ser  Ala  Ser  Asp  Ser  Val
        65                        70                       75                       80

Ala  Lys  Ser  Val  Glu  Asp  Tyr  Val  Lys  Ser  Arg  Gly  Gly  Asn  Arg  Val
                            85                       90                       95

Ile  Arg  Lys  Val  Leu  Ile  Ala  Asn  Asn  Gly  Met  Ala  Ala  Thr  Lys  Ser
                       100                      105                      110

Ile  Leu  Ser  Met  Arg  Gln  Trp  Ala  Tyr  Met  Glu  Phe  Gly  Asp  Glu  Arg
                  115                      120                      125

Ala  Ile  Gln  Phe  Val  Ala  Met  Ala  Thr  Pro  Glu  Asp  Leu  Lys  Ala  Asn
             130                      135                      140

Ala  Glu  Phe  Ile  Arg  Leu  Ala  Asp  Ser  Phe  Val  Glu  Val  Pro  Gly  Gly
        145                      150                      155                      160

Lys  Asn  Leu  Asn  Asn  Tyr  Ala  Asn  Val  Asp  Val  Ile  Thr  Arg  Ile  Ala
                            165                      170                      175

Lys  Glu  Gln  Gly  Val  Asp  Ala  Val  Trp  Pro  Gly  Trp  Gly  His  Ala  Ser
                       180                      185                      190

Glu  Asn  Pro  Lys  Leu  Pro  Asn  Ala  Leu  Asp  Lys  Leu  Gly  Ile  Lys  Phe
                  195                      200                      205

Ile  Gly  Pro  Thr  Gly  Pro  Val  Met  Ser  Val  Leu  Gly  Asp  Lys  Ile  Ala
             210                      215                      220

Ala  Asn  Ile  Leu  Ala  Gln  Thr  Ala  Lys  Val  Pro  Ser  Ile  Pro  Trp  Ser
        225                      230                      235                      240

Gly  Ser  Phe  Gly  Gly  Pro  Asp  Asp  Gly  Pro  Leu  Gln  Ala  Asp  Leu  Thr
                            245                      250                      255

Glu  Glu  Gly  Thr  Ile  Pro  Met  Glu  Ile  Phe  Asn  Lys  Gly  Leu  Val  Thr
                       260                      265                      270

Ser Ala Asp Glu Ala Val Ile Val Ala Asn Lys Ile Gly Trp Glu Asn
                275                 280                 285
Gly Ile Met Ile Lys Ala Ser Glu Gly Gly Gly Lys Gly Ile Arg
    290                 295                 300
Phe Val Asp Asn Glu Ala Asp Leu Arg Asn Ala Phe Val Gln Val Ser
305                 310                 315                 320
Asn Glu Val Ile Gly Ser Pro Ile Phe Leu Met Gln Leu Cys Lys Asn
                325                 330                 335
Ala Arg His Ile Glu Val Gln Ile Val Gly Asp Gln His Gly Asn Ala
            340                 345                 350
Val Ala Leu Asn Gly Arg Asp Cys Ser Thr Gln Arg Arg Phe Gln Lys
        355                 360                 365
Ile Phe Glu Glu Gly Pro Pro Ser Ile Val Pro Lys Glu Thr Phe His
    370                 375                 380
Glu Met Glu Leu Ala Ala Gln Arg Leu Thr Gln Asn Ile Gly Tyr Gln
385                 390                 395                 400
Gly Ala Gly Thr Val Glu Tyr Leu Tyr Asn Ala Ala Asp Asn Lys Phe
                405                 410                 415
Phe Phe Leu Glu Leu Asn Pro Arg Leu Gln Val Glu His Pro Val Thr
            420                 425                 430
Glu Gly Ile Thr Gly Ala Asn Leu Pro Ala Thr Gln Leu Gln Val Ala
        435                 440                 445
Met Gly Ile Pro Leu Phe Asn Ile Pro Asp Ile Arg Arg Leu Tyr Gly
    450                 455                 460
Arg Glu Asp Ala Tyr Gly Thr Asp Pro Ile Asp Phe Leu Gln Glu Arg
465                 470                 475                 480
Tyr Arg Glu Leu Asp Ser His Val Ile Ala Ala Arg Ile Thr Ala Glu
                485                 490                 495
Asn Pro Asp Glu Gly Phe Lys Pro Thr Ser Gly Ser Ile Glu Arg Ile
            500                 505                 510
Lys Phe Gln Ser Thr Pro Asn Val Trp Gly Tyr Phe Ser Val Gly Ala
        515                 520                 525
Asn Gly Gly Ile His Glu Phe Ala Asp Ser Gln Phe Gly His Leu Phe
    530                 535                 540
Ala Lys Gly Pro Asn Arg Glu Gln Ala Arg Lys Ala Leu Val Leu Ala
545                 550                 555                 560
Leu Lys Glu Met Glu Val Arg Gly Asp Ile Arg Asn Ser Val Glu Tyr
                565                 570                 575
Leu Val Lys Leu Leu Glu Thr Glu Ala Phe Lys Lys Asn Thr Ile Asp
            580                 585                 590
Thr Ser Trp Leu Asp Gly Ile Ile Lys Glu Lys Ser Val Lys Val Glu
        595                 600                 605
Met Pro Ser His Leu Val Val Gly Ala Ala Val Phe Lys Ala Phe
    610                 615                 620
Glu His Val Lys Val Ala Thr Glu Glu Val Lys Glu Ser Phe Arg Lys
625                 630                 635                 640
Gly Gln Val Ser Thr Ala Gly Ile Pro Gly Ile Asn Ser Phe Asn Ile
                645                 650                 655
Glu Val Ala Tyr Leu Asp Thr Lys Tyr Pro Phe His Val Glu Arg Ile
            660                 665                 670
Ser Pro Asp Val Tyr Arg Phe Thr Leu Asp Gly Asn Thr Ile Asp Val
        675                 680                 685
Glu Val Thr Gln Thr Ala Glu Gly Ala Leu Leu Ala Thr Phe Gly Gly

-continued

|     |     |     | 690 |     |     |     | 695 |     |     |     | 700 |     |     |     |
|-----|-----|-----|-----|-----|-----|-----|-----|-----|-----|-----|-----|-----|-----|-----|
| Glu | Thr | His | Arg | Ile | Phe | Gly | Met | Asp | Glu | Pro | Leu | Gly | Leu | Arg | Leu |
| 705 |     |     |     |     | 710 |     |     |     |     | 715 |     |     |     |     | 720 |

```
            690                             695                             700
Glu  Thr  His  Arg  Ile  Phe  Gly  Met  Asp  Glu  Pro  Leu  Gly  Leu  Arg  Leu
705                      710                     715                          720

Ser  Leu  Asp  Gly  Ala  Thr  Val  Leu  Met  Pro  Thr  Ile  Phe  Asp  Pro  Ser
                    725                     730                          735

Glu  Leu  Arg  Thr  Asp  Val  Thr  Gly  Lys  Val  Val  Arg  Tyr  Leu  Gln  Asp
                740                     745                          750

Asn  Gly  Ala  Thr  Val  Glu  Ala  Gly  Gln  Pro  Tyr  Val  Glu  Val  Glu  Ala
               755                      760                     765

Met  Lys  Met  Ile  Met  Pro  Ile  Lys  Ala  Thr  Glu  Ser  Gly  Lys  Ile  Thr
770                      775                     780

His  Asn  Leu  Ser  Ala  Gly  Ser  Val  Ile  Ser  Ala  Gly  Asp  Leu  Leu  Ala
785                 790                      795                              800

Ser  Leu  Glu  Leu  Lys  Asp  Pro  Ser  Arg  Val  Lys  Lys  Ile  Glu  Thr  Phe
                    805                     810                          815

Ser  Gly  Lys  Leu  Asp  Ile  Met  Glu  Ser  Lys  Val  Asp  Leu  Glu  Pro  Gln
               820                      825                     830

Lys  Ala  Val  Met  Asn  Val  Leu  Ser  Gly  Phe  Asn  Leu  Asp  Pro  Glu  Ala
          835                      840                     845

Val  Ala  Gln  Gln  Ala  Ile  Asp  Ser  Ala  Thr  Asp  Ser  Ser  Ala  Ala  Ala
850                      855                     860

Asp  Leu  Leu  Val  Gln  Val  Leu  Asp  Glu  Phe  Tyr  Arg  Val  Glu  Ser  Gln
865                 870                      875                              880

Phe  Asp  Gly  Val  Ile  Ala  Asp  Asp  Val  Val  Arg  Thr  Leu  Thr  Lys  Ala
               885                          890                         895

Asn  Thr  Glu  Thr  Leu  Asp  Val  Val  Ile  Ser  Glu  Asn  Leu  Ala  His  Gln
               900                      905                     910

Gln  Leu  Lys  Arg  Arg  Ser  Gln  Leu  Leu  Leu  Ala  Met  Ile  Arg  Gln  Leu
          915                      920                     925

Asp  Thr  Phe  Gln  Asp  Arg  Phe  Gly  Arg  Glu  Val  Pro  Asp  Ala  Val  Ile
930                      935                     940

Glu  Ala  Leu  Ser  Arg  Leu  Ser  Thr  Leu  Lys  Asp  Lys  Ser  Tyr  Gly  Glu
945                 950                      955                              960

Ile  Ile  Leu  Ala  Ala  Glu  Glu  Arg  Val  Arg  Glu  Ala  Lys  Val  Pro  Ser
               965                      970                     975

Phe  Glu  Val  Arg  Arg  Ala  Asp  Leu  Arg  Ala  Lys  Leu  Ala  Asp  Pro  Glu
               980                      985                     990

Thr  Asp  Leu  Ile  Asp  Leu  Ser  Lys  Ser  Ser  Thr  Leu  Ser  Ala  Gly  Val
               995                     1000                    1005

Asp  Leu  Leu  Thr  Asn  Leu  Phe  Asp  Asp  Glu  Asp  Glu  Ser  Val  Arg  Ala
     1010                    1015                    1020

Ala  Ala  Met  Glu  Val  Tyr  Thr  Arg  Arg  Val  Tyr  Arg  Thr  Tyr  Asn  Ile
1025                    1030                    1035                       1040

Pro  Glu  Leu  Thr  Val  Gly  Val  Glu  Asn  Gly  Arg  Leu  Ser  Cys  Ser  Phe
                    1045                    1050                       1055

Ser  Phe  Gln  Phe  Ala  Asp  Val  Pro  Ala  Lys  Asp  Arg  Val  Thr  Arg  Gln
               1060                     1065                    1070

Gly  Phe  Phe  Ser  Val  Ile  Asp  Asp  Ala  Ser  Lys  Phe  Ala  Gln  Gln  Leu
     1075                    1080                    1085

Pro  Glu  Ile  Leu  Asn  Ser  Phe  Gly  Ser  Lys  Ile  Ala  Gly  Asp  Ala  Ser
     1090                    1095                    1100

Lys  Glu  Gly  Pro  Val  Asn  Val  Leu  Gln  Val  Gly  Ala  Leu  Ser  Gly  Asp
1105                    1110                    1115                       1120
```

```
Ile Ser Ile Glu Asp Leu Glu Lys Ala Thr Ser Ala Asn Lys Asp Lys
              1125                1130                    1135
Leu Asn Met Leu Gly Val Arg Thr Val Thr Ala Leu Ile Pro Arg Gly
              1140                1145                    1150
Lys Lys Asp Pro Ser Tyr Tyr Ser Phe Pro Gln Cys Ser Gly Phe Lys
              1155                1160                    1165
Glu Asp Pro Leu Arg Arg Gly Met Arg Pro Thr Phe His His Leu Leu
        1170                1175                    1180
Glu Leu Gly Arg Leu Glu Glu Asn Phe Ala Leu Glu Arg Ile Pro Ala
1185                1190                1195                1200
Val Gly Arg Asn Val Gln Ile Tyr Val Gly Ser Glu Lys Thr Ala Arg
              1205                1210                    1215
Arg Asn Ala Ala Gln Val Val Phe Leu Arg Ala Ile Ser His Thr Pro
              1220                1225                    1230
Gly Leu Thr Thr Phe Ser Gly Ala Arg Arg Ala Leu Leu Gln Gly Leu
              1235                1240                    1245
Asp Glu Leu Glu Arg Ala Gln Ala Asn Ser Lys Val Ser Val Gln Ser
              1250                1255                    1260
Ser Ser Arg Ile Tyr Leu His Ser Leu Pro Glu Gln Ser Asp Ala Thr
1265                1270                1275                1280
Pro Glu Glu Ile Ala Lys Glu Phe Glu Gly Val Ile Asp Lys Leu Lys
              1285                1290                    1295
Ser Arg Leu Ala Gln Arg Leu Thr Lys Leu Arg Val Asp Glu Ile Glu
              1300                1305                    1310
Thr Lys Val Arg Val Thr Val Gln Asp Glu Asp Gly Ser Pro Arg Val
              1315                1320                    1325
Val Pro Val Arg Leu Val Ala Ser Ser Met Gln Gly Glu Trp Leu Lys
              1330                1335                    1340
Thr Ser Ala Tyr Ile Asp Arg Pro Asp Pro Val Thr Gly Val Thr Arg
1345                1350                1355                1360
Glu Arg Cys Val Ile Gly Glu Gly Ile Asp Glu Val Cys Glu Leu Glu
              1365                1370                    1375
Ser Tyr Asp Ser Thr Ser Thr Ile Gln Thr Lys Arg Ser Ile Ala Arg
              1380                1385                    1390
Arg Val Gly Ser Thr Tyr Ala Tyr Asp Tyr Leu Gly Leu Leu Glu Val
              1395                1400                    1405
Ser Leu Leu Gly Glu Trp Asp Lys Tyr Leu Ser Ser Leu Ser Gly Pro
              1410                1415                    1420
Asp Thr Pro Thr Ile Pro Ser Asn Val Phe Glu Ala Gln Glu Leu Leu
1425                1430                1435                1440
Glu Gly Pro Asp Gly Glu Leu Val Thr Gly Lys Arg Glu Ile Gly Thr
              1445                1450                    1455
Asn Lys Val Gly Met Val Ala Trp Val Val Thr Met Lys Thr Pro Glu
              1460                1465                    1470
Tyr Pro Glu Gly Arg Gln Val Val Val Ile Val Asn Asp Val Thr Val
              1475                1480                    1485
Gln Ser Gly Ser Phe Gly Val Glu Glu Asp Glu Val Phe Phe Lys Ala
              1490                1495                    1500
Ser Lys Tyr Ala Arg Glu Asn Lys Leu Pro Arg Val Tyr Ile Ala Cys
1505                1510                1515                1520
Asn Ser Gly Ala Arg Ile Gly Leu Val Asp Asp Leu Lys Pro Lys Phe
              1525                1530                    1535
Gln Ile Lys Phe Ile Asp Glu Ala Ser Pro Ser Lys Gly Phe Glu Tyr
              1540                1545                    1550
```

```
Leu Tyr Leu Asp Asp Ala Thr Tyr Lys Ser Leu Pro Glu Gly Ser Val
    1555                1560                1565

Asn Val Arg Lys Val Pro Glu Gly Trp Ala Ile Thr Asp Ile Ile Gly
    1570                1575                1580

Thr Asn Glu Gly Ile Gly Val Glu Asn Leu Gln Gly Ser Gly Lys Ile
1585                1590                1595                1600

Ala Gly Glu Thr Ser Arg Ala Tyr Asp Glu Ile Phe Thr Leu Ser Tyr
                1605                1610                1615

Val Thr Gly Arg Ser Val Gly Ile Gly Ala Tyr Leu Val Arg Leu Gly
                1620                1625                1630

Gln Arg Ile Ile Gln Met Lys Gln Gly Pro Met Ile Leu Thr Gly Tyr
                1635                1640                1645

Gly Ala Leu Asn Lys Leu Leu Gly Arg Glu Val Tyr Asn Ser Asn Asp
    1650                1655                1660

Gln Leu Gly Gly Pro Gln Val Met Phe Pro Asn Gly Cys Ser His Glu
1665                1670                1675                1680

Ile Val Asp Asp Asp Gln Gln Gly Ile Gln Ser Ile Ile Gln Trp Leu
                1685                1690                1695

Ser Phe Val Pro Lys Thr Thr Asp Ala Val Ser Pro Val Arg Glu Cys
                1700                1705                1710

Ala Asp Pro Val Asn Arg Asp Val Gln Trp Arg Pro Thr Pro Thr Pro
    1715                1720                1725

Tyr Asp Pro Arg Leu Met Leu Ser Gly Thr Asp Glu Glu Leu Gly Phe
    1730                1735                1740

Phe Asp Thr Gly Ser Trp Lys Glu Tyr Leu Ala Gly Trp Gly Lys Ser
1745                1750                1755                1760

Val Val Ile Gly Arg Gly Arg Leu Gly Gly Ile Pro Met Gly Ala Ile
                1765                1770                1775

Ala Val Glu Thr Arg Leu Val Glu Lys Ile Ile Pro Ala Asp Pro Ala
    1780                1785                1790

Asp Pro Asn Ser Arg Glu Ala Val Met Pro Gln Ala Gly Gln Val Leu
    1795                1800                1805

Phe Pro Asp Ser Ser Tyr Lys Thr Ala Gln Ala Leu Arg Asp Phe Asn
    1810                1815                1820

Asn Glu Gly Leu Pro Val Met Ile Phe Ala Asn Trp Arg Gly Phe Ser
1825                1830                1835                1840

Gly Gly Ser Arg Asp Met Ser Gly Glu Ile Leu Lys Phe Gly Ser Met
                1845                1850                1855

Ile Val Asp Ser Leu Arg Glu Tyr Lys His Pro Ile Tyr Ile Tyr Phe
                1860                1865                1870

Pro Pro Tyr Gly Glu Leu Arg Gly Gly Ser Trp Val Val Val Asp Pro
    1875                1880                1885

Thr Ile Asn Glu Asp Lys Met Thr Met Phe Ser Asp Pro Asp Ala Arg
    1890                1895                1900

Gly Gly Ile Leu Glu Pro Ala Gly Ile Val Glu Ile Lys Phe Arg Leu
1905                1910                1915                1920

Ala Asp Gln Leu Lys Ala Met His Arg Ile Asp Pro Gln Leu Lys Met
                1925                1930                1935

Leu Asp Ser Glu Leu Glu Ser Thr Asp Asp Thr Asp Val Ala Ala Gln
                1940                1945                1950

Glu Ala Ile Lys Glu Gln Ile Ala Ala Arg Glu Glu Leu Leu Lys Pro
                1955                1960                1965

Val Tyr Leu Gln Ala Ala Thr Glu Phe Ala Asp Leu His Asp Lys Thr
```

```
                  1970                    1975                    1980
      Gly  Arg  Met  Lys  Ala  Lys  Gly  Val  Ile  Lys  Glu  Ala  Val  Pro  Trp  Ala
      1985                    1990                    1995                    2000
      Arg  Ser  Arg  Glu  Tyr  Phe  Phe  Tyr  Leu  Ala  Lys  Arg  Arg  Ile  Phe  Gln
                          2005                    2010                    2015
      Asp  Asn  Tyr  Val  Leu  Gln  Ile  Thr  Ala  Ala  Asp  Pro  Ser  Leu  Asp  Ser
                     2020                    2025                         2030
      Lys  Ala  Ala  Leu  Glu  Val  Leu  Lys  Asn  Met  Cys  Thr  Ala  Asp  Trp  Asp
                2035                    2040                    2045
      Asp  Asn  Lys  Ala  Val  Leu  Asp  Tyr  Tyr  Leu  Ser  Ser  Asp  Gly  Asp  Ile
                2050                    2055                    2060
      Thr  Ala  Lys  Ile  Ser  Glu  Met  Lys  Lys  Ala  Ala  Ile  Lys  Ala  Gln  Ile
      2065                    2070                    2075                    2080
      Glu  Gln  Leu  Gln  Lys  Ala  Leu  Glu  Gly
                          2085
```

( 2 ) INFORMATION FOR SEQ ID NO:25:

( i ) SEQUENCE CHARACTERISTICS:
        ( A ) LENGTH: 6270 bases
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( x i ) SEQUENCE DESCRIPTION: SEQ ID NO:25:

```
ATGGCTCTCC  GTAGGGGCCT  TTACGCTGCT  GCAGCGACTG  CCATCTTGGT  CACGGCTTC    60
GTGACCGCTT  TTGCTCCTCA  GCATTCGACA  TTCACCCCCC  AATCGCTCTC  GGCGGCAC    120
ACGCGCAACG  TCTTCGGCCA  GATCAAAAGC  GCCTTCTTCA  ACCATGATGT  TGCCACCT    180
CGAACCATTC  TTCACGCCGC  GACACTAGAT  GAAACTGTTC  TTTCCGCTTC  AGACTCCG    240
GCCAAATCTG  TCGAAGACTA  CGTGAAATCC  CGTGGTGGAA  ATCGCGTCAT  TCGTAAAG    300
CTCATCGCCA  CAACGGCAT   GGCCGCGACA  AAGTCCATCC  TCTCCATGCG  TCAATGGG    360
TACATGGAAT  TCGGGGACGA  ACGTGCCATC  CAGTTCGTTG  CGATGGCGAC  TCCCGAGG    420
TTGAAGGCGA  ACGCCGAATT  TATTCGCTTG  GCGGATTCTT  TCGTCGAGGT  ACCGGGAG    480
AAGAACTTGA  CAACTACGC   CAACGTCGAT  GTCATTACCC  GCATCGCTAA  GGAGCAGG    540
GTTGATGCCG  TTTGGCCTGG  ATGGGGTCAT  GCATCTGAGA  ATCCGAAGCT  CCCTAATG    600
CTTGACAAAT  TGGGAATCAA  GTTCATTGGA  CCAACTGGGC  TGTCATGAG   CGTTTTGG    660
GACAAGATTG  CTGCGAACAT  TCTAGCACAG  ACAGCGAAAG  TCCCCTCCAT  TCCCTGGA    720
GGATCCTTTG  GTGGACCAGA  CGATGGACCC  CTTCAGGCGG  ATCTGACCGA  GGAGGGTA    780
ATCCCAATGG  AAATCTTTAA  CAAGGGATTA  GTAACCTCTG  CTGATGAAGC  CGTCATTG    840
GCGAACAAGA  TTGGCTGGGA  GAACGGAATC  ATGATCAAGG  CTTCTGAGGG  TGGAGGAG    900
AAGGGTATAC  GCTTTGTCGA  CAATGAGGCC  GACTTACGGA  ACGCGTTCGT  TCAGGTGT    960
AATGAAGTGA  TTGGCTCTCC  TATTTTCCTC  ATGCAGTTGT  GTAAGAACGC  TCGTCAC     1020
GAAGTGCAAA  TTGTTGGCGA  CCAGCACGGA  AATGCTGTAG  CGTTGAACGG  TCGAGAT     1080
TCCACTCAGC  GTCGCTTCCA  AAGATCTTC   GAGGAAGGTC  CTCCGTCCAT  TGTACCG     1140
GAAACATTCC  ACGAGATGGA  ACTTGCGGCT  CAACGGTTGA  CTCAAAACAT  TGGGTAT     1200
```

| | | | | | |
|---|---|---|---|---|---|
| GGTGCTGGAA | CTGTGGAATA | CTTGTACAAC | GCCGCTGACA | ATAAGTTTTT | CTTCCTT 1260 |
| TTGAACCCCC | GTCTCCAAGT | GGAGCATCCT | GTGACTGAAG | GAATTACCGG | CGCTAAT 1320 |
| CCTGCCACTC | AGCTTCAAGT | TGCTATGGGT | ATTCCTCTCT | TCAACATTCC | TGACATT 1380 |
| CGTCTCTATG | GAAGAGAGGA | TGCTTACGGA | ACGGATCCCA | TTGATTTTCT | TCAAGAA 1440 |
| TACCGCGAAC | TCGACTCTCA | TGTAATTGCT | GCCCGCATCA | CTGCTGAAAA | CCCCGAT 1500 |
| GGATTCAAAC | CCACCTCAGG | CTCAATTGAG | CGAATCAAAT | TCAATCCAC | CCCAAAT 1560 |
| TGGGGATATT | TCTCTGTTGG | TGCTAACGGT | GGAATCCATG | AATTTGCCGA | CTCTCAG 1620 |
| GGCCATCTTT | TCGCTAAGGG | TCCGAACCGT | GAGCAAGCCC | GCAAGGCATT | GGTTTTG 1680 |
| CTTAAGGAGA | TGGAAGTGCG | CGGAGACATT | CGTAACTCTG | TTGAATACCT | AGTCAAG 1740 |
| CTCGAAACTG | AAGCTTTCAA | GAAGAACACT | ATCGACACGT | CTTGGTTAGA | TGGCATT 1800 |
| AAGGAGAAGT | CCGTTAAAGT | TGAGATGCCC | TCTCACTTAG | TGGTTGTCGG | AGCCGCT 1860 |
| TTCAAGGCCT | TCGAACATGT | TAAGGTGGCC | ACTGAAGAAG | TTAAGGAATC | GTTTCGA 1920 |
| GGACAAGTCT | CCACTGCAGG | GATTCCAGGC | ATAAACTCGT | TCAACATCGA | AGTTGCG 1980 |
| TTAGACACGA | AGTACCCATT | CCACGTAGAA | CGGATCTCTC | CAGATGTTTA | CAGGTTT 2040 |
| TTGGACGGGA | ACACGATTGA | TGTGGAAGTT | ACCCAAACCG | CTGAAGGAGC | ACTTTTG 2100 |
| ACCTTTGGAG | GAGAGACTCA | TCGTATCTTT | GGTATGGACG | AACCACTTGG | CCTTCGA 2160 |
| TCATTGGACG | GGGCAACTGT | CCTAATGCCA | ACAATTTTTG | ACCCCTCTGA | ACTCCGC 2220 |
| GATGTGACTG | GAAAGGTTGT | TCGTTACCTC | CAAGACAATG | GAGCAACTGT | TGAAGCG 2280 |
| CAGCCCTATG | TCGAGGTTGA | AGCGATGAAG | ATGATCATGC | CAATCAAGGC | TACTGAG 2340 |
| GGAAAAATTA | CTCACAACCT | AAGTGCTGGA | TCTGTAATCT | CTGCTGGTGA | CCTTCTT 2400 |
| TCTCTCGAAC | TTAAGGATCC | CTCTAGGGTT | AAGAAAATAG | AAACTTTTTC | GGGCAAA 2460 |
| GACATTATGG | AATCGAAGGT | TGACTTAGAA | CCGCAGAAAG | CAGTCATGAA | TGTCCTC 2520 |
| GGGTTCAACT | TAGACCCTGA | GGCAGTTGCG | CAGCAAGCAA | TTGACAGTGC | TACCGAC 2580 |
| TCTGCCGCAG | CCGATCTTCT | TGTCCAAGTA | TTAGACGAAT | CTATCGCGT | TGAATCT 2640 |
| TTTGATGGTG | TCATCGCTGA | TGATGTTGTC | CGCACTCTCA | CCAAAGCGAA | CACCGAG 2700 |
| CTTGATGTTG | TCATCTCCGA | GAACTTGGCC | CACCAGCAGC | TCAAGAGGCG | TAGTCAG 2760 |
| CTCCTCGCTA | TGATCCGTCA | ACTTGACACG | TTTCAAGACA | GATTTGGCAG | AGAAGTT 2820 |
| GATGCTGTCA | TTGAAGCATT | GAGTAGGCTT | TCTACCTTGA | AAGACAAATC | TTACGGT 2880 |
| ATCATTCTTG | CGGCTGAGGA | GAGAGTCCGC | GAAGCCAAGG | TGCCGTCCTT | CGAAGTG 2940 |
| CGTGCTGATT | TGCGTGCAAA | GCTTGCTGAC | CCGGAGACAG | ATTTGATTGA | CCTGAGT 3000 |
| AGCTCAACAC | TCTCAGCAGG | GGTTGACCTT | CTCACAAATC | TTTTTGATGA | CGAAGAT 3060 |
| TCTGTCCGCG | CTGCTGCTAT | GGAAGTATAT | ACTCGCCGTG | TCTACCGTAC | CTACAAC 3120 |
| CCCGAGCTAA | CTGTTGGAGT | TGAGAATGGC | CGCCTCTCAT | GTAGCTTCTC | CTTCCAA 3180 |
| GCTGATGTCC | CGGCGAAAGA | CCGTGTCACC | CGCCAAGGGT | TCTTCTCAGT | TATCGAC 3240 |
| GCTTCAAAGT | TCGCGCAACA | GCTTCCTGAG | ATTCTCAACT | CGTTTGGATC | AAAGATC 3300 |
| GGGGATGCAA | GCAAAGAAGG | CCCTGTCAAT | GTTTTGCAGG | TTGGTGCTCT | CTCGGGA 3360 |
| ATCAGTATTG | AGGACCTCGA | GAAAGCTACT | TCCGCTAACA | AGGACAAGTT | GAATATG 3420 |
| GGTGTCCGCA | CTGTGACGGC | TCTTATCCCA | AGGGGAAAGA | AGGACCCAAG | CTATTAT 3480 |
| TTCCCCCAAT | GCAGTGGCTT | CAAGGAGGAT | CCTCTTCGCA | GAGGCATGCG | CCCAACC 3540 |
| CATCATCTCC | TGGAACTCGG | ACGGCTGGAG | GAAAACTTTG | CTCTTGAACG | AATTCCT 3600 |

| | | | | | |
|---|---|---|---|---|---|
| GTTGGACGCA | ACGTACAGAT | TTATGTTGGT | TCCGAGAAGA | CGGCAAGGCG | AAATGCA 3660 |
| CAAGTTGTTT | TCTTGAGAGC | TATCTCACAT | ACTCCTGGCC | TAACTACCTT | CTCTGGT 3720 |
| CGCCGAGCTC | TTCTCCAGGG | GCTTGACGAA | TTGGAACGTG | CTCAAGCAAA | CTCAAAG 3780 |
| AGTGTCCAGT | CATCGTCTCG | CATCTACCTT | CACTCTCTCC | AGAACAGTC | TGATGCA 3840 |
| CCCGAGGAGA | TTGCTAAAGA | ATTCGAAGGT | GTCATTGACA | AGCTAAAGAG | TCGATTG 3900 |
| CAACGTCTTA | CGAAACTGCG | TGTGGATGAG | ATTGAAACCA | AGGTTCGCGT | GACTGTC 3960 |
| GATGAAGACG | GTAGTCCCAG | GGTTGTGCCT | GTACGCCTTG | TGGCTTCTTC | AATGCAA 4020 |
| GAATGGCTTA | AAACATCTGC | TTACATTGAT | CGTCCGGACC | CGGTCACTGG | AGTCACC 4080 |
| GAACGGTGCG | TGATTGGAGA | AGGCATTGAC | GAGGTTTGTG | AACTTGAGTC | GTATGAC 4140 |
| ACCAGTACCA | TCCAAACAAA | GCGCTCAATT | GCAAGACGTG | TGGGATCTAC | CTACGCT 4200 |
| GACTACCTTG | GACTCCTTGA | GGTCAGCTTG | CTTGGAGAAT | GGGATAAGTA | TCTCAGC 4260 |
| CTCTCAGGAC | CGGACACCCC | TACCATCCCG | TCGAATGTTT | TTGAAGCTCA | AGAGTTA 4320 |
| GAAGGACCTG | ATGGCGAGCT | TGTCACCGGG | AAACGTGAAA | TTGGAACAAA | TAAGGTT 4380 |
| ATGGTTGCAT | GGGTGGTAAC | AATGAAAACA | CCTGAATATC | CTGAGGGTCG | ACAGGTT 4440 |
| GTAATTGTGA | ACGATGTCAC | TGTACAAAGT | GGTTCATTTG | GAGTTGAGGA | GGATGAA 4500 |
| TTCTTCAAGG | CCTCCAAATA | TGCTCGCGAA | AATAAGCTCC | CCGTGTCTA | CATTGCG 4560 |
| AACTCTGGTG | CTAGAATTGG | TTTGGTGGAT | GATCTCAAGC | CAAAGTTCCA | GATCAAA 4620 |
| ATTGATGAGG | CGAGTCCATC | TAAGGGTTTT | GAGTACCTTT | ATCTTGATGA | TGCAACG 4680 |
| AAATCTCTTC | CAGAAGGGTC | GGTAAATGTA | AGGAAGGTCC | CTGAAGGCTG | GCTATC 4740 |
| GATATCATTG | GAACGAACGA | AGGAATTGGG | GTTGAGAACC | TTCAAGGAAG | TGGCAAA 4800 |
| GCTGGCGAGA | CATCAAGGGC | ATATGATGAA | ATCTTCACCT | TGAGTTACGT | CACAGGT 4860 |
| AGTGTTGGTA | TTGGAGCTTA | CCTTGTCCGT | CTCGGCCAGC | GTATTATTCA | GATGAAA 4920 |
| GGACCCATGA | TTCTCACAGG | CTATGGTGCC | CTGAATAAGC | TTCTCGGCCG | TGAAGTG 4980 |
| AACTCAAACG | ACCAACTTGG | TGGTCCTCAA | GTCATGTTCC | CAAACGGCTG | CTCTCAT 5040 |
| ATTGTAGATG | ATGACCAACA | AGGCATCCAG | TCCATTATCC | AATGGCTAAG | CTTTGTT 5100 |
| AAGACAACTG | ATGCTGTGTC | ACCCGTCCGT | GAATGTGCCG | ACCCTGTCAA | CAGGGAT 5160 |
| CAATGGCGCC | CTACCCCCAC | TCCTTATGAT | CCACGCCTCA | TGCTCTCAGG | AACTGAC 5220 |
| GAACTCGGTT | TTTTTGACAC | AGGAAGCTGG | AAGGAATATC | TTGCTGGCTG | GGGGAAG 5280 |
| GTTGTTATTG | GCCGCGGTCG | CCTTGGTGGC | ATTCCTATGG | GTGCTATTGC | CGTGGAG 5340 |
| CGGCTTGTTG | AGAAGATTAT | CCCTGCAGAT | CCAGCAGACC | CCAACTCCCG | CGAAGCT 5400 |
| ATGCCCCAGG | CTGGACAAGT | TCTTTTCCCT | GACTCATCCT | ACAAGACAGC | CCAAGCT 5460 |
| CGCGACTTTA | ATAACGAGGG | CCTCCCTGTG | ATGATTTTCG | GCAACTGGCG | TGGATTT 5520 |
| GGTGGAAGTC | GTGACATGTC | TGGTGAAATC | CTCAAATTTG | GATCCATGAT | TGTCGAT 5580 |
| CTCCGAGAGT | ACAAACATCC | TATTTACATA | TACTTCCCTC | CATATGGTGA | ACTTCGA 5640 |
| GGATCGTGGG | TTGTGGTGGA | CCCCACTATC | AATGAGGACA | AGATGACCAT | GTTCTCA 5700 |
| CCTGATGCTC | GTGGTGGTAT | TCTCGAACCT | GCTGGTATTG | TAGAAATCAA | GTTCCGC 5760 |
| GCAGACCAGC | TGAAAGCCAT | GCACCGCATT | GATCCCCAGC | TGAAGATGCT | AGATTCA 5820 |
| CTTGAGTCGA | CAGACGACAC | AGATGTCGCT | GCTCAAGAAG | CAATCAAAGA | GCAGATT 5880 |
| GCAAGAGAGG | AGCTTCTTAA | ACCCGTCTAT | CTTCAGGCTG | CTACTGAATT | TGCTGAT 5940 |
| CACGACAAGA | CGGGACGGAT | GAAGGCGAAG | GGTGTTATCA | AAGAAGCAGT | TCCATGG 6000 |

| | | | | | | |
|---|---|---|---|---|---|---|
| CGCTCTCGTG | AATACTTCTT | TTATCTTGCT | AAGCGCCGCA | TTTTTCAAGA | CAACTAT | 6060 |
| TTGCAAATCA | CTGCTGCTGA | TCCTTCGTTA | GACTCTAAGG | CTGCTCTTGA | GGTGTTG | 6120 |
| AACATGTGCA | CTGCAGACTG | GGATGACAAC | AAAGCCGTTC | TTGACTATTA | TCTGTCC | 6180 |
| GATGGAGACA | TCACAGCCAA | GATTAGCGAG | ATGAAGAAGG | CAGCTATCAA | GGCACAG | 6240 |
| GAGCAGCTTC | AGAAAGCTTT | GGAGGGTTGA | | | | 6270 |

What is claimed is:

1. An isolated and purified DNA encoding an acetyl-coenzyme A carboxylase (ACCase) protein from *Cyclotella cryptica* having ACCase activity.

2. The DNA according to claim 1 wherein the amino acid sequence of the encoded protein is:

```
MALRRGLYAAAATAILVTASVTAFAPQHSTFTPQSLSAAPTRNVFGQIKSAFFNHDVATS
RTILHAATLDETVLSASDSVAKSVEDYVKSRGGNRVIRKVLIANNGMAATKSILSMRQW
AYMEFGDERAIQFVAMATPEDLKANAEFIRLADSFVEVPGGKNLNNYANVDVITRIAKE
QGVDAVWPGWGHASENPKLPNALDKLGIKFIGPTGPVMSVLGDKIAANILAQTAKVPSIP
WSGSFGGPDDGPLQADLTEEGTIPMEIFNKGLVTSADEAVIVANKIGWENGIMIKASEGG
GGKGIRFVDNEADLRNAFVQVSNEVIGSPIFLMQLCKNARHIEVQIVGDQHGNAVALNG
RDCSTQRRFQKIFEEGPPSIVPKETFHEMELAAQRLTQNIGYQGAGTVEYLYNAADNKFF
FLELNPRLQVEHPVTEGITGANLPATQLQVAMGIPLFNIPDIRRLYGREDAYGTDPIDFLQ
ERYRELDSHVIAARITAENPDEGFKPTSGSIERIKFQSTPNVWGYFSVGANGGIHEFADSQ
FGHLFAKGPNREQARKALVLALKEMEVRGDIRNSVEYLVKLLETEAFKKNTIDTSWLDG
IIKEKSVKVEMPSHLVVVGAAVFKAFEHVKVATEEVKESFRKGQVSTAGIPGINSFNIEVA
YLDTKYPFHVERISPDVYRFTLDGNTIDVEVTQTAEGALLATFGGETHRIFGMDEPLGLR
LSLDGATVLMPTIFDPSELRTDVTGKVVRYLQDNGATVEAGQPYVEVEAMKMIMPIKAT
ESGKITHNLSAGSVISAGDLLASLELKDPSRVKKIETFSGKLDIMESKVDLEPQKAVMNVL
SGFNLDPEAVAQQAIDSATDSSAAADLLVQVLDEFYRVESQFDGVIADDVVRTLTKANT
ETLDVVISENLAHQQLKRRSQLLLAMIRQLDTFQDRFGREVPDAVIEALSRLSTLKDKSY
GEIILAAEERVREAKVPSFEVRRADLRAKLADPETDLIDLSKSSTLSAGVDLLTNLFDDED
ESVRAAAMEVYTRRVYRTYNIPELTVGVENGRLSCSFSFQFADVPAKDRVTRQGFFSVID
DASKFAQQLPEILNSFGSKIAGDASKEGPVNVLQVGALSGDISIEDLEKATSANKDKLNM
LGVRTVTALIPRGKKDPSYYSFPQCSGFKEDPLRRGMRPTFHHLLELGRLEENFALERIPA
VGRNVQIYVGSEKTARRNAAQVVFLRAISHTPGLTTFSGARRALLQGLDELERAQANSK
VSVQSSSRIYLHSLPEQSDATPEEIAKEFEGVIDKLKSRLAQRLTKLRVDEIETKVRVTVQ
DEDGSPRVVPVRLVASSMQGEWLKTSAYIDRPDPVTGVTRERCVIGEGIDEVCELESYDS
TSTIQTKRSIARRVGSTYAYDYLGLLEVSLLGEWDKYLSSLSGPDTPTIPSNVFEAQELLE
GPDGELVTGKREIGTNKVGMVAWVVTMKTPEYPEGRQVVVIVNDVTVQSGSFGVEED
EVFFKASKYARENKLPRVYIACNSGARIGLVDDLKPKFQIKFIDEASPSKGFEYLYLDDAT
YKSLPEGSVNVRKVPEGWAITDIIGTNEGIGVENLQGSGKIAGETSRAYDEIFTLSYVTGR
SVGIGAYLVRLGQRIIQMKQGPMILTGYGALNKLLGREVYNSNDQLGGPQVMFPNGCSH
EIVDDDQQGIQSIIQWLSFVPKTTDAVSPVRECADPVNRDVQWRPTPTPYDPRLMLSGTD
EELGFFDTGSWKEYLAGWGKSVVIGRGRLGGIPMGAIAVETRLVEKIIPADPADPNSREA
VMPQAGQVLFPDSSYKTAQALRDFNNEGLPVMIFANWRGFSGGSRDMSGEILKFGSMIV
DSLREYKHPIYIYFPPYGELRGGSWVVVDPTINEDKMTMFSDPDARGGILEPAGIVEIKFR
LADQLKAMHRIDPQLKMLDSELESTDDTDVAAQEAIKEQIAAREELLKPVYLQAATEFA
DLHDKTGRMKAKGVIKEAVPWARSREYFFYLAKRRIFQDNYVLQITAADPSLDSKAALE
VLKNMCTADWDDNKAVLDYYLSSDGDITAKISEMKKAAIKAQIEQLQKALEG (SEQ ID NO:23).
```

3. A vector containing the DNA of claim 1.

4. A vector containing the DNA of claim 2.

5. A host cell containing the vector of claim 3.

6. A host cell containing the vector of claim 4.

7. The host cell of claim 6, wherein said host is *Cyclotella cryptica*.

8. The DNA according to claim 2 wherein the DNA sequence is:

```
ATGGCTCTCCGTAGGGGCCTTTACGCTGCTGCAGCGACTGCCATCTTGGTCACGGCTT
CAGTGACCGCTTTTGGTAAGTCTGCATTTGGATTGATGGTTAGCATTCCCCACGAGCA
GCATGTTGTGTTACGCGTTGTTGCGTAGTGTCAGTTGTGATAATTATGATCGACAAGA
ATGGGAGGACTCTTTTTGTATCGTTTGTAGAGTGTTACACTGGACCTTCGCCTAAACA
CGTTTGGAGGTCCTCACATCCGCGACGAGAGCTCCCACATTTCATCTACATCTCTACG
TGAGCGAATTTACGTCACCTGGCTATTCATTTGAGGTCCCTTCCTCCCACGTGCTTCC
ATGTTCCTTAGGGCGCTTAAGCATAGTTGCACTTGGAGCACTTGTTGTCAAATTGTCG
TGTACCCGTCACTTTCGAAGCGTTATTTGGGGTTGGCTGGTCCTATTTAAACAGAAAT
```

-continued

```
TATTACGATGTTTCGCTAACGATTCTTTCTCTCATTTTTTAACCTACACGAAACAGCTC
CTCAGCATTCGACATTCACCCCCCAATCGCTCTCGGCGGCACCCACGCGCAACGTCTT
CGGCCAGATCAAAAGCGCCTTCTTCAACCATGATGTTGCCACCTCTCGAACCATTCTT
CACGCCGCGACACTAGATGAAACTGTTCTTTCCGCTTCAGACTCCGTCGCCAAATCTG
TCGAAGACTACGTGAAATCCCGTGGTGGAAATCGCGTCATTCGTAAAGTCCTCATCG
CCAACAACGGCATGGCCGCGACAAAGTCCATCCTCTCCATGCGTCAATGGGCCTACA
TGGAATTCGGGGACGAACGTGCCATCCAGTTCGTTGCGATGGCGACTCCCGAGGATT
TGAAGGCGAACGCCGAATTTATTCGCTTGGCGGATTCTTTCGTCGAGGTACCGGGAG
GAAAGAACTTGAACAACTACGCCAACGTCGATGTCATTACCCGCATCGCTAAGGAGC
AGGGGGTTGATGCCGTTTGGCCTGGATGGGGTCATGCATCTGAGAATCCGAAGCTCC
CTAATGCGCTTGACAAATTGGGAATCAAGTTCATTGGACCAACTGGGCCTGTCATGA
GCGTTTTGGGAGACAAGATTGCTGCGAACATTCTAGCACAGACAGCGAAAGTCCCCT
CCATTCCCTGGAGTGGATCCTTTGGTGGACCAGACGATGGACCCCTTCAGGCGGATC
TGACCGAGGAGGGTACTATCCCAATGGAAATCTTTAACAAGGGATTAGTAACCTCTG
CTGATGAAGCCGTCATTGTGGCGAACAAGATTGGCTGGGAGAACGGAATCATGATCA
AGGCTTCTGAGGGTGGAGGAGGAAAGGGTATACGCTTTGTCGACAATGAGGCCGAC
TTACGGAACGCGTTCGTTCAGGTGTCCAATGAAGTGATTGGCTCTCCTATTTTCCTCA
TGCAGTTGTGTAAGAACGCTCGTCACATCGAAGTGCAAATTGTTGGCGACCAGCACG
GAAATGCTGTAGCGTTGAACGGTCGAGATTGCTCCACTCAGCGTCGCTTCCAGAAGA
TCTTCGAGGAAGGTCCTCCCGTCCATTGTACCGAAAGAAACATTCCACGAGATGGAAC
TTGCGGCTCAACGGTTGACTCAAAAACATTGGGTATCGAAGGTGCTGGAACTGTGGAAT
ACTTGTACAACGCCGCTGACAATAAGTTTTTCTTCCTTGAGTTGAACCCCCGTCTCCA
AGTGGAGCATCCTGTGACTGAAGGAATTACCGGCGCTAATCTTCCTGCCACTCAGCT
TCAAGTTGCTATGGGTATTCCTCTCTTCAACATTCCTGACATTCGCCGTCTCTATGGA
AGAGAGGATGCTTACGGAACGGATCCCATTGATTTTCTTCAAGAACGTTACCGCGAA
CTCGACTCTCATGTAATTGCTGCCCGCATCACTGCTGAAAACCCCGATGAAGGATTCA
AACCCACCTCAGGCTCAATTGAGCGAATCAAATTTCAATCCACCCCAAATGTTTGGG
GATATTTCTCTGTTGGTGCTAACGGTGGAATCCATGAATTTGCCGACTCTCAGTTTGG
CCATCTTTTCGCTAAGGGTCCGAACCGTGAGCAAGCCCGCAAGGCATTGGTTTTGGC
TCTTAAGGAGATGGAAGTGCGCGGAGACATTCGTAACTCTGTTGAATACCTAGTCAA
GTTGCTCGAAACTGAAGCTTTCAAGAAGAACACTATCGACACGTCTTGGTTAGATGG
CATTATTAAGGAGAAGTCCGTTAAAGTTGAGATGCCCTCTCACTTAGTGGTTGTCGG
AGCCGCTGTTTTCAAGGCCTTCGAACATGTTAAGGTGGCCACTGAAGAAGTTAAGGA
ATCGTTTCGAAAAGGACAAGTCTCCACTGCAGGGATTCCAGGCATAAACTCGTTCAA
CATCGAAGTTGCGTACTTAGACACGAAGTACCCATTCCACGTAGAACGGATCTCTCC
AGATGTTTACAGGTTTACCTTGGACGGGAACACGATTGATGTGGAAGTTACCCAAAC
CGCTGAAGGAGCACTTTTGGCAACCTTTGGAGGAGAGACTCATCGTATCTTTGGTAT
GGACGAACCACTTGGCCTTCGACTGTCATTGGACGGGGCAACTGTCCTAATGTAAGT
TGTCTGTCCCTCGATGTCGCTGTTTCATCTGTAGTCAAGTATCCTCACCTTATGTACTT
ATTCGTAGGCCAACAATTTTTGACCCCTCTGAACTCCGCACTGATGTGACTGGAAAG
GTTGTTCGTTACCTCCAAGACAATGGAGCAACTGTTGAAGCGGGCCAGCCCTATGTC
GAGGTTGAAGCGATGAAGATGATCATGCCAATCAAGGCTACTGAGTCTGGAAAAATT
ACTCACAACCTAAGTGCTGGATCTGTAATCTCTGCTGGTGACCTTCTTGCTTCTCTCG
AACTTAAGGATCCCTCTAGGGTTAAGAAAATAGAAACTTTTTCGGGCAAATTGGACA
TTATGGAATCGAAGGTTGACTTAGAACCGCAGAAAGCAGTCATGAATGTCCTCTCTG
GGTTCAACTTAGACCCTGAGGCAGTTGCGCAGCAAGCAATTGACAGTGCTACCGACA
GCTCTGCCGCAGCCGATCTTCTTGTCCAAGTATTAGACGAATTCTATCGCGTTGAATC
TCAGTTTGATGGTGTCATCGCTGATGATGTTGTCCGCACTCTCACCAAAGCGAACACC
GAGACACTTGATGTTGTCATCTCCGAGAACTTGGCCCACCAGCAGCTCAAGAGGCGT
AGTCAGCTTCTCCTCGCTATGATCCGTCAACTTGACACGTTTCAAGACAGATTTGGCA
GAGAAGTTCCGGATGCTGTCATTGAAGCATTGAGTAGGCTTTCTACCTTGAAAGACA
AATCTTACGGTGAAATCATTCTTGCGGCTGAGGAGAGAGTCCGCGAAGCCAAGGTGC
CGTCCTTCGAAGTGCGTCGTGCTGATTTGCGTGCAAAGCTTGCTGACCCGGAGACAG
ATTTGATTGACCTGAGTAAGAGCTCAACACTCTCAGCAGGGGTTGACCTTCTCACAA
ATCTTTTTGATGACGAAGATGAATCTGTCCGCGCTGCTGCTATGGAAGTATATACTCG
CCGTGTCTACCGTACCTACAACATCCCCGAGCTAACTGTTGGAGTTGAGAATGGCCG
CCTCTCATGTAGCTTCTCCTTCCAATTTGCTGATGTCCCGGCGAAAGACCGTGTCACC
CGCCAAGGGTTCTTCTCAGTTATCGACGACGCTTCAAAGTTCGCGCAACAGCTTCCTG
AGATTCTCAACTCGTTTGGATCAAAGATCGCAGGGGATGCAAGCAAAGAAGGCCCTG
TCAATGTTTTGCAGGTTGGTGCTCTCTCGGGAGATATCAGTATTGAGGACCTCGAGA
AAGCTACTTCCGCTAACAAGGACAAGTTGAATATGCTTGGTGTCCGCACTGTGACGG
CTCTTATCCCAAGGGGAAAGAAGGACCCAAGCTATTATTCATTCCCCCAATGCAGTG
GCTTCAAGGAGGATCCTCTTCGCAGAGGCATGCGCCCAACCTTTCATCATCTCCTGGA
ACTCGGACGGCTGGAGGAAAACTTTGCTCTTGAACGAATTCCTGCAGTTGGACGCAA
CGTACAGATTTATGTTGGTTCCGAGAAGACGGCAAGGCGAAATGCAGCTCAAGTTGT
TTTCTTGAGAGCTATCTCACATACTCCTGGCCTAACTACCTTCTCTGGTGCACGCCGA
GCTCTTCTCCAGGGGCTTGACGAATTGGAACGTGCTCAAGCAAACTCAAAGGTCAGT
GTCCAGTCATCGTCTCGCATCTACCTTCACTCTCTCCCAGAACAGTCTGATGCAACTC
CCGAGGAGATTGCTAAAGAATTCGAAGGTGTCATTGACAAGCTAAAGAGTCGATTGG
CCCAACGTCTTACGAAACTGCGTGTGGATGAGATTGAAACCAAGGTTCGCGTGACTG
TCCAGGATGAAGACGGTAGTCCCAGGGTTGTGCCTGTACGCCTTGTGGCTTCTTCAA
TGCAAGGCGAATGGCTTAAAACATCTGCTTACATTGATCGTCCGGACCCGGTCACTG
GAGTCACCCGTGAACGGTGCGTGATTGGAGAAGGCATTGACGAGGTTTGTGAACTTG
AGTCGTATGACTCTACCAGTACCATCCAAACAAAGCGCTCAATTGCAAGACGTGTGG
GATCTACCTACGCTTATGACTACCTTGGACTCCTTGAGGTCAGCTTGCTTGGAGAATG
GGATAAGTATCTCAGCAGTCTCTCAGGACCGGACACCCCTACCATCCCGTCGAATGT
TTTTGAAGCTCAAGAGTTACTTGAAGGACCTGATGGCGAGCTTGTCACCGGGAAACG
TGAAATTGGAACAAATAAGGTTGGTATGGTTGCATGGGTGGTAACAATGAAAACACC
TGAATATCCTGAGGGTCGACAGGTTGTTGTAATTGTGAACGATGTCACTGTACAAAG
TGGTTCATTTGGAGTTGAGGAGGATGAAGTTTTCTTCAAGGCCTCCAAATATGCTCGC
```

```
GAAAATAAGCTCCCCCGTGTCTACATTGCGTGCAACTCTGGTGCTAGAATTGGTTTG
GTGGATGATCTCAAGCCAAAGTTCCAGATCAAATTCATTGATGAGGCGAGTCCATCT
AAGGGTTTTGAGTACCTTTATCTTGATGATGCAACGTACAAATCTCTTCCAGAAGGGT
CGGTAAATGTAAGGAAGGTCCCTGAAGGCTGGGCTATCACTGATATCATTGGAACGA
ACGAAGGAATTGGGGTTGAGAACCTTCAAGGAAGTGGCAAAATTGCTGGCGAGACA
TCAAGGGCATATGATGAAATCTTCACCTTGAGTTACGTCACAGGTAGAAGTGTTGGT
ATTGGAGCTTACCTTGTCCGTCTCGGCCAGCGTATTATTCAGATGAAACAAGGACCC
ATGATTCTCACAGGCTATGGTGCCCTGAATAAGCTTCTCGGCCGTGAAGTGTACAAC
TCAAACGACCAACTTGGTGGTCCTCAAGTCATGTTCCCAAACGGCTGCTCTCATGAA
ATTGTAGATGATGACCAACAAGGCATCCAGTCCATTATCCAATGGCTAAGCTTTGTTC
CCAAGACAACTGATGCTGTGTCACCCGTCCGTGAATGTGCCGACCCTGTCAACAGGG
ATGTTCAATGGCGCCCTACCCCCACTCCTTATGATCCACGCCTCATGCTCTCAGGAAC
TGACGAGGAACTCGGTTTTTTTGACACAGGAAGCTGGAAGGAATATCTTGCTGGCTG
GGGGAAGAGTGTTGTTATTGGCCGCGGTCGCCTTGGTGGCATTCCTATGGGTGCTAT
TGCCGTGGAGACCCGGCTTGTTGAGAAGATTATCCCTGCAGATCCAGCAGACCCCAA
CTCCCGCGAAGCTGTCATGCCCCAGGCTGGACAAGTTCTTTTCCCTGACTCATCCTAC
AAGACAGCCCAAGCTCTCCGCGACTTTAATAACGAGGGCCTCCCTGTGATGATTTTC
GGCAACTGGCGTGGATTTAGTGGTGGAAGTCGTGACATGTCTGGTGAAATCCTCAAA
TTTGGATCCATGATTGTCGATTCACTCCGAGAGTACAAACATCCTATTTACATATACT
TCCCTCCATATGGTGAACTTCGAGGAGGATCGTGGGTTGTGGTGGACCCCACTATCA
ATGAGGACAAGATGACCATGTTCTCAGATCCTGATGCTCGTGGTGGTATTCTCGAAC
CTGCTGGTATTGTAGAAATCAAGTTCCGCTTGGCAGACCAGCTGAAAGCCATGCACC
GCATTGATCCCCAGCTGAAGATGCTAGATTCAGAGCTTGAGTCGACAGACGACACAG
ATGTCGCTGCTCAAGAAGCAATCAAAGAGCAGATTGCTGCAAGAGAGGAGCTTCTTA
AACCCGTCTATCTTCAGGCTGCTACTGAATTTGCTGATCTCCACGACAAGACGGGAC
GGATGAAGGCGAAGGGTGTTATCAAAGAAGCAGTTCCATGGGCTCGCTCTCGTGAAT
ACTTCTTTTATCTTGCTAAGCGCCGCATTTTTCAAGACAACTATGTGTTGCAAATCAC
TGCTGCTGATCCTTCGTTAGACTCTAAGGCTGCTCTTGAGGTGTTGAAGAACATGTGC
ACTGCAGACTGGGATGACAACAAAGCCGTTCTTGACTATTATCTGTCCAGCGATGGA
GACATCACAGCCAAGATTAGCGAGATGAAGAAGGCAGCTATCAAGGCACAGATCGA
GCAGCTTCAGAAAGCTTTGGAGGGTTGA (SEQ ID NO:22).
```

9. The DNA of claim 2 having the sequence:

```
ATGGCTCTCCGTAGGGGCCTTTACGCTGCTGCAGCGACTGCCATCTTGGTCACGGCTT
CAGTGACCGCTTTTGCTCCTCAGCATTCGACATTCACCCCCCAATCGCTCTCGGCGGC
ACCCACGCGCAACGTCTTCGGCCAGATCAAAAGCGCCTTCTTCAACCATGATGTTGC
CACCTCTCGAACCATTCTTCACGCCGCGACACTAGATGAAACTGTTCTTTCCGCTTCA
GACTCCGTCGCCAAATCTGTCGAAGACTACGTGAAATCCCGTGGTGGAAATCGCGTC
ATTCGTAAAGTCCTCATCGCCAACAACGGCATGGCCGCGACAAAGTCCATCCTCTCC
ATGCGTCAATGGGCCTACATGGAATTCGGGGACGAACGTGCCATCCAGTTCGTTGCG
ATGGCGACTCCCGAGGATTTGAAGGCGAACGCCGAATTTATTCGCTTGGCGGATTCT
TTCGTCGAGGTACCGGGAGGAAAGAACTTGAACAACTACGCCAACGTCGATGTCATT
ACCCGCATCGCTAAGGAGCAGGGGGTTGATGCCGTTTGGCCTGGATGGGGTCATGCA
TCTGAGAATCCGAAGCTCCCTAATGCGCTTGACAAATTGGGAATCAAGTTCATTGGA
CCAACTGGGCCTGTCATGAGCGTTTTGGGAGACAAGATTGCTGCGAACATTCTAGCA
CAGACAGCGAAAGTCCCCTCCATTCCCTGGAGTGGATCCTTTGGTGGACCAGACGAT
GGACCCCTTCAGGCGGATCTGACCGAGGAGGGTACTATCCCAATGGAAATCTTTAAC
AAGGGATTAGTAACCTCTGCTGATGAAGCCGTCATTGTGGCGAACAAGATTGGCTGG
GAGAACGGAATCATGATCAAGGCTTCTGAGGGTGGAGGAGGAAAGGGTATACGCTT
TGTCGACAATGAGGCCGACTTACGGAACGCGTTCGTTCAGGTGTCCAATGAAGTGAT
TGGCTCTCCTATTTTCCTCATGCAGTTGTGTAAGAACGCTCGTCACATCGAAGTGCAA
ATTGTTGGCGACCAGCACGGAAATGCTGTAGCGTTGAACGGTCGAGATTGCTCCACT
CAGCGTCGCTTCCAGAAGATCTTCGAGGAAGGTCCTCCGTCCATTGTACCGAAAGAA
ACATTCCACGAGATGGAACTTGCGGCTCAACGGTTGACTCAAAACATTGGGTATCAA
GGTGCTGGAACTGTGGAATACTTGTACAACGCCGCTGACAATAAGTTTTTCTTCCTTG
AGTTGAACCCCCGTCTCCAAGTGGAGCATCCTGTGACTGAAGGAATTACCGGCGCTA
ATCTTCCTGCCACTCAGCTTCAAGTTGCTATGGGTATTCCTCTCTTCAACATTCCTGA
CATTCGCCGTCTCTATGGAAGAGAGGATGCTTACGGAACGGATCCCATTGATTTTCTT
CAAGAACGTTACCGCGAACTCGACTCTCATGTAATTGCTGCCCGCATCACTGCTGAA
AACCCCGATGAAGGATTCAAACCCACCTCAGGCTCAATTGAGCGAATCAAATTTCAA
TCCACCCCAAATGTTTGGGGATATTTCTCTGTTGGTGCTAACGGTGGAATCCATGAAT
TTGCCGACTCTCAGTTTGGCCATCTTTTCGCTAAGGGTCCGAACCGTGAGCAAGCCCG
CAAGGCATTGGTTTTGGCTCTTAAGGAGATGGAAGTGCGCGGAGACATTCGTAACTC
TGTTGAATACCTAGTCAAGTTGCTCGAAACTGAAGCTTTCAAGAAGAACACTATCGA
CACGTCTTGGTTAGATGGCATTATTAAGGAGAAGTCCGTTAAAGTTGAGATGCCCTC
TCACTTAGTGGTTGTCGGAGCCGCTGTTTTCAAGGCCTTCGAACATGTTAAGGTGGCC
ACTGAAGAAGTTAAGGAATCGTTTCGAAAAGGACAAGTCTCCACTGCAGGGATTCCA
GGCATAAACTCGTTCAACATCGAAGTTGCGTACTTAGACACGAAGTACCCATTCCAC
GTAGAACGGATCTCTCCAGATGTTTACAGGTTTACCTTGGACGGGAACACGATTGAT
GTGGAAGTTACCCAAACCGCTGAAGGAGCACTTTTGGCAACCTTTGGAGGAGAGACT
CATCGTATCTTTGGTATGGACGAACCACTTGGCCTTCGACTGTCATTGGACGGGGCA
ACTGTCCTAATGCCAACAATTTTTGACCCCTCTGAACTCCGCACTGATGTGACTGGAA
AGGTTGTTCGTTACCTCCAAGACAATGGAGCAACTGTTGAAGCGGGCCAGCCCTATG
TCGAGGTTGAAGCGATGAAGATGATCATGCCAATCAAGGCTACTGAGTCTGGAAAAA
TTACTCACAACCTAAGTGCTGGATCTGTAATCTCTGCTGGTGACCTTCTTGCTTCTCT
```

-continued

```
CGAACTTAAGGATCCCTCTAGGGTTAAGAAAATAGAAACTTTTTCGGGCAAATTGGA
CATTATGGAATCGAAGGTTGACTTAGAACCGCAGAAAGCAGTCATGAATGTCCTCTC
TGGGTTCAACTTAGACCCTGAGGCAGTTGCGCAGCAAGCAATTGACAGTGCTACCGA
CAGCTCTGCCGCAGCCGATCTTCTTGTCCAAGTATTAGACGAATTCTATCGCGTTGAA
TCTCAGTTTGATGGTGTCATCGCTGATGATGTTGTCCGCACTCTCACCAAAGCGAACA
CCGAGACACTTGATGTTGTCATCTCCGAGAACTTGGCCCACCAGCAGCTCAAGAGGC
GTAGTCAGCTTCTCCTCGCTATGATCCGTCAACTTGACACGTTTCAAGACAGATTTGG
CAGAGAAGTTCCGGATGCTGTCATTGAAGCATTGAGTAGGCTTTCTACCTTGAAAGA
CAAATCTTACGGTGAAATCATTCTTGCGGCTGAGGAGGAGAGTCCGCGAAGCCAAGGT
GCCGTCCTTCGAAGTGCGTCGTGCTGATTGCGTGCAAAGCTTGCTGACCCGGAGAC
AGATTTGATTGACCTGAGTAAGAGCTCAACACTCTCAGCAGGGGTTGACCTTCTCAC
AAATCTTTTTGATGACGAAGATGAATCTGTCCGCGCTGCTGCTATGGAAGTATATACT
CGCCGTGTCTACCGTACCTACAACATCCCCGAGCTAACTGTTGGAGTTGAGAATGGC
CGCCTCTCATGTAGCTTCTCCTTCCAATTTGCTGATGTCCCGGCGAAAGACCGTGTCA
CCCGCCAAGGGTTCTTCTCAGTTATCGACGACGCTTCAAAGTTCGCGCAACAGCTTCC
TGAGATTCTCAACTCGTTTGGATCAAAGATCGCAGGGGATGCAAGCAAAGAAGGCCC
TGTCAATGTTTTGCAGGTTGGTGCTCTCTCGGGAGATATCAGTATTGAGGACCTCGA
GAAAGCTACTTCCGCTAACAAGGACAAGTTGAATATGCTTGGTGTCCGCACTGTGAC
GGCTCTTATCCCAAGGGGAAAGAAGGACCCAAGCTATTATTCATTCCCCCAATGCAG
TGGCTTCAAGGAGGATCCTCTTCGCAGAGGCATGCGCCCAACCTTTCATCATCTCCTG
GAACTCGGACGGCTGGAGGAAAACTTTGCTCTTGAACGAATTCCTGCAGTTGGACGC
AACGTACAGATTTATGTTGGTTCCGAGAAGACGGCAAGGCGAAATGCAGCTCAAGTT
GTTTTCTTGAGAGCTATCTCACATACTCCTGGCCTAACTACCTTCTCTGGTGCACGCC
GAGCTCTTCTCCAGGGGCTTGACGAATTGGAACGTGCTCAAGCAAACTCAAAGGTCA
GTGTCCAGTCATCGTCTCGCATCTACCTTCACTCTCTCCCAGAACAGTCTGATGCAAC
TCCCGAGGAGATTGCTAAAGAATTCGAAGGTGTCATTGACAAGCTAAAGAGTCGATT
GGCCCAACGTCTTACGAAACTGCGTGTGGATGAGATTGAAACCAAGGTTCGCGTGAC
TGTCCAGGATGAAGACGGTAGTCCCAGGGTTGTGCCTGTACGCCTTGTGGCTTCTTC
AATGCAAGGCGAATGGCTTAAAACATCTGCTTACATTGATCGTCCGGACCCGGTCAC
TGGAGTCACCCGTGAACGGTGCGTGATTGGAGAAGGCATTGACGAGGTTTGTGAACT
TGAGTCGTATGACTCTACCAGTACCATCCAAACAAAGCGCTCAATTGCAAGACGTGT
GGGATCTACCTACGCTTATGACTACCTTGGACTCCTTGAGGTCAGCTTGCTTGGAGAA
TGGGATAAGTATCTCAGCAGTCTCTCAGGACCGGACACCCCTACCATCCCGTCGAAT
GTTTTTGAAGCTCAAGAGTTACTTGAAGGACCTGATGGCGAGCTTGTCACCGGGAAA
CGTGAAATTGGAACAAATAAGGTTGGTATGGTTGCATGGGTGGTAACAATGAAAACA
CCTGAATATCCTGAGGGTCGACAGGTTGTTGTAATTGTGAACGATGTCACTGTACAA
AGTGGTTCATTTGGAGTTGAGGAGGATGAAGTTTTCTTCAAGGCCTCCAAATATGCT
CGCGAAAATAAGCTCCCCCGTGTCTACATTGCGTGCAACTCTGGTGCTAGAATTGGTT
TGGTGGATGATCTCAAGCCAAAGTTCCAGATCAAATTCATTGATGAGGCGAGTCCAT
CTAAGGGTTTTGAGTACCTTTATCTTGATGATGCAACGTACAAATCTCTTCCAGAAGG
GTCGGTAAATGTAAGGAAGGTCCCTGAAGGCTGGGCTATCACTGATATCATTGGAAC
GAACGAAGGAATTGGGGTTGAGAACCTTCAAGGAAGTGGCAAAATTGCTGGCGAGA
CATCAAGGGCATATGATGAAATCTTCACCTTGAGTTACGTCACAGGTAGAAGTGTTG
GTATTGGAGCTTACCTTGTCCGTCTCGGCCAGCGTATTATTCAGATGAAACAAGGAC
CCATGATTCTCACAGGCTATGGTGCCCTGAATAAGCTTCTCGGCCGTGAAGTGTACA
ACTCAAACGACCAACTTGGTGGTCCTCAAGTCATGTTCCCAAACGGCTGCTCTCATGA
AATTGTAGATGATGACCAACAAGGCATCCAGTCCATTATCCAATGGCTAAGCTTTGTT
CCCAAGACAACTGATGCTGTGTCACCCGTCCGTGAATGTGCCGACCCTGTCAACAGG
GATGTTCAATGGCGCCCTACCCCCACTCCTTATGATCCACGCCTCATGCTCTCAGGAA
CTGACGAGGAACTCGGTTTTTTTGACACAGGAAGCTGGAAGGAATATCTTGCTGGCT
GGGGGAAGAGTGTTGTTATTGGCCGCGGTCGCCTTGGTGGCATTCCTATGGGTGCTA
TTGCCGTGGAGACCCGGCTTGTTGAGAAGATTATCCCTGCAGATCCAGCAGACCCCA
ACTCCCGCGAAGCTGTCATGCCCCAGGCTGGACAAGTTCTTTTCCCTGACTCATCCTA
CAAGACAGCCCAAGCTCTCCGCGACTTTAATAACGAGGGCCTCCCTGTGATGATTTTC
GGCAACTGGCGTGGATTTAGTGGTGGAAGTCGTGACATGTCTGGTGAAATCCTCAAA
TTTGGATCCATGATTGTCGATTCACTCCGAGAGTACAAACATCCTATTTACATATACT
TCCCTCCATATGGTGAACTTCGAGGAGGATCGTGGGTTGTGGTGGACCCCACTATCA
ATGAGGACAAGATGACCATGTTCTCAGATCCTGATGCTCGTGGTGGTATTCTCGAAC
CTGCTGGTATTGTAGAAATCAAGTTCCGCTTGGCAGACCAGCTGAAAGCCATGCACC
GCATTGATCCCCAGCTGAAGATGCTAGATTCAGAGCTTGAGTCGACAGACGACACAG
ATGTCGCTGCTCAAGAAGCAATCAAAGAGCAGATTGCTGCAAGAGAGGAGCTTCTTA
AACCCGTCTATCTTCAGGCTGCTACTGAATTTGCTGATCTCCACGACAAGACGGGAC
GGATGAAGGCGAAGGGTGTTATCAAAGAAGCAGTTCCATGGGCTCGCTCTCGTGAAT
ACTTCTTTTATCTTGCTAAGCGCCGCATTTTTCAAGACAACTATGTGTTGCAAATCAC
TGCTGCTGATCCTTCGTTAGACTCTAAGGCTGCTCTTGAGGTGTTGAAGAACATGTGC
ACTGCAGACTGGGATGACAACAAAGCCGTTCTTGACTATTATCTGTCCAGCGATGGA
GACATCACAGCCAAGATTAGCGAGATGAAGAAGGCAGCTATCAAGGCACAGATCGA
GCAGCTTCAGAAAGCTTTGGAGGGTTGA (SEQ ID NO:25).
```

UNITED STATES PATENT AND TRADEMARK OFFICE
CERTIFICATE OF CORRECTION

PATENT NO. : 5,559,220
DATED : September 24, 1996
INVENTOR(S) : Paul G. Roessler and John B. Ohlrogge Page 1 of 5

It is certified that error appears in the above-indentified patent and that said Letters Patent is hereby corrected as shown below:

Under Sequence Description seq. Id. No.: 25:

Beginning with Columns 62 through 68, starting at line 39, numbers 60 through 6240, the far right-hand sequences should appear as Follows:

(See attached 4 pages.)

UNITED STATES PATENT AND TRADEMARK OFFICE
CERTIFICATE OF CORRECTION

PATENT NO. : 5,559,220

DATED : September 24, 1996

INVENTOR(S) : Paul G. Roessler and John B. Ohlrogge

It is certified that error appears in the above-identified patent and that said Letters Patent is hereby corrected as shown below:

(2) INFORMATION FOR SEQ ID NO:25:

(i) SEQUENCE CHARACTERISTICS:
        (A) LENGTH: 6270 bases
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:25:

```
ATGGCTCTCC GTAGGGGCCT TTACGCTGCT GCAGCGACTG CCATCTTGGT CACGGCTTCA   60
GTGACCGCTT TTGCTCCTCA GCATTCGACA TTCACCCCCC AATCGCTCTC GGCGGCACCC  120
ACGCGCAACG TCTTCGGCCA GATCAAAAGC GCCTTCTTCA ACCATGATGT TGCCACCTCT  180
CGAACCATTC TTCACGCCGC GACACTAGAT GAAACTGTTC TTTCCGCTTC AGACTCCGTC  240
GCCAAATCTG TCGAAGACTA CGTGAAATCC CGTGGTGGAA ATCGCGTCAT TCGTAAAGTC  300
CTCATCGCCA ACAACGGCAT GGCCGCGACA AAGTCCATCC TCTCCATGCG TCAATGGGCC  360
TACATGGAAT TCGGGGACGA ACGTGCCATC CAGTTCGTTG CGATGGCGAC TCCCGAGGAT  420
TTGAAGGCGA ACGCCGAATT TATTCGCTTG GCGGATTCTT TCGTCGAGGT ACCGGGAGGA  480
AAGAACTTGA ACAACTACGC CAACGTCGAT GTCATTACCC GCATCGCTAA GGAGCAGGGG  540
GTTGATGCCG TTTGGCCTGG ATGGGGTCAT GCATCTGAGA ATCCGAAGCT CCCTAATGCG  600
CTTGACAAAT TGGGAATCAA GTTCATTGGA CCAACTGGGC CTGTCATGAG CGTTTTGGGA  660
GACAAGATTG CTGCGAACAT TCTAGCACAG ACAGCGAAAG TCCCCTCCAT TCCCTGGAGT  720
GGATCCTTTG GTGGACCAGA CGATGGACCC CTTCAGGCGG ATCTGACCGA GGAGGGTACT  780
ATCCCAATGG AAATCTTTAA CAAGGGATTA GTAACCTCTG CTGATGAAGC CGTCATTGTG  840
GCGAACAAGA TTGGCTGGGA GAACGGAATC ATGATCAAGG CTTCTGAGGG TGGAGGAGGA  900
AAGGGTATAC GCTTTGTCGA CAATGAGGCC GACTTACGGA ACGCGTTCGT TCAGGTGTCC  960
AATGAAGTGA TTGGCTCTCC TATTTTCCTC ATGCAGTTGT GTAAGAACGC TCGTCACATC 1020
GAAGTGCAAA TTGTTGGCGA CCAGCACGGA AATGCTGTAG CGTTGAACGG TCGAGATTGC 1080
TCCACTCAGC GTCGCTTCCA GAAGATCTTC GAGGAAGGTC CTCCGTCCAT TGTACCGAAA 1140
GAAACATTCC ACGAGATGGA ACTTGCGGCT CAACGGTTGA CTCAAAACAT TGGGTATCAA 1200
```

UNITED STATES PATENT AND TRADEMARK OFFICE
CERTIFICATE OF CORRECTION

PATENT NO. : 5,559,220

DATED : September 24, 1996

INVENTOR(S) : Paul G. Roessler and John B. Ohlrogge

Page 3 of 5

It is certified that error appears in the above-identified patent and that said Letters Patent is hereby corrected as shown below:

```
GGTGCTGGAA CTGTGGAATA CTTGTACAAC GCCGCTGACA ATAAGTTTTT CTTCCTTGAG 1260
TTGAACCCCC GTCTCCAAGT GGAGCATCCT GTGACTGAAG GAATTACCGG CGCTAATCTT 1320
CCTGCCACTC AGCTTCAAGT TGCTATGGGT ATTCCTCTCT TCAACATTCC TGACATTCGC 1380
CGTCTCTATG GAAGAGAGGA TGCTTACGGA ACGGATCCCA TTGATTTTCT TCAAGAACGT 1440
TACCGCGAAC TCGACTCTCA TGTAATTGCT GCCCGCATCA CTGCTGAAAA CCCCGATGAA 1500
GGATTCAAAC CCACCTCAGG CTCAATTGAG CGAATCAAAT TTCAATCCAC CCCAAATGTT 1560
TGGGGATATT TCTCTGTTGG TGCTAACGGT GGAATCCATG AATTTGCCGA CTCTCAGTTT 1620
GGCCATCTTT TCGCTAAGGG TCCGAACCGT GAGCAAGCCC GCAAGGCATT GGTTTTGGCT 1680
CTTAAGGAGA TGGAAGTGCG CGGAGACATT CGTAACTCTG TTGAATACCT AGTCAAGTTG 1740
CTCGAAACTG AAGCTTTCAA GAAGAACACT ATCGACACGT CTTGGTTAGA TGGCATTATT 1800
AAGGAGAAGT CCGTTAAAGT TGAGATGCCC TCTCACTTAG TGGTTGTCGG AGCCGCTGTT 1860
TTCAAGGCCT TCGAACATGT TAAGGTGGCC ACTGAAGAAG TTAAGGAATC GTTTCGAAAA 1920
GGACAAGTCT CCACTGCAGG GATTCCAGGC ATAAACTCGT TCAACATCGA AGTTGCGTAC 1980
TTAGACACGA AGTACCCATT CCACGTAGAA CGGATCTCTC CAGATGTTTA CAGGTTTACC 2040
TTGGACGGGA ACACGATTGA TGTGGAAGTT ACCCAAACCG CTGAAGGAGC ACTTTTGGCA 2100
ACCTTTGGAG GAGAGACTCA TCGTATCTTT GGTATGGACG AACCACTTGG CCTTCGACTG 2160
TCATTGGACG GGGCAACTGT CCTAATGCCA ACAATTTTTG ACCCCTCTGA ACTCCGCACT 2220
GATGTGACTG GAAAGGTTGT TCGTTACCTC CAAGACAATG GAGCAACTGT TGAAGCGGGC 2280
CAGCCCTATG TCGAGGTTGA AGCGATGAAG ATGATCATGC CAATCAAGGC TACTGAGTCT 2340
GGAAAAATTA CTCACAACCT AAGTGCTGGA TCTGTAATCT CTGCTGGTGA CCTTCTTGCT 2400
TCTCTCGAAC TTAAGGATCC CTCTAGGGTT AAGAAAATAG AAACTTTTTC GGGCAAATTG 2460
GACATTATGG AATCGAAGGT TGACTTAGAA CCGCAGAAAG CAGTCATGAA TGTCCTCTCT 2520
GGGTTCAACT TAGACCCTGA GGCAGTTGCG CAGCAAGCAA TTGACAGTGC TACCGACAGC 2580
TCTGCCGCAG CCGATCTTCT TGTCCAAGTA TTAGACGAAT TCTATCGCGT TGAATCTCAG 2640
TTTGATGGTG TCATCGCTGA TGATGTTGTC CGCACTCTCA CCAAAGCGAA CACCGAGACA 2700
CTTGATGTTG TCATCTCCGA GAACTTGGCC CACCAGCAGC TCAAGAGGCG TAGTCAGCTT 2760
CTCCTCGCTA TGATCCGTCA ACTTGACACG TTTCAAGACA GATTTGGCAG AGAAGTTCCG 2820
GATGCTGTCA TTGAAGCATT GAGTAGGCTT TCTACCTTGA AAGACAAATC TTACGGTGAA 2880
ATCATTCTTG CGGCTGAGGA GAGAGTCCGC GAAGCCAAGG TGCCGTCCTT CGAAGTGCGT 2940
CGTGCTGATT TGCGTGCAAA GCTTGCTGAC CCGGAGACAG ATTTGATTGA CCTGAGTAAG 3000
AGCTCAACAC TCTCAGCAGG GGTTGACCTT CTCACAAATC TTTTTGATGA CGAAGATGAA 3060
TCTGTCCGCG CTGCTGCTAT GGAAGTATAT ACTCGCCGTG TCTACCGTAC CTACAACATC 3120
CCCGAGCTAA CTGTTGGAGT TGAGAATGGC CGCCTCTCAT GTAGCTTCTC CTTCCAATTT 3180
GCTGATGTCC CGGCGAAAGA CCGTGTCACC CGCCAAGGGT TCTTCTCAGT TATCGACGAC 3240
```

UNITED STATES PATENT AND TRADEMARK OFFICE
CERTIFICATE OF CORRECTION

PATENT NO. : 5,559,220

DATED : September 24, 1996

INVENTOR(S) : Paul G. Roessler and John B. Ohlrogge

It is certified that error appears in the above-identified patent and that said Letters Patent is hereby corrected as shown below:

```
GCTTCAAAGT TCGCGCAACA GCTTCCTGAG ATTCTCAACT CGTTTGGATC AAAGATCGCA 3300
GGGGATGCAA GCAAAGAAGG CCCTGTCAAT GTTTTGCAGG TTGGTGCTCT CTCGGGAGAT 3360
ATCAGTATTG AGGACCTCGA GAAAGCTACT TCCGCTAACA AGGACAAGTT GAATATGCTT 3420
GGTGTCCGCA CTGTGACGGC TCTTATCCCA AGGGGAAAGA AGGACCCAAG CTATTATTCA 3480
TTCCCCCAAT GCAGTGGCTT CAAGGAGGAT CCTCTTCGCA GAGGCATGCG CCCAACCTTT 3540
CATCATCTCC TGGAACTCGG ACGGCTGGAG GAAAACTTTG CTCTTGAACG AATTCCTGCA 3600
GTTGGACGCA ACGTACAGAT TTATGTTGGT TCCGAGAAGA CGGCAAGGCG AAATGCAGCT 3660
CAAGTTGTTT TCTTGAGAGC TATCTCACAT ACTCCTGGCC TAACTACCTT CTCTGGTGCA 3720
CGCCGAGCTC TTCTCCAGGG GCTTGACGAA TTGGAACGTG CTCAAGCAAA CTCAAAGGTC 3780
AGTGTCCAGT CATCGTCTCG CATCTACCTT CACTCTCTCC CAGAACAGTC TGATGCAACT 3840
CCCGAGGAGA TTGCTAAAGA ATTCGAAGGT GTCATTGACA AGCTAAAGAG TCGATTGGCC 3900
CAACGTCTTA CGAAACTGCG TGTGGATGAG ATTGAAACCA AGGTTCGCGT GACTGTCCAG 3960
GATGAAGACG GTAGTCCCAG GGTTGTGCCT GTACGCCTTG TGGCTTCTTC AATGCAAGGC 4020
GAATGGCTTA AAACATCTGC TTACATTGAT CGTCCGGACC CGGTCACTGG AGTCACCCGT 4080
GAACGGTGCG TGATTGGAGA AGGCATTGAC GAGGTTTGTG AACTTGAGTC GTATGACTCT 4140
ACCAGTACCA TCCAAACAAA GCGCTCAATT GCAAGACGTG TGGGATCTAC CTACGCTTAT 4200
GACTACCTTG GACTCCTTGA GGTCAGCTTG CTTGGAGAAT GGGATAAGTA TCTCAGCAGT 4260
CTCTCAGGAC CGGACACCCC TACCATCCCG TCGAATGTTT TTGAAGCTCA AGAGTTACTT 4320
GAAGGACCTG ATGGCGAGCT TGTCACCGGG AAACGTGAAA TTGGAACAAA TAAGGTTGGT 4380
ATGGTTGCAT GGGTGGTAAC AATGAAAACA CCTGAATATC CTGAGGGTCG ACAGGTTGTT 4440
GTAATTGTGA ACGATGTCAC TGTACAAAGT GGTTCATTTG GAGTTGAGGA GGATGAAGTT 4500
TTCTTCAAGG CCTCCAAATA TGCTCGCGAA AATAAGCTCC CCCGTGTCTA CATTGCGTGC 4560
AACTCTGGTG CTAGAATTGG TTTGGTGGAT GATCTCAAGC CAAAGTTCCA GATCAAATTC 4620
ATTGATGAGG CGAGTCCATC TAAGGGTTTT GAGTACCTTT ATCTTGATGA TGCAACGTAC 4680
AAATCTCTTC CAGAAGGGTC GGTAAATGTA AGGAAGGTCC CTGAAGGCTG GGCTATCACT 4740
GATATCATTG GAACGAACGA AGGAATTGGG GTTGAGAACC TTCAAGGAAG TGGCAAAATT 4800
GCTGGCGAGA CATCAAGGGC ATATGATGAA ATCTTCACCT TGAGTTACGT CACAGGTAGA 4860
AGTGTTGGTA TTGGAGCTTA CCTTGTCCGT CTCGGCCAGC GTATTATTCA GATGAAACAA 4920
GGACCCATGA TTCTCACAGG CTATGGTGCC CTGAATAAGC TTCTCGGCCG TGAAGTGTAC 4980
AACTCAAACG ACCAACTTGG TGGTCCTCAA GTCATGTTCC CAAACGGCTG CTCTCATGAA 5040
ATTGTAGATG ATGACCAACA AGGCATCCAG TCCATTATCC AATGGCTAAG CTTTGTTCCC 5100
AAGACAACTG ATGCTGTGTC ACCCGTCCGT GAATGTGCCG ACCCTGTCAA CAGGGATGTT 5160
CAATGGCGCC CTACCCCCAC TCCTTATGAT CCACGCCTCA TGCTCTCAGG AACTGACGAG 5220
GAACTCGGTT TTTTTGACAC AGGAAGCTGG AAGGAATATC TTGCTGGCTG GGGGAAGAGT 5280
```

UNITED STATES PATENT AND TRADEMARK OFFICE
CERTIFICATE OF CORRECTION

PATENT NO. : 5,559,220
DATED : September 24, 1996
INVENTOR(S) : Paul G. Roessler and John B. Ohlrogge It is certified that error appears in the above-identified patent and that said Letters Patent is hereby corrected as shown below:

```
GTTGTTATTG GCCGCGGTCG CCTTGGTGGC ATTCCTATGG GTGCTATTGC CGTGGAGACC 5340
CGGCTTGTTG AGAAGATTAT CCCTGCAGAT CCAGCAGACC CCAACTCCCG CGAAGCTGTC 5400
ATGCCCCAGG CTGGACAAGT TCTTTTCCCT GACTCATCCT ACAAGACAGC CCAAGCTCTC 5460
CGCGACTTTA ATAACGAGGG CCTCCCTGTG ATGATTTTCG GCAACTGGCG TGGATTTAGT 5520
GGTGGAAGTC GTGACATGTC TGGTGAAATC CTCAAATTTG GATCCATGAT TGTCGATTCA 5580
CTCCGAGAGT ACAAACATCC TATTTACATA TACTTCCCTC CATATGGTGA ACTTCGAGGA 5640
GGATCGTGGG TTGTGGTGGA CCCCACTATC AATGAGGACA AGATGACCAT GTTCTCAGAT 5700
CCTGATGCTC GTGGTGGTAT TCTCGAACCT GCTGGTATTG TAGAAATCAA GTTCCGCTTG 5760
GCAGACCAGC TGAAAGCCAT GCACCGCATT GATCCCCAGC TGAAGATGCT AGATTCAGAG 5820
CTTGAGTCGA CAGACGACAC AGATGTCGCT GCTCAAGAAG CAATCAAAGA GCAGATTGCT 5880
GCAAGAGAGG AGCTTCTTAA ACCCGTCTAT CTTCAGGCTG CTACTGAATT TGCTGATCTC 5940
CACGACAAGA CGGGACGGAT GAAGGCGAAG GGTGTTATCA AAGAAGCAGT TCCATGGGCT 6000
CGCTCTCGTG AATACTTCTT TTATCTTGCT AAGCGCCGCA TTTTTCAAGA CAACTATGTG 6060
TTGCAAATCA CTGCTGCTGA TCCTTCGTTA GACTCTAAGG CTGCTCTTGA GGTGTTGAAG 6120
AACATGTGCA CTGCAGACTG GGATGACAAC AAAGCCGTTC TTGACTATTA TCTGTCCAGC 6180
GATGGAGACA TCACAGCCAA GATTAGCGAG ATGAAGAAGG CAGCTATCAA GGCACAGATC 6240
GAGCAGCTTC AGAAAGCTTT GGAGGGTTGA                                  6270
```

Signed and Sealed this

Eighteenth Day of February, 1997

Attest:

BRUCE LEHMAN

*Attesting Officer*    *Commissioner of Patents and Trademarks*